(12) United States Patent
Kawaue et al.

(10) Patent No.: US 8,541,157 B2
(45) Date of Patent: Sep. 24, 2013

(54) RESIST COMPOSITION, METHOD OF FORMING RESIST PATTERN, COMPOUND AND ACID GENERATOR INCLUDING THE SAME

(75) Inventors: Akiya Kawaue, Kawasaki (JP); Yoshiyuki Utsumi, Kawasaki (JP); Sho Abe, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 569 days.

(21) Appl. No.: 12/567,643

(22) Filed: Sep. 25, 2009

(65) Prior Publication Data
US 2010/0081088 A1 Apr. 1, 2010

(30) Foreign Application Priority Data

Sep. 30, 2008 (JP) ................ 2008-252212
Sep. 11, 2009 (JP) ................ 2009-210857

(51) Int. Cl.
*G03F 7/038* (2006.01)
*G03F 7/039* (2006.01)
*G03F 7/20* (2006.01)
*G03F 7/30* (2006.01)

(52) U.S. Cl.
USPC ........ 430/270.1; 430/921; 430/925; 430/325; 430/326; 430/311; 430/910; 430/919; 430/920; 560/9; 560/61; 568/74; 568/75; 568/77

(58) Field of Classification Search
None
See application file for complete search history.

(56) References Cited

U.S. PATENT DOCUMENTS

| | | | |
|---|---|---|---|
| 5,034,304 A | 7/1991 | Feely | |
| 5,945,517 A | 8/1999 | Nitta et al. | |
| 6,153,733 A | 11/2000 | Yukawa et al. | |
| 6,358,665 B1 * | 3/2002 | Pawlowski et al. | ........ 430/270.1 |
| 2001/0049073 A1 | 12/2001 | Hada et al. | |

FOREIGN PATENT DOCUMENTS

| | | |
|---|---|---|
| JP | H08-003635 | 7/1987 |
| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| JP | 2000-206694 | 7/2000 |
| JP | 2005-037888 | 2/2005 |
| WO | WO 2004-074242 | 9/2004 |
| WO | WO 2004/076495 | 9/2004 |

OTHER PUBLICATIONS

Tsuchiya et al., Investigation of Acid-Catalyzed Insolubilization Reactions for Alicyclic Polymers with Carboxyl Groups, *Journal of Photopolymer Science and Technology*, vol. 10, No. 4, pp. 579-584, (1997).

Maeda et al., ArF Chemically Amplified Negative Resist Using Alicyclic Epoxy Polymer, *Journal of Photopolymer Science and Technology*, vol. 11, No. 3, pp. 507-512, (1998).

Iwasa et al., Novel Negative photoresist based on polar Alicyclic polymers for Arf excimer laser lithography, Proceedings of SPIE, vol. 3333, pp. 417-424, (1998).

Conley, Will et al., Negative Photoresiste for 157 nm Microlithography: A Progress Report, Advances in Resist Technology and Processing XIX, Theodore H. Fedynyshyn et al., Proceedings of SPIE, vol. 4690, pp. 94-100, (2002).

* cited by examiner

*Primary Examiner* — Sin J. Lee
(74) *Attorney, Agent, or Firm* — Knobbe Martens Olson & Bear LLP

(57) ABSTRACT

A resist composition including a base component (A) which exhibits changed solubility in an alkali developing solution under the action of acid and an acid-generator component (B) which generates acid upon exposure, wherein the acid-generator component (B) includes an acid generator (B1) composed of a compound having a base dissociable group within a cation moiety.

12 Claims, No Drawings

RESIST COMPOSITION, METHOD OF FORMING RESIST PATTERN, COMPOUND AND ACID GENERATOR INCLUDING THE SAME

BACKGROUND OF THE INVENTION

1. Field of the Invention

The present invention relates to a resist composition, a method of forming a resist pattern using the resist composition, a compound useful as an acid generator for the resist composition, and the acid generator.

Priority is claimed on Japanese Patent Application No. 2008-252212, filed Sep. 30, 2008, and Japanese Patent Application No. 2009-210857, filed Sep. 11, 2009, the content of which is incorporated herein by reference.

2. Description of Related Art

In lithography techniques, for example, a resist film composed of a resist material is formed on a support such as a substrate, and the resist film is subjected to selective exposure of radial rays such as light or electron beam through a mask having a predetermined pattern, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays, mass production of semiconductor elements using KrF excimer lasers and ArF excimer lasers has commenced. Furthermore, research is also being conducted into lithography techniques that use an exposure light source having a wavelength shorter than these excimer lasers, such as $F_2$ excimer lasers, electron beams, extreme ultraviolet radiation (EUV), and X rays.

Conventionally, negative resist materials for use in processes that use either i-line radiation or a KrF excimer laser (248 nm) as the light source have employed chemically amplified negative resist compositions containing a combination of an acid generator, an alkali-soluble resin such as a novolak resin or a polyhydroxystyrene, and an amino resin such as a melamine resin or urea resin (for example, refer to Patent Document 1).

Furthermore, negative resist materials that can be applied to processes that use an ArF excimer laser of even shorter wavelength (193 nm) use materials that exhibit improved transparency to ArF excimer lasers. For example, a negative resist composition that includes a resin component containing carboxyl groups, a cross-linking agent containing alcoholic hydroxyl groups, and an acid generator has been proposed.

In this composition, the carboxyl groups within the resin component react with the alcoholic hydroxyl groups within the cross-linking agent under the action of the acid generated from the acid generator. As a result, the resin component changes from an alkali-soluble state to an alkali-insoluble state.

Furthermore, negative resist compositions have also been proposed that include a resin component containing carboxyl groups or carboxylate ester groups as well as alcoholic hydroxyl groups, and an acid generator, wherein an intermolecular reaction between the carboxyl groups or carboxylate ester groups and the alcoholic hydroxyl groups within the resin component, under the action of the acid generated from the acid generator, causes the resin component to change from an alkali-soluble state to an alkali-insoluble state (for example, see Non-patent Documents 1 to 4 and Patent Document 2).

As acid generators usable in a chemically amplified resist composition, various types have been proposed including, for example, onium salt-based acid generators such as iodonium salts and sulfonium salts; oxime sulfonate-based acid generators; diazomethane-based acid generators; nitrobenzylsulfonate-based acid generators; iminosulfonate-based acid generators; and disulfone-based acid generators.

Currently, as acid generators, onium salt-based acid generators having an onium ion such as triphenylsulfonium as the cation moiety are used. As the anion moiety for onium salt-based acid generators, an alkylsulfonate ion or a fluorinated alkylsulfonate ion in which a part or all of the hydrogen atoms within the aforementioned alkylsulfonate ion has been substituted with fluorine atoms is typically used (for example, refer to Patent Document 3).

In those cases where such onium salt-based acid generators are used, it is considered that length of the alkyl group or fluorinated alkyl group within the anion moiety is preferably long, as diffusion of acid within a resist film after exposure can be suppressed. However, an alkyl group or fluorinated alkyl group having 6 or more carbon atoms is hardly decomposable, and hence, in consideration of safety in handling in terms of bioaccumulation, those having 4 or less carbon atoms, for example, a nonafluorobutanesulfonic acid ion or the like are used.

[Patent Document 1] Japanese Examined Patent Application, Second Publication No. Hei 8-3635
[Patent Document 2] Japanese Unexamined Patent Application, First Publication No. 2000-206694
[Patent Document 3] Japanese Unexamined Patent Application, First Publication No. 2005-37888
[Non-Patent Document 1] J. Photopolym. Sci. Tech., Vol. 10, No. 4, pages 579 to 584 (1997)
[Non-Patent Document 2] J. Photopolym. Sci. Tech., Vol. 11, No. 3, pages 507 to 512 (1998)
[Non-Patent Document 3] SPIE Advances in Resist Technology and Processing XIV, Vol. 3333, pages 417 to 424 (1998)
[Non-Patent Document 4] SPIE Advances in Resist Technology and Processing XIX, Vol. 4690, pages 94 to 100 (2002)

In recent years, as requirements for high resolution increase with progress in the miniaturization of resist patterns, improvement in various lithography properties has been demanded. Further, associated with this trend, development of novel resist materials has been desired.

As the cation for onium salt-based acid generators that have been conventionally used in resist materials, for example, cations such as triphenylsulfonium have typically been used. Because the cations exhibit relatively high hydrophobicity, it is presumed that onium salt-based acid generators having such cations are excellent in terms of compatibility with the base components of resists and the solubility in an organic solvent, and are thus contributing to the improvements in lithography properties.

However, the solubility of acid generators in an alkali developing solution tends to deteriorate as the hydrophobicity increases. When the solubility of an acid generator in an alkali developing solution deteriorates, the acid generator does not dissolve satisfactorily at the time of development, which may cause problems such as the occurrence of defects and the footing of resist patterns. The term "defects" refers to general abnormalities of a resist pattern, which are detected when observed from right above the developed resist pattern, using, for example, a surface defect detection apparatus (trade name: "KLA") manufactured by KLA-TENCOR Corporation. Examples of these abnormalities include post-developing scum, foam, dust, bridges across different portions of the resist pattern, color irregularities, and foreign deposits.

Therefore, development of a novel compound which can achieve both excellent solubility in developing solutions and satisfactory lithography properties and which is more useful as an acid generator for a resist composition has been demanded.

The present invention takes the above circumstances into consideration, with an object of providing a novel compound useful as an acid generator for a resist composition, an acid generator including the compound, a resist composition containing the acid generator, and a method of forming a resist pattern that uses the resist composition.

SUMMARY OF THE INVENTION

In order to achieve the above object, the present invention adopts the aspects described below.

Specifically, a first aspect of the present invention is a resist composition including a base component (A) which exhibits changed solubility in an alkali developing solution under the action of acid and an acid-generator component (B) which generates acid upon exposure, wherein the acid-generator component (B) includes an acid generator (BI) composed of a compound having a base dissociable group within a cation moiety.

A second aspect of the present invention is a method of forming a resist pattern, including: applying a resist composition of the first aspect to a substrate to form a resist film on the substrate; subjecting said resist film to exposure; and subjecting said resist film to alkali developing to form a resist pattern.

A third aspect of the present invention is a compound represented by general formula (b1-11) shown below.

[Chemical Formula 1]

(b1-11)

wherein $R^{7'''}$ to $R^{9'''}$ each independently represents an aryl group or an alkyl group, wherein two of $R^{7'''}$ to $R^{9'''}$ may be bonded to each other to form a ring with the sulfur atom in the formula, and at least one of $R^{7'''}$ to $R^{9'''}$ represents a substituted aryl group having a group represented by general formula (I) shown below as a substituent; and $X^-$ represents an anion.

[Chemical Formula 2]

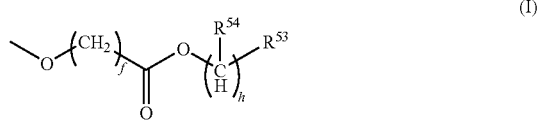

(I)

wherein $R^{53}$ represents a hydrogen atom or a fluorinated alkyl group; $R^{54}$ represents a hydrogen atom, an alkyl group or a fluorinated alkyl group; f represents 0 or 1; and h represents 1 or 2.

A fourth aspect of the present invention is an acid generator including the compound of the third aspect.

In the present descriptions and the claims, the term "alkyl group" includes linear, branched or cyclic, monovalent saturated hydrocarbon groups, unless otherwise specified.

The term "alkylene group" includes linear, branched or cyclic divalent saturated hydrocarbon groups, unless otherwise specified.

A "lower alkyl group" is an alkyl group of 1 to 5 carbon atoms.

A "halogenated alkyl group" is a group in which a part or all of the hydrogen atoms of an alkyl group is substituted with halogen atoms. Examples of the halogen atom include a fluorine atom, a chlorine atom, a bromine atom and an iodine atom.

The term "aliphatic" is a relative concept used in relation to the term "aromatic", and defines a group or compound that has no aromaticity.

The term "structural unit" refers to a monomer unit that contributes to the formation of a resin component (namely, a polymer or copolymer).

The term "exposure" is used as a general concept that includes irradiation with any form of radiation.

According to the present invention, there are provided a novel compound useful as an acid generator for a resist composition, an acid generator including the compound, a resist composition containing the acid generator, and a method of forming a resist pattern that uses the resist composition.

DETAILED DESCRIPTION OF THE INVENTION

<<Resist Composition>>

A resist composition according to the first aspect of the present invention includes a base component (A) (hereafter, referred to as "component (A)") which exhibits changed solubility in an alkali developing solution under the action of acid and an acid generator component (B) (hereafter, referred to as "component (B)") which generates acid upon exposure.

In the resist composition, when acid is generated from the component (B) upon exposure, the action of the generated acid causes a change in the solubility of the component (A) in an alkali developing solution. As a result, in the formation of a resist pattern, when a resist film formed using the resist composition of the present invention is subjected to selective exposure, the solubility in the alkali developing solution of the exposed portions of the resist film changes, whereas the solubility in the alkali developing solution of the unexposed portions remains unchanged, and hence, a resist pattern can be formed by alkali developing the resist film.

The resist composition of the present invention may be either a positive resist composition or a negative resist composition, and may also include a fluorine-containing polymeric compound (F) described later (hereafter, referred to as "component (F)") in addition to the aforementioned components (A) and (B).

When the resist composition of the present invention is a negative resist composition, it is preferable that the resist composition further include a cross-linking agent (C) described later (hereafter, referred to as "component (C)") in addition to the aforementioned components (A) and (B).

By separately describing the cases where the resist composition of the present invention is a positive resist composition and the cases where the resist composition of the present invention is a negative resist composition, the respective components will be described in more detail below.

<<Component (A)>>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compounds having a molecular weight of 500 or more that may be used as the base component are broadly classified into low molecular weight organic compounds having a molecular weight of 500 to less than 2,000 (namely, "low molecular weight materials") and high molecular weight organic compounds having a molecular weight of 2,000 or more (namely "polymeric materials"). Generally, a non-polymer is used as the low molecular weight material. A resin (a polymer or copolymer) is used as the polymeric material. With respect to the aforementioned resin, the "molecular weight" refers to the polystyrene equivalent weight average molecular weight determined by gel permeation chromatography (GPC). Hereafter, the simplified term "resin" refers to a resin having a molecular weight of 2,000 or more.

As the component (A), a resin which exhibits changed alkali solubility under the action of acid or a low molecular weight material which exhibits changed alkali solubility under the action of acid may be used. Alternatively, a combination of these materials may also be used.

When the resist composition of the present invention is a positive resist composition, as the component (A), a base component (A1) (hereafter, referred to as "component (A1)") which exhibits increased solubility in an alkali developing solution by the action of acid is preferable.

More specifically, the component (A1) is substantially insoluble in an alkali developing solution prior to exposure, but when acid is generated from the component (B) upon exposure, the action of this acid causes an increase in the solubility of the component (A1) in an alkali developing solution. Therefore, in the formation of a resist pattern, by conducting selective exposure of a resist film formed by applying the positive resist composition onto a substrate, the exposed portions change from an insoluble state to a soluble state in an alkali developing solution, whereas the unexposed portions remain insoluble in an alkali developing solution, and hence, a resist pattern can be formed by alkali developing.

The component (A1) may be a resin component (A1-1) that exhibits increased solubility in an alkali developing solution under the action of acid (hereafter, referred to as "copolymer (A1-1)"), a low molecular weight material (A1-2) that exhibits increased solubility in an alkali developing solution under the action of acid (hereafter, referred to as "component (A1-2)"), or a mixture of the copolymer (A1-1) and the component (A1-2).

When the resist composition of the present invention is a positive resist composition, the component (A) preferably includes the copolymer (A1-1).

When the resist composition of the present invention is a negative resist composition, as the component (A), a base component (A2) (hereafter, referred to as "component (A2)") that is soluble in an alkali developing solution is preferable. This negative resist composition includes the aforementioned component (B) in addition to the component (A2), and preferably further includes a cross-linking agent (C) (hereafter, referred to as "component (C)").

In the negative resist composition, when acid is generated from the component (B) upon exposure, the action of the generated acid causes cross-linking between the component (A2) and the cross-linking agent, rendering the composition substantially insoluble in an alkali developing solution. As a result, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

The component (A2) may be a resin component (A2-1) that is soluble in an alkali developing solution (hereafter, referred to as "copolymer (A2-1)"), a low molecular weight compound that is soluble in an alkali developing solution (hereafter, frequently referred to as "component (A2-2)"), or a mixture of the copolymer (A2-1) and the component (A2-2).

When the resist composition of the present invention is a negative resist composition, the component (A) preferably includes the copolymer (A2-1).

In the present invention, there are no particular limitations on the component (A), and any of the multitude of groups that have been proposed for the resins used within positive or negative resist compositions designed for use with electron beam (EB), KrF excimer lasers and ArF excimer lasers can be used. Of these, the resins used within positive or negative resist compositions that are suitably used with ArF excimer lasers are preferable.

Preferred examples of the copolymer (A1-1) used in the present invention include a copolymer having a structural unit (a1) derived from an acrylate ester containing an acid dissociable, dissolution inhibiting group which will be described later.

Further, it is more preferable that in addition to the structural unit (a1), the copolymer (A1-1) also has a structural unit (a2) derived from an acrylate ester that contains a lactone-containing cyclic group.

Moreover, it is particularly desirable that in addition to the structural unit (a1), or in addition to the combination of the structural units (a1) and (a2), the copolymer (A1-1) also has a structural unit (a3) derived from an acrylate ester that contains a polar group-containing aliphatic hydrocarbon group.

Furthermore, the copolymer (A1-1) may also include a structural unit (a4) which is other than the above-mentioned structural units (a1) to (a3).

As the copolymer (A2-1) used in the present invention, an alkali-soluble resin having a fluorinated hydroxyalkyl group such as that represented by general formula (a1'-1-1) which will be described later is preferable. Specific examples of the preferred forms thereof include a copolymer having a structural unit (a1') that contains, within the main chain, an aliphatic cyclic group having a fluorinated hydroxyalkyl group represented by the aforementioned general formula (a1'-1-1), and a structural unit (a2') having a hydroxyalkyl group.

Furthermore, the copolymer (A2-1) may also include a structural unit (a3') which is other than the above-mentioned structural units (a1') and (a2').

The components (A1) and (A2) suitably used in the present invention will be described below using examples.

<Component (A1)>
[Copolymer (A1-1)]

As the copolymer (A1-1), a resin component (base resin) typically used as a base component for a chemically amplified resist composition can be used alone, or two or more of such resin components can be mixed together. In the present invention, it is preferable that the copolymer (A1-1) includes a structural unit derived from an acrylate ester. It is particularly desirable that the copolymer (A1-1) be a resin including a structural unit (a1) derived from an acrylate ester that contains an acid dissociable, dissolution inhibiting group, as it enables formation of an excellent resist pattern with minimal swelling. Here, the term "structural unit derived from an acrylate ester" refers to a structural unit which is formed by the cleavage of the ethylenic double bond of an acrylate ester. Further, the term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be mentioned. With respect to the "structural unit derived from an acrylate ester", the "α-position (the carbon atom on the α-position)" refers to the carbon atom having the carbonyl group bonded thereto, unless specified otherwise.

In the acrylate ester, the lower alkyl group for the substituent at the α-position is an alkyl group of 1 to 5 carbon atoms, and specific examples thereof include linear or branched alkyl groups such as a methyl group, an ethyl group, a propyl group, an isopropyl group, an n-butyl group, an isobutyl group, a tert-butyl group, a pentyl group, an isopentyl group and a neopentyl group. A "halogenated alkyl group" is a group in which a part or all of the hydrogen atoms of the above-mentioned lower alkyl group is substituted with halogen atoms. Examples of the halogen atom include a fluorine atom, a chlorine atom, a bromine atom and an iodine atom.

—Structural Unit (a1)

Structural unit (a1) is a structural unit derived from an acrylate ester having an acid dissociable, dissolution inhibiting group.

The acid dissociable, dissolution inhibiting group within the structural unit (a1) has an alkali dissolution inhibiting effect that renders the entire component (A1) insoluble in an alkali developing solution prior to dissociation, and then following dissociation under the action of acid, increases the solubility of the entire component (A1) in the alkali developing solution. As the acid dissociable, dissolution inhibiting group within the structural unit (a1), any of the groups that have been proposed as acid dissociable, dissolution inhibiting groups for the base resins of chemically amplified resists can be used. Generally, groups that form either a cyclic or chain-like tertiary alkyl ester with the carboxyl group of the (meth)acrylic acid, and acetal-type acid dissociable, dissolution inhibiting groups such as alkoxyalkyl groups are widely known. Here, the term "(meth)acrylic acid" is a generic term that includes either or both of acrylic acid having a hydrogen atom bonded to the α-position and methacrylic acid having a methyl group bonded to the α-position.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of these tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

In the present description, the term "aliphatic" is a relative concept used in relation to the term "aromatic", and defines a group or compound that has no aromaticity.

The term "aliphatic branched" refers to a branched structure having no aromaticity.

The "aliphatic branched, acid dissociable, dissolution inhibiting group" is not limited to be constituted from only carbon atoms and hydrogen atoms (not limited to hydrocarbon groups), but is preferably a hydrocarbon group.

Further, the "hydrocarbon group" may be either saturated or unsaturated, but in general, the hydrocarbon group is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include a lower alkyl group of 1 to 5 carbon atoms, a lower alkoxy group of 1 to 5 carbon atoms, a fluorine atom, a fluorinated lower alkyl group of 1 to 5 carbon atoms which is substituted by a fluorine atom, and an oxygen atom (=O).

The basic ring of the "aliphatic cyclic group" exclusive of substituents is not limited to structures constituted from only carbon and hydrogen (not limited to hydrocarbon groups), but is preferably a hydrocarbon group.

Further, the "hydrocarbon group" may be either saturated or unsaturated, but in general, the hydrocarbon group is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated alkyl group, may be exemplified. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cyclic alkyl group can be mentioned. Specific examples include a 2-methyl-2-adamantyl group and a 2-ethyl-2-adamantyl group. Alternatively, groups having an aliphatic cyclic group such as an adamantyl group, cyclohexyl group, cyclopentyl group, norbornyl group, tricyclodecanyl group or tetracyclododecanyl group, and a branched alkylene group having a tertiary carbon atom bonded thereto, as the groups bonded to the oxygen atom of the carbonyloxy group (—C(O)—O—) in the structural units represented by general formulas (a1"-1) to (a1"-6) shown below, may also be exemplified.

[Chemical Formula 3]

(a1″-1) 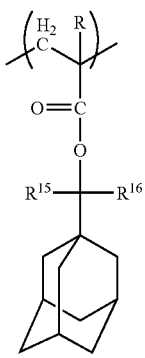

(a1″-2) 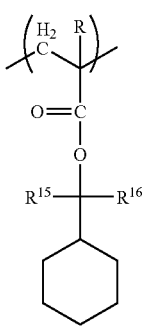

(a1″-3) 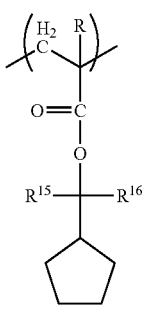

(a1″-4) 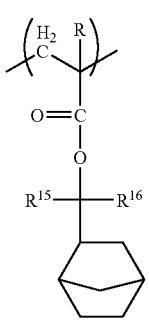

(a1″-5) 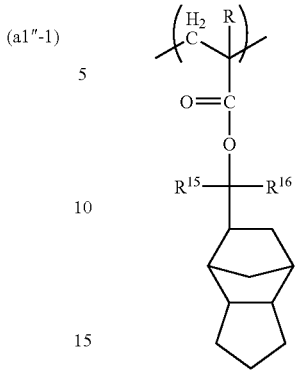

(a1″-6) 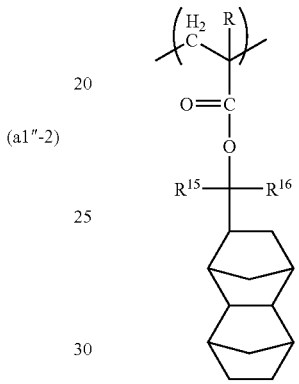

wherein R represents a hydrogen atom, a lower alkyl group of 1 to 5 carbon atoms or a halogenated lower alkyl group; and $R^{15}$ and $R^{16}$ each independently represents an alkyl group (which may be linear or branched, and preferably has 1 to 5 carbon atoms).

In general formulas (a1″-1) to (a1″-6) above, the lower alkyl group or halogenated lower alkyl group for R are the same as the lower alkyl group or halogenated lower alkyl group which can be bonded to the α-position of the aforementioned acrylate ester.

An "acetal-type acid dissociable, dissolution inhibiting group" generally substitutes a hydrogen atom at the terminal of an alkali-soluble group such as a carboxyl group or a hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 4]

(p1) 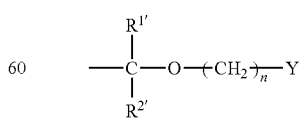

wherein $R^{1'}$ and $R^{2'}$ each independently represents a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1'}$ and $R^{2'}$, the same as the lower alkyl groups for R above can be exemplified. As the lower alkyl group for $R^{1'}$ and $R^{2'}$, a methyl group or an ethyl group is preferable, and a methyl group is particularly desirable.

In the present invention, it is preferable that at least one of $R^{1'}$ and $R^{2'}$ be a hydrogen atom. That is, it is preferable that the acid dissociable, dissolution inhibiting group (p1) is a group represented by general formula (p1-1) shown below.

[Chemical Formula 5]

(p1-1)

wherein $R^{1'}$, n and Y are respectively as defined for $R^{1'}$, n and Y in general formula (p1) above.

As the lower alkyl group for Y, the same as the lower alkyl groups for R above can be exemplified.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be exemplified.

Further, as the acetal-type, acid dissociable, dissolution inhibiting group, groups represented by general formula (p2) shown below can also be exemplified.

[Chemical Formula 6]

(p2)

wherein $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, wherein the terminal of $R^{17}$ may be bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable. It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or a methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, and which may or may not be substituted with fluorine atoms or fluorinated alkyl groups. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto and the carbon atom having the oxygen atom and $R^{17}$ bonded thereto. Such a cyclic group is preferably a 4 to 7-membered ring, and more preferably a 4 to 6-membered ring. Specific examples of the cyclic group include a tetrahydropyranyl group and a tetrahydrofuranyl group.

As the structural unit (a1), it is preferable to use at least one member selected from the group consisting of structural units represented by general formula (a1-0-1) shown below and structural units represented by general formula (a1-0-2) shown below.

[Chemical Formula 7]

(a1-0-1)

wherein R represents a hydrogen atom, a lower alkyl group or a halogenated lower alkyl group; and $X^1$ represents an acid dissociable, dissolution inhibiting group.

[Chemical Formula 8]

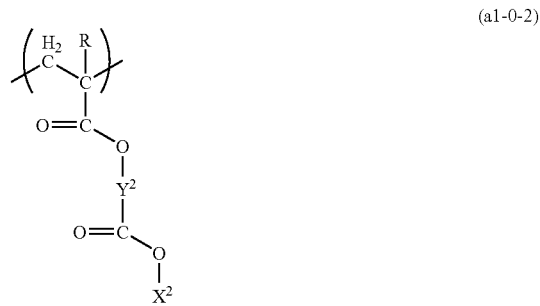

(a1-0-2)

wherein R represents a hydrogen atom, a lower alkyl group or a halogenated lower alkyl group; $X^2$ represents an acid dissociable, dissolution inhibiting group; and $Y^2$ represents a divalent linking group.

In general formula (a1-0-1) shown above, the lower alkyl group and halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is as defined for R in general formula (a1-0-1) above.

$X^2$ is the same as $X^1$ in general formula (a1-0-1).

As the divalent linking group for $Y^2$, an alkylene group, a divalent aliphatic cyclic group, a divalent linking group containing a hetero atom, or a combination of these groups can be used.

As the aliphatic cyclic group, the same groups as those exemplified above in connection with the explanation of the "aliphatic cyclic group" can be used, with the exception that two hydrogen atoms have been removed therefrom.

When $Y^2$ represents an alkylene group, it preferably has 1 to 10 carbon atoms, more preferably 1 to 6 carbon atoms, still more preferably 1 to 4 carbon atoms, and most preferably 1 to 3 carbon atoms.

In those cases where $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

When $Y^2$ represents a divalent linking group containing a hetero atom, examples of the divalent linking groups containing a hetero atom include —O—, —C(=O)—O—, —C(=O)—, —O—C(=O)—O—, —C(=O)—NH—, —NR$^{04}$— (wherein R$^{04}$ represents an alkyl group, an acyl group or the like), —NH—C(=O)—, =N—, —S—, —S(=O)$_2$—, —S(=O)$_2$—O—, or -A-O—B— (wherein each of A and B independently represents a divalent hydrocarbon group which may have a substituent, and O is an oxygen atom).

In the group —NR$^{04}$— for $Y^2$, R$^{04}$ preferably has 1 to 10 carbon atoms, more preferably 1 to 8 carbon atoms, and most preferably 1 to 5 carbon atoms.

When $Y^2$ is "A-O—B", each of A and B independently represents a divalent hydrocarbon group which may have a substituent. When a hydrocarbon group "has a substituent", it means that a part or all of the hydrogen atoms within the hydrocarbon group are substituted with groups or atoms other than hydrogen atoms.

The hydrocarbon group represented by A may be either an aliphatic hydrocarbon group or an aromatic hydrocarbon group. An aliphatic hydrocarbon group refers to a hydrocarbon group that has no aromaticity.

The aliphatic hydrocarbon group represented by A may be either saturated or unsaturated, but in general, the aliphatic hydrocarbon group is preferably saturated.

More specific examples of the aliphatic hydrocarbon group represented by A include linear or branched aliphatic hydrocarbon groups, and aliphatic hydrocarbon groups that contain a ring within their structures.

The linear or branched aliphatic hydrocarbon group preferably has 1 to 10 carbon atoms, more preferably 1 to 8 carbon atoms, still more preferably 2 to 5 carbon atoms, and most preferably 2 carbon atoms.

As the linear aliphatic hydrocarbon group, linear alkylene groups are preferred, and specific examples include a methylene group, an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As the branched aliphatic hydrocarbon group, branched alkylene groups are preferred, and specific examples include various alkylalkylene groups, including alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; alkyltrimethylene groups such as —CH(CH$_3$)CH$_2$CH$_2$— and —CH$_2$CH(CH$_3$)CH$_2$—; and alkyltetramethylene groups such as —CH(CH$_3$)CH$_2$CH$_2$CH$_2$— and —CH$_2$CH(CH$_3$)CH$_2$CH$_2$—. As the alkyl group within the alkylalkylene group, a linear alkyl group of 1 to 5 carbon atoms is preferable.

The linear or branched (chain-like) aliphatic hydrocarbon group may or may not have a substituent. Examples of the substituent include a fluorine atom, a fluorinated lower alkyl group of 1 to 5 carbon atoms which is substituted by a fluorine atom, and an oxygen atom (=O).

Examples of the aliphatic hydrocarbon groups that contain a ring within their structures include cyclic aliphatic hydrocarbon groups (groups in which two hydrogen atoms have been removed from an aliphatic hydrocarbon ring), and groups in which this type of cyclic aliphatic hydrocarbon group is either bonded to the terminal of an above-mentioned chain-like aliphatic hydrocarbon group or positioned partway along the chain-like aliphatic hydrocarbon group.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Specific examples of the polycycloalkane include adamantane, norbornane, isobornane, tricyclodecane and tetracyclododecane.

The cyclic aliphatic hydrocarbon groups may or may not have a substituent. Examples of substituents include a lower alkyl group of 1 to 5 carbon atoms, a fluorine atom, a fluorinated lower alkyl group of 1 to 5 carbon atoms which is substituted by a fluorine atom, and an oxygen atom (=O).

The group A is preferably a linear aliphatic hydrocarbon group, more preferably a linear alkylene group, still more preferably a linear alkylene group of 2 to 5 carbon atoms, and most preferably a methylene group or an ethylene group.

Examples of the hydrocarbon group represented by B include the same divalent hydrocarbon groups as those exemplified above in relation to the hydrocarbon group represented by A.

As the group B, a linear or branched aliphatic hydrocarbon group is preferred, and a methylene group or an alkylmethylene group is particularly desirable.

The alkyl group within the alkylmethylene group is preferably a linear alkyl group of 1 to 5 carbon atoms, is more preferably a linear alkyl group of 1 to 3 carbon atoms, and is most preferably a methyl group.

As the divalent linking group for $Y^2$, an alkylene group, a divalent aliphatic cyclic group or a divalent linking group containing an alkylene group and hetero atom are more preferable, and a divalent linking group containing an alkylene group and hetero atom is particularly desirable.

Specific examples of the structural unit (a1) include structural units represented by general formulas (a1-1) to (a1-4) shown below.

[Chemical Formula 9]

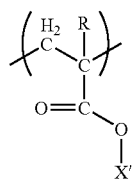
(a1-1)

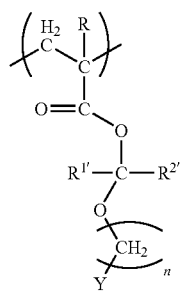
(a1-2)

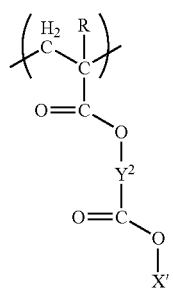
(a1-3)

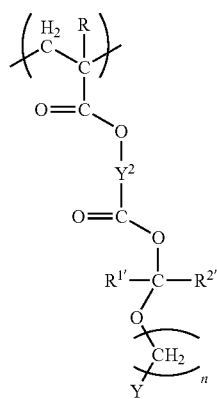
(a1-4)

wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents a divalent linking group; R represents a hydrogen atom, a lower alkyl group or a halogenated lower alkyl group; and $R^{1'}$ and $R^{2'}$ each independently represents a hydrogen atom or a lower alkyl group of 1 to 5 carbon atoms.

In general formulas (a1-1) to (a1-4), the lower alkyl group and halogenated lower alkyl group for R are the same as the lower alkyl group and halogenated lower alkyl group which can be bonded to the α-position of the aforementioned acrylate ester.

Examples of the tertiary alkyl ester-type acid dissociable, dissolution inhibiting group for X' in the formula above are the same as the above-exemplified tertiary alkyl ester-type acid dissociable, dissolution inhibiting groups for $X^1$.

As $R^{1'}$, $R^{2'}$, n and Y, the same as $R^{1'}$, $R^{2'}$, n and Y defined for general formula (p1) described above in connection with the "acetal-type acid dissociable, dissolution inhibiting group" may be used.

As $Y^2$, the same $Y^2$ as defined for general formula (a1-0-2) above may be used.

Specific examples of structural units represented by general formulas (a1-1) to (a1-4) are shown below.

[Chemical Formula 10]

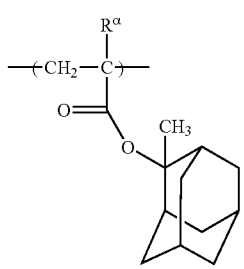
(a1-1-1)

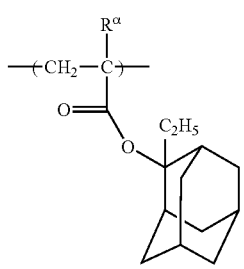
(a1-1-2)

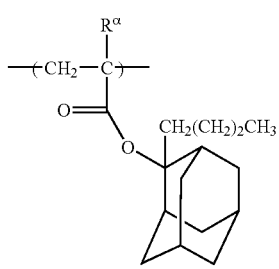
(a1-1-3)

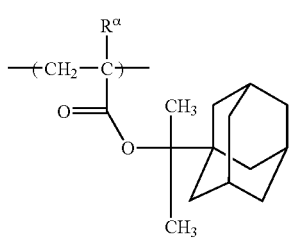
(a1-1-4)

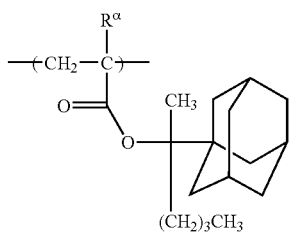
(a1-1-5)

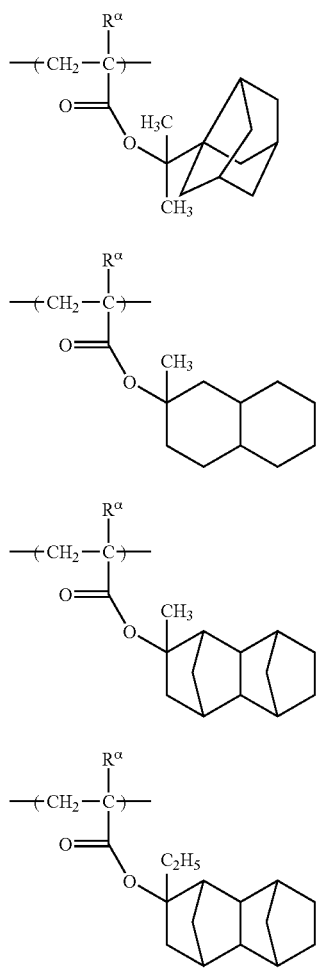
(a1-1-6)
(a1-1-7)
(a1-1-8)
(a1-1-9)
[Chemical Formula 11]
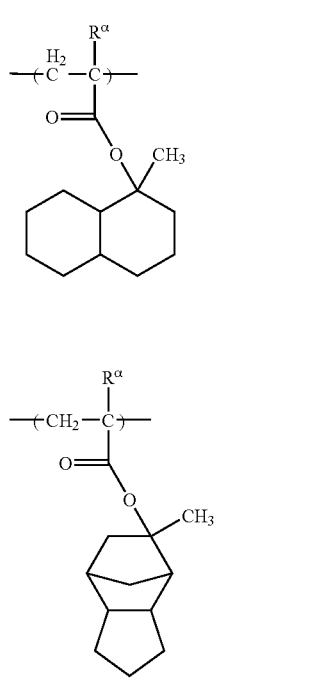
(a1-1-10)
(a1-1-11)
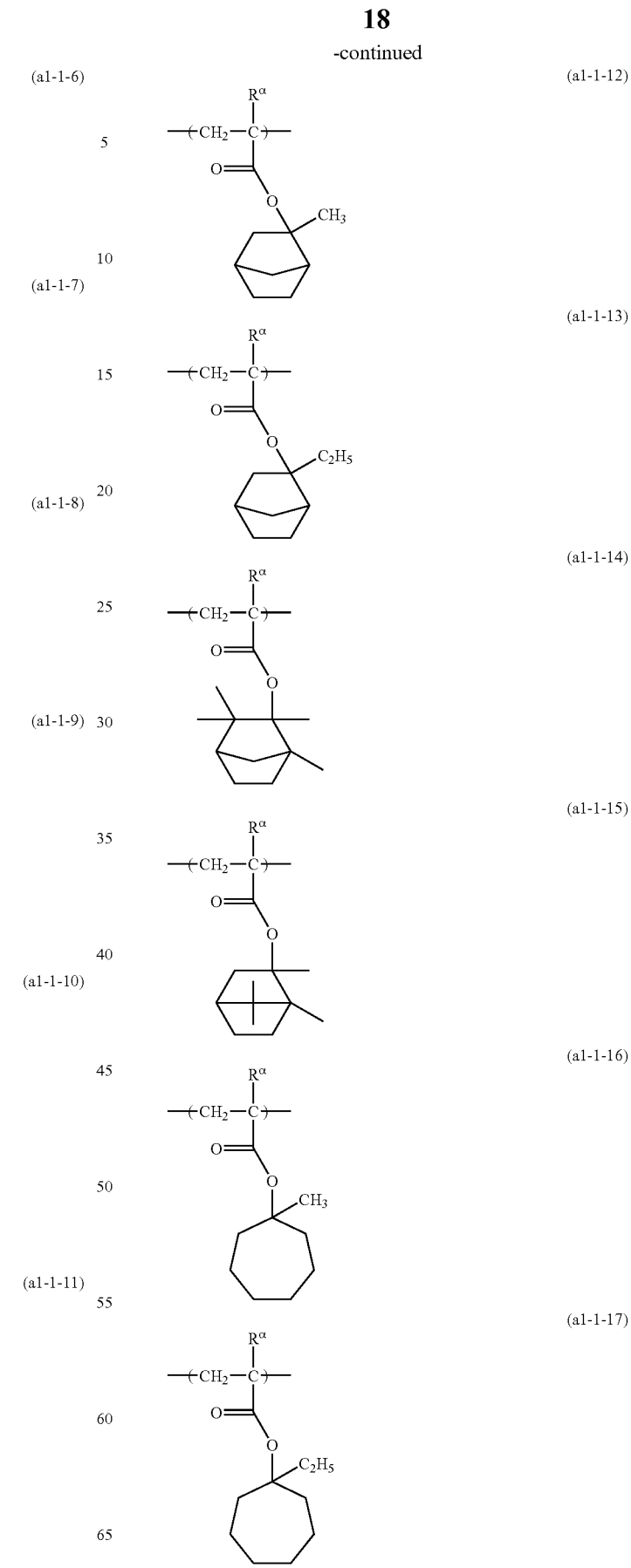
(a1-1-12)
(a1-1-13)
(a1-1-14)
(a1-1-15)
(a1-1-16)
(a1-1-17)

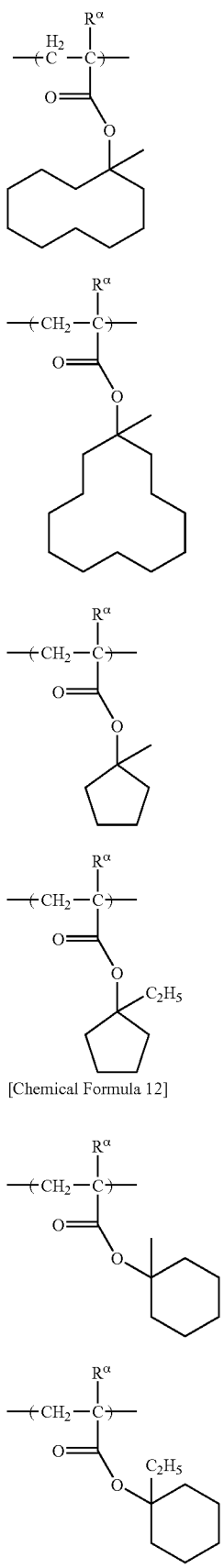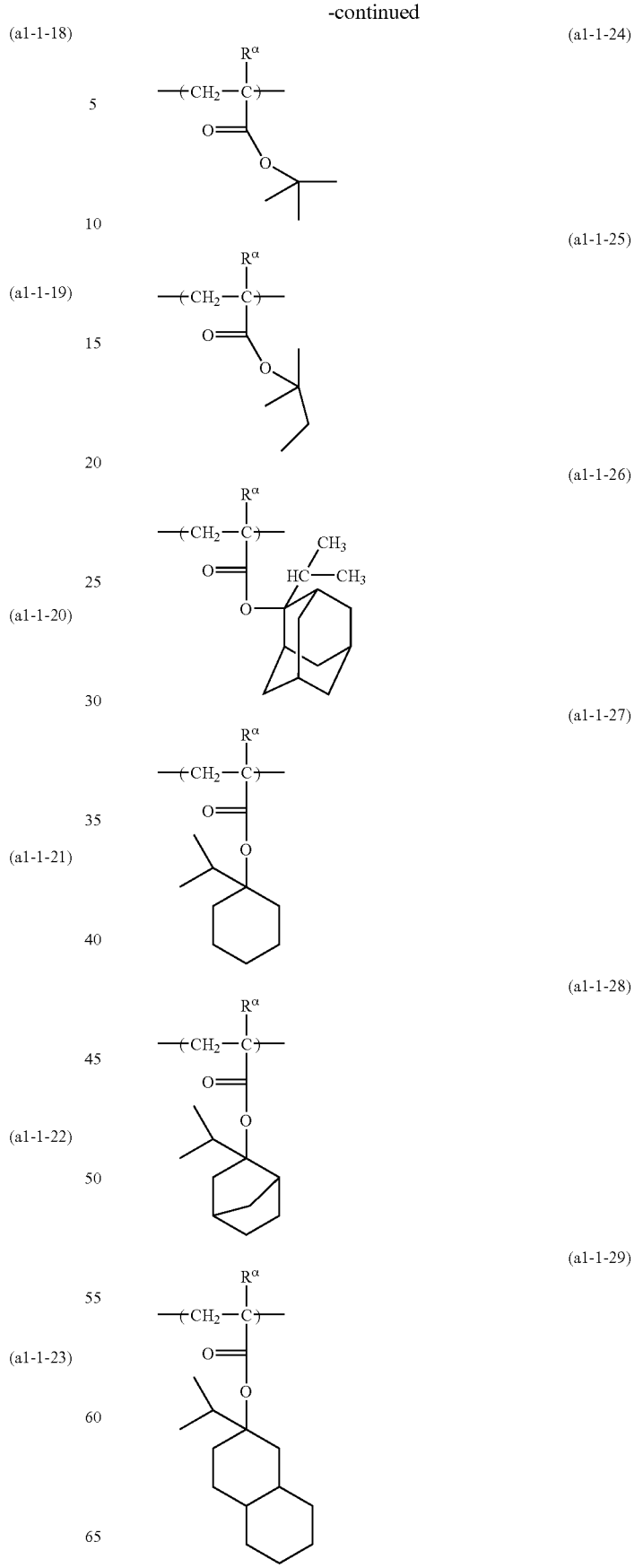

(a1-1-30)
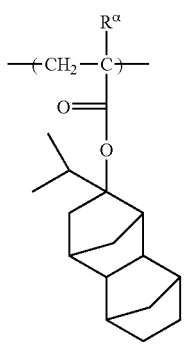
(a1-1-31)
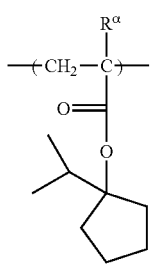
[Chemical Formula 13]
(a1-2-1)
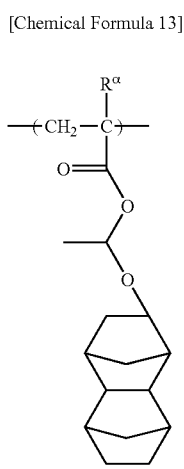
(a1-2-2)
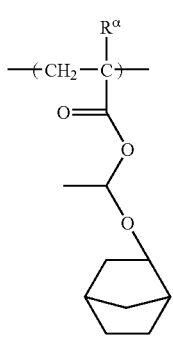
(a1-2-3)
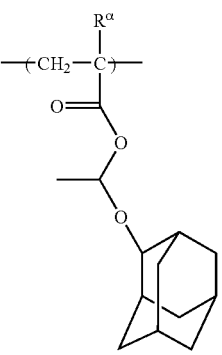
(a1-2-4)
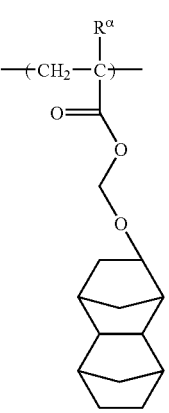
(a1-2-5)
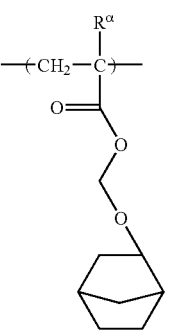
(a1-2-6)
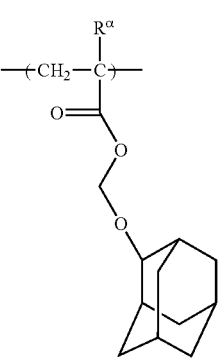

(a1-2-7)
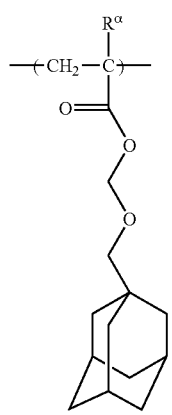
(a1-2-8)
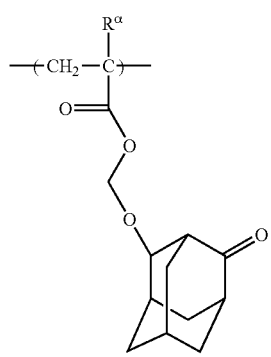
(a1-2-9)
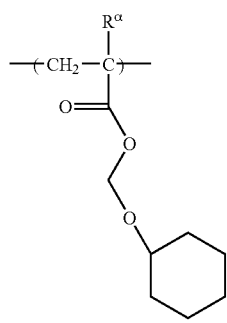
(a1-2-10)
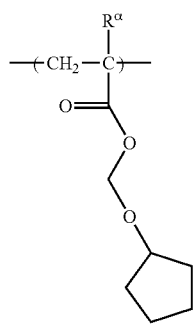
(a1-2-11)
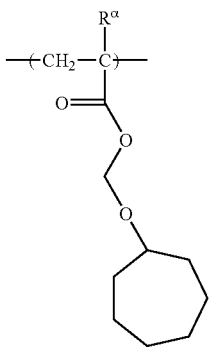
(a1-2-12)
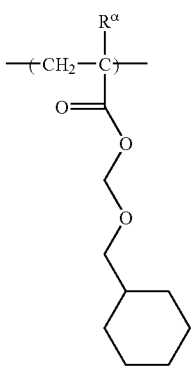
(a1-2-13)
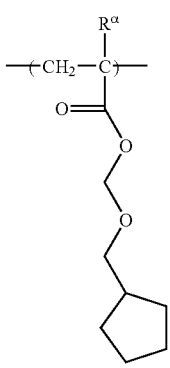
(a1-2-14)
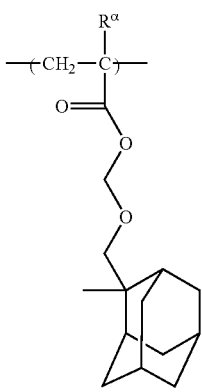

(a1-2-15) 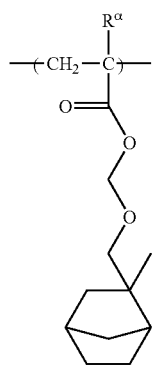
(a1-2-16) 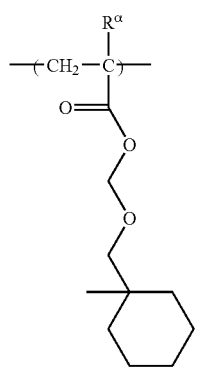
(a1-2-17) 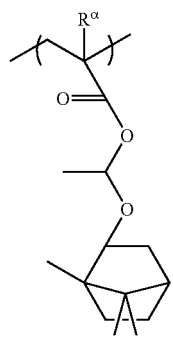
(a1-2-18) 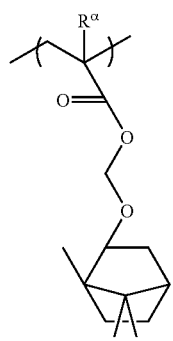
(a1-2-19) 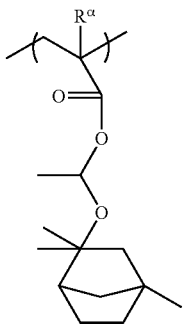
(a1-2-20) 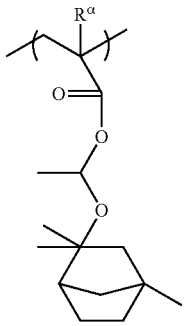
(a1-2-21) 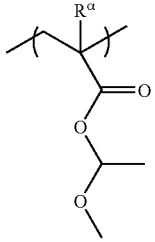
(a1-2-22) 
(a1-2-22) 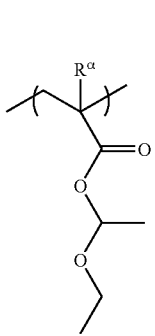

(a1-2-23)
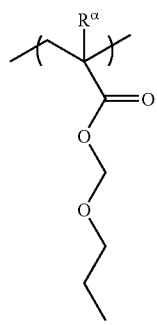
[Chemical Formula 14]
(a1-3-1)
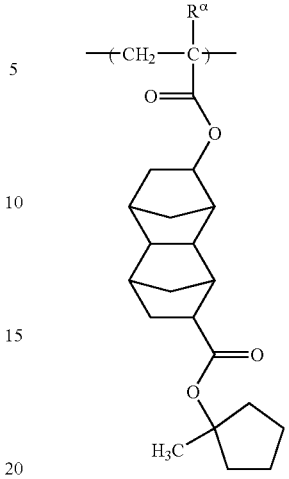
(a1-3-2)
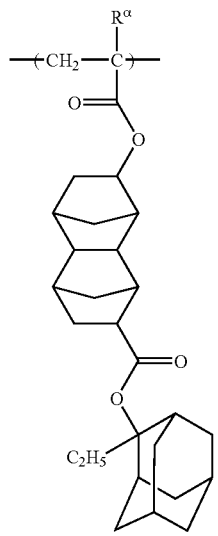
(a1-3-3)
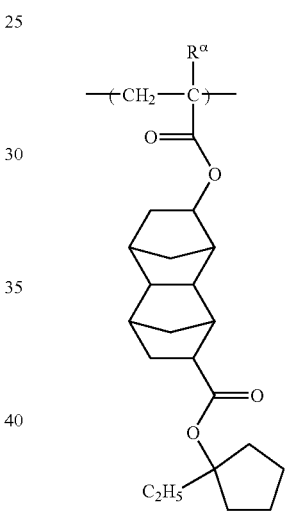
(a1-3-4)
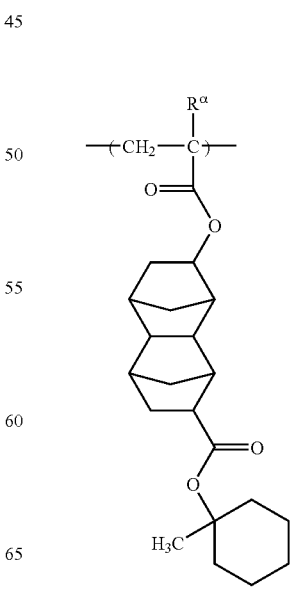
(a1-3-5)

(a1-3-6)
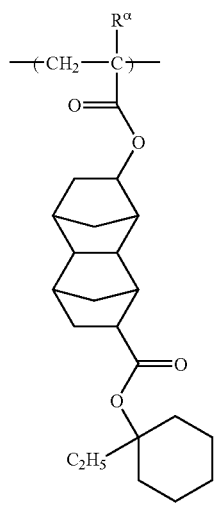
(a1-3-7)
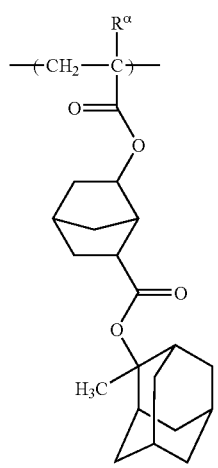
(a1-3-8)
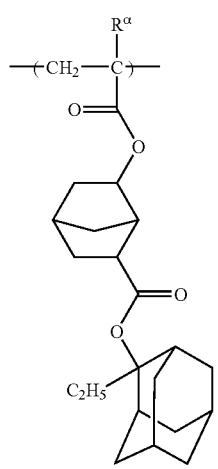
(a1-3-9)
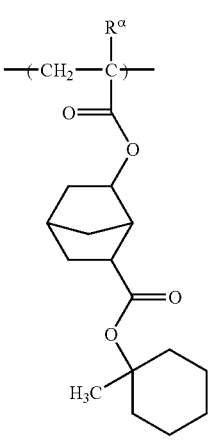
(a1-3-10)
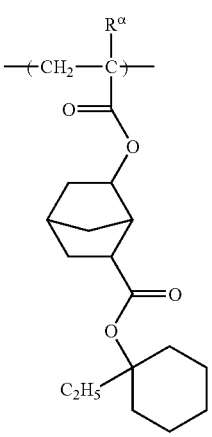
(a1-3-11)
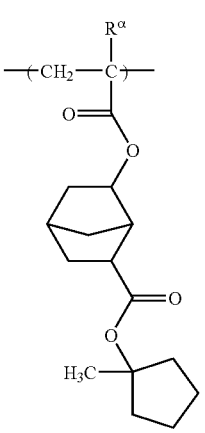

(a1-3-12)
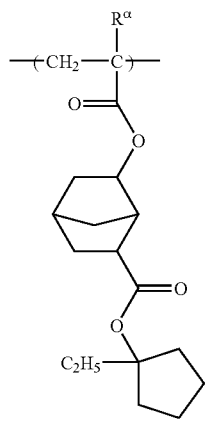
(a1-3-13)
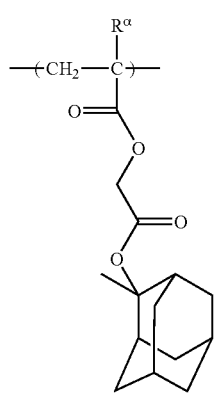
(a1-3-14)
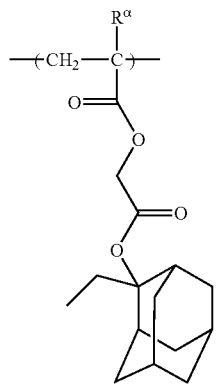
(a1-3-15)
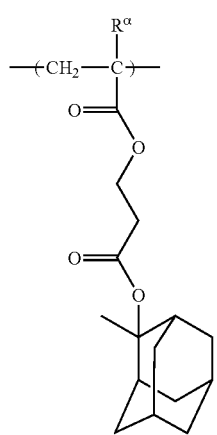
(a1-3-16)
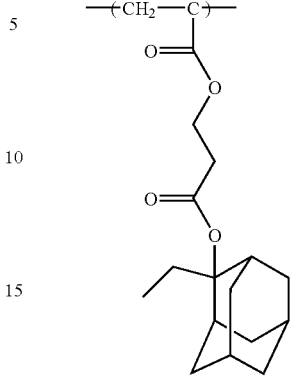
(a1-3-17)
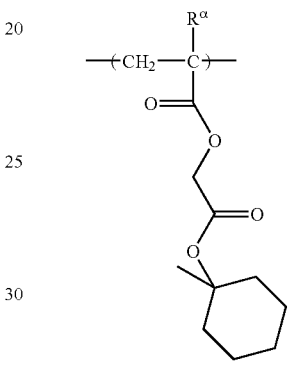
(a1-3-18)
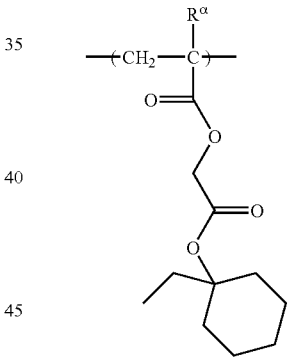
[Chemical Formula 15]
(a1-3-19)
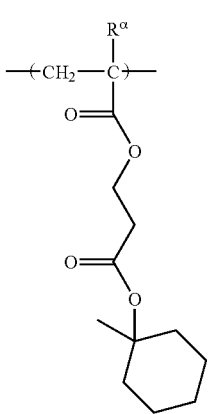

(a1-3-20)
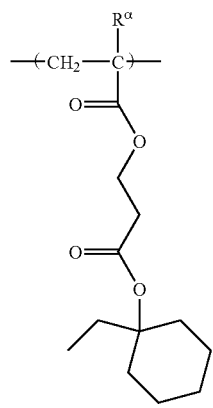
(a1-3-21)
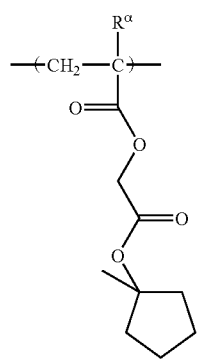
(a1-3-22)
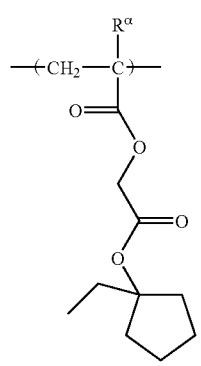
(a1-3-23)
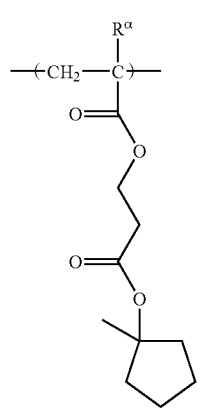
(a1-3-24)
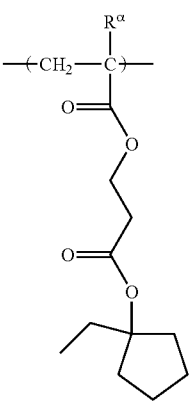
[Chemical Formula 16]
(a1-3-25)
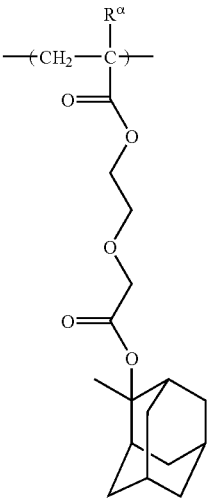
(a1-3-26)
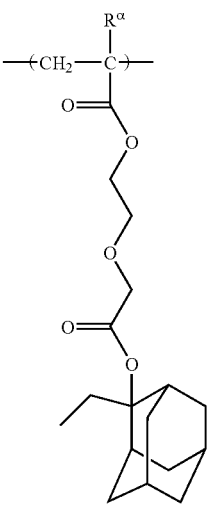

(a1-3-27)
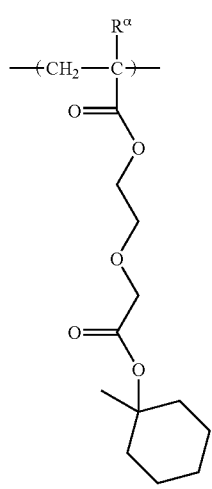
(a1-3-28)
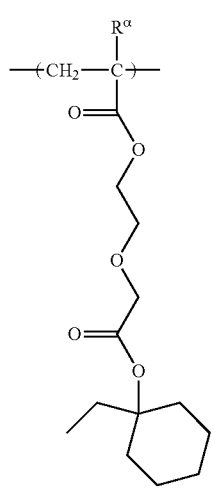
[Chemical Formula 17]
(a1-3-29)
(a1-3-30)
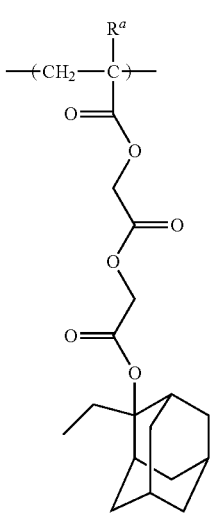
[Chemical Formula 18]
(a1-4-1)
(a1-4-2)
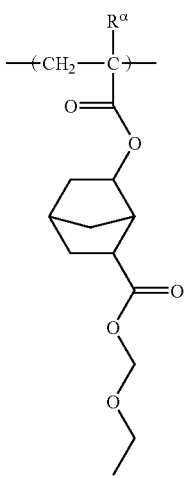

(a1-4-3) 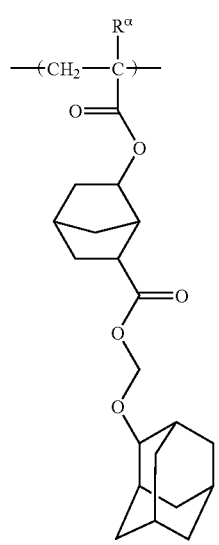
(a1-4-4) 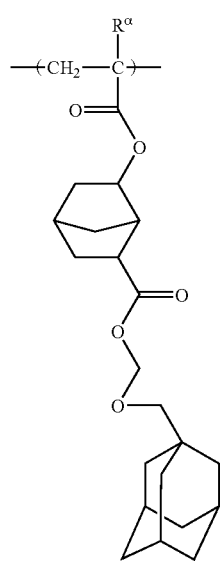
(a1-4-5) 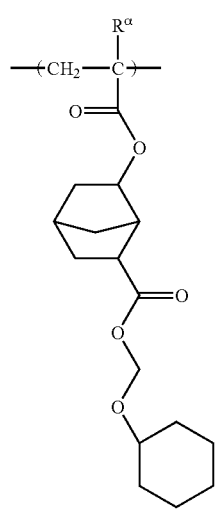
(a1-4-6) 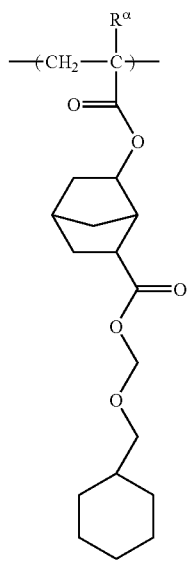
(a1-4-7) 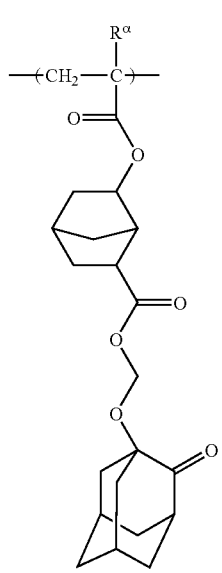
(a1-4-8) 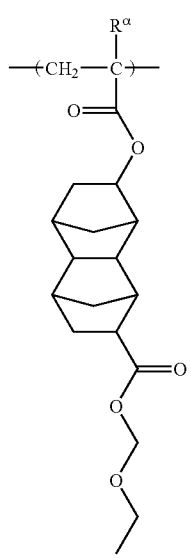

(a1-4-9)
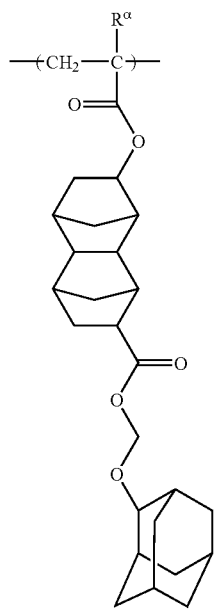
(a1-4-10)
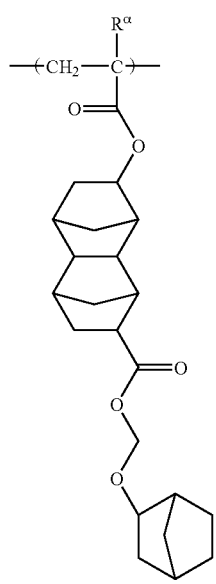
(a1-4-11)
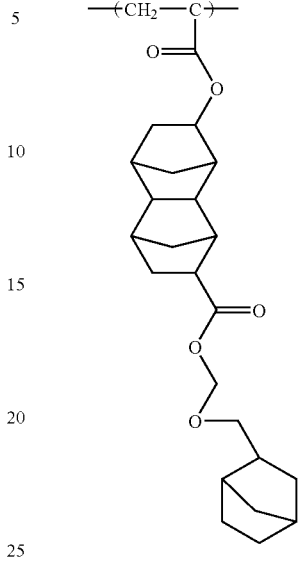
(a1-4-12)
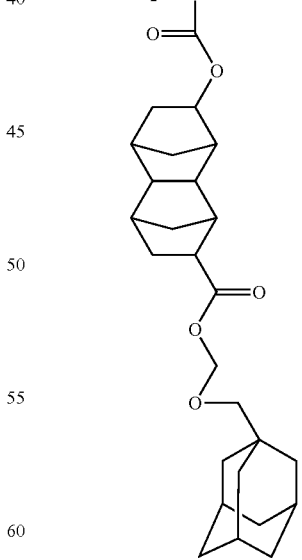

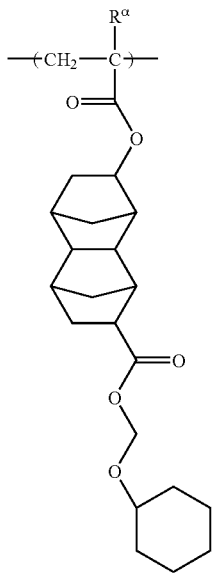

(a1-4-13)

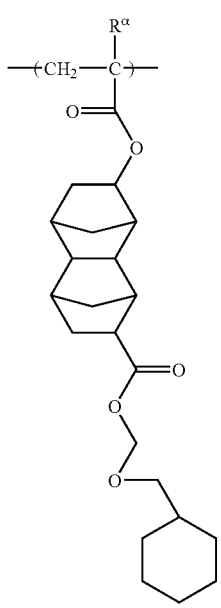

(a1-4-14)

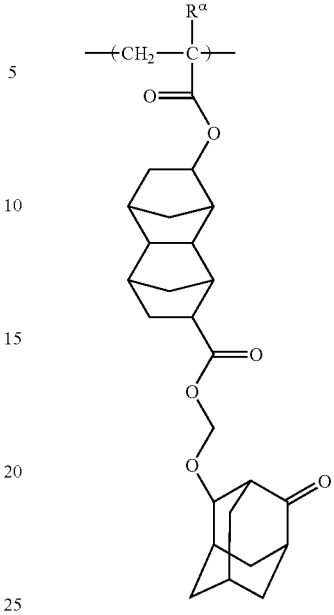

(a1-4-15)

In the above formulas, $R^\alpha$ represents a hydrogen atom, a methyl group or a trifluoromethyl group.

As the structural unit (a1), one type of structural unit may be used alone, or two or more types of structural units may be used in combination.

Among the above units, structural units represented by general formula (a1-1) or (a1-3) are preferable. More specifically, at least one structural unit selected from the group consisting of structural units represented by formulas (a1-1-1) to (a-1-1-3), (a1-1-20) to (a1-1-23) and (a1-3-25) to (a1-3-30) is more preferable.

Further, as the structural unit (a1), structural units represented by general formula (a1-1-01) shown below, which includes the structural units represented by formulas (a1-1-1) to (a1-1-3), structural units represented by general formula (a1-1-02) shown below, which includes the structural units represented by formulas (a1-1-16) to (a1-1-17) and formulas (a1-1-20) to (a1-1-23), structural units represented by general formula (a1-3-01) shown below, which includes the structural units represented by formulas (a1-3-25) to (a1-3-26), structural units represented by general formula (a1-3-02) shown below, which includes the structural units represented by formulas (a1-3-27) to (a1-3-28), and structural units represented by general formula (a1-3-03) shown below, which includes the structural units represented by formulas (a1-3-29) to (a1-3-30), are also preferable.

[Chemical Formula 19]

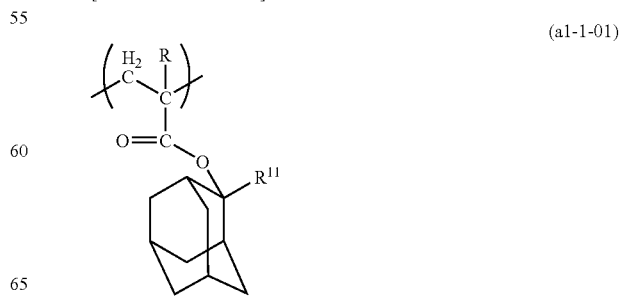

(a1-1-01)

wherein R represents a hydrogen atom, a lower alkyl group or a halogenated lower alkyl group; and $R^{11}$ represents a lower alkyl group.

[Chemical Formula 20]

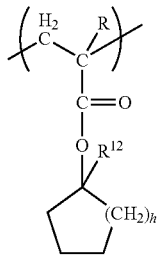

(a1-1-02)

wherein R represents a hydrogen atom, a lower alkyl group or a halogenated lower alkyl group; $R^{12}$ represents a lower alkyl group; and h represents an integer of 1 to 6.

In general formula (a1-1-01), R is as defined for R in general formula (a1-0-1) above. The lower alkyl group for $R^{11}$ is the same as the lower alkyl group for R above, and is preferably a methyl group or an ethyl group.

In general formula (a1-1-02), R is as defined for R in general formula (a1-0-1) above. The lower alkyl group for $R^{12}$ is the same as the lower alkyl group for R above. $R^{12}$ is preferably a methyl group or an ethyl group, and most preferably an ethyl group. h is preferably 1 or 2.

[Chemical Formula 21]

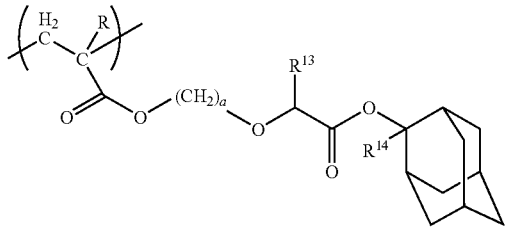

(a1-3-01)

wherein R represents a hydrogen atom, a lower alkyl group or a halogenated lower alkyl group; $R^{14}$ represents a lower alkyl group; $R^{13}$ represents a hydrogen atom or a methyl group; and a represents an integer of 1 to 10.

[Chemical Formula 22]

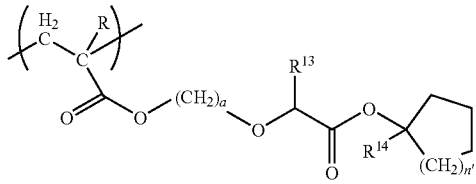

(a1-3-02)

wherein R represents a hydrogen atom, a lower alkyl group or a halogenated lower alkyl group; $R^{14}$ represents a lower alkyl group; $R^{13}$ represents a hydrogen atom or a methyl group; a represents an integer of 1 to 10; and n' represents an integer of 1 to 6.

[Chemical Formula 23]

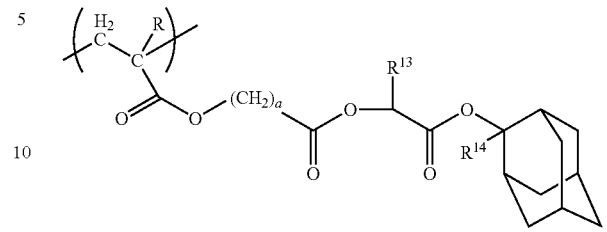

(a1-3-03)

wherein R represents a hydrogen atom, a lower alkyl group or a halogenated lower alkyl group; $R^{14}$ represents a lower alkyl group; $R^{13}$ represents a hydrogen atom or a methyl group; and a represents an integer of 1 to 10.

In the aforementioned general formulas (a1-3-01) to (a1-3-03), R is as defined for R in general formula (a1-3) above.

$R^{13}$ is preferably a hydrogen atom.

The lower alkyl group for $R^{14}$ is the same as the lower alkyl group for R, and is preferably a methyl group or an ethyl group.

In the aforementioned general formula (a1-3-01) or (a1-3-02), a is preferably an integer of 1 to 8, more preferably an integer of 2 to 5, and most preferably 2.

In the aforementioned general formula (a1-3-03), a is preferably an integer of 1 to 8, more preferably an integer of 1 to 5, and most preferably 1.

In the copolymer (A1-1), the amount of the structural unit (a1) based on the combined total of all structural units constituting the copolymer (A1-1) is preferably 10 to 80 mol %, more preferably 20 to 70 mol %, and still more preferably 25 to 50 mol %. By making the amount of the structural unit (a1) at least as large as the lower limit of the above-mentioned range, a pattern can be easily formed using a resist composition prepared from the copolymer (A1-1). On the other hand, by making the amount of the structural unit (a1) no more than the upper limit of the above-mentioned range, a good balance can be achieved with the other structural units.

In the component (A1), the amount of the structural unit represented by general formula (a1-1-01) or (a1-1-02) based on the combined total of all structural units constituting the component (A1) is preferably 10 to 80 mol %, more preferably 15 to 70 mol %, and still more preferably 15 to 50 mol %. By making the amount of the structural unit represented by general formula (a1-1-01) or (a1-1-02) at least as large as the lower limit of the above-mentioned range, a pattern can be easily formed using a resist composition prepared from the component (A1). On the other hand, by making the amount of the structural unit represented by general formula (a1-1-01) or (a1-1-02) no more than the upper limit of the above-mentioned range, a good balance can be achieved with the other structural units.

In the component (A1), the amount of the structural units represented by general formulas (a1-3-01) to (a1-3-03) based on the combined total of all structural units constituting the component (A1) is preferably 5 to 50 mol %, more preferably 5 to 30 mol %, and still more preferably 5 to 25 mol %. By making the amount of the structural units represented by general formulas (a1-3-01) to (a1-3-03) at least as large as the lower limit of the above-mentioned range, a pattern can be easily formed using a resist composition prepared from the component (A1). On the other hand, by making the amount of the structural units represented by general formulas (a1-3-01)

to (a1-3-03) no more than the upper limit of the above-mentioned range, a good balance can be achieved with the other structural units.

The monomers for deriving the structural units represented by general formulas (a1-3-01) to (a1-3-03) above (hereafter, these monomers are collectively referred to as "monomers W") can be produced, for example, by the production method shown below.

Production Method of Monomer W:

A compound represented by general formula (X-2) shown below (hereafter, referred to as "compound (X-2)") is added to a compound represented by general formula (X-1) shown below (hereafter, referred to as "compound (X-1)") dissolved in a reaction solvent, in the presence of a base, and a reaction is effected to obtain a compound represented by general formula (X-3) shown below (hereafter, referred to as "compound (X-3)"). Then, a compound represented by general formula (X-4) shown below is added to the resulting solution having the compound (X-3) dissolved therein, in the presence of a base, and a reaction is effected to thereby obtain a monomer W.

The compound (X-2) can be obtained, for, example, by reacting a compound represented by formula $X^{11}$—B—C(=O)—OH and a compound represented by formula $X^2$—H. Alternatively, instead of the compound (X-2), each of the compounds represented by formulas $X^{11}$—B—C(=O)—OH and $X^2$—H may be used separately.

Examples of the base include inorganic bases such as sodium hydride, $K_2CO_3$ and $Cs_2CO_3$, and organic bases such as triethylamine, 4-dimethylaminopyridine (DMAP) and pyridine.

As the reaction solvent, any reaction solvent capable of dissolving a compound (X-1) and a compound (X-2) (which are raw materials) can be used, and specific examples include tetrahydrofuran (THF), acetone, dimethylformamide (DMF), dimethylacetamide, dimethyl sulfoxide (DMSO) and acetonitrile.

[Chemical Formula 24]

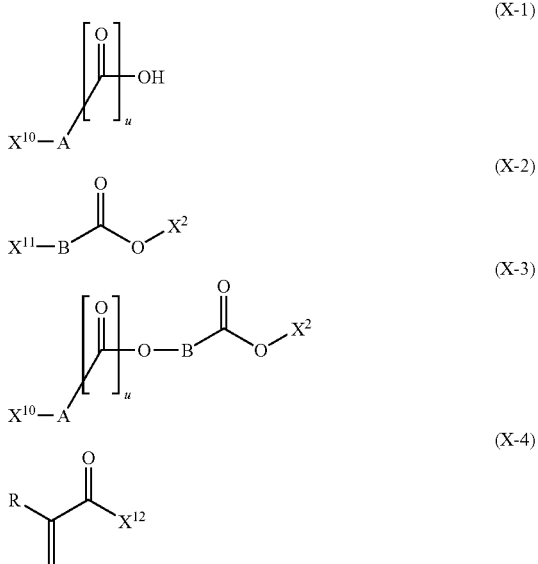

wherein R represents a hydrogen atom, a lower alkyl group or a halogenated lower alkyl group; each of A and B independently represents a divalent hydrocarbon group which may have a substituent; $X^2$ represents an acid dissociable, dissolution inhibiting group; each of $X^{10}$ and $X^{12}$ independently represents a hydroxyl group or a halogen atom, with the proviso that either one of $X^{10}$ and $X^{12}$ represents a hydroxyl group and the other represents a halogen atom; $X^{11}$ represents a halogen atom; and u represents 0 or 1.

In the aforementioned formulas, R, $X^2$, A and B are as defined above.

Examples of halogen atoms for $X^{10}$, $X^{11}$ and $X^{12}$ include a bromine atom, a chlorine atom, an iodine atom and a fluorine atom.

As the halogen atom for $X^{10}$ or $X^{12}$, a chlorine atom and a bromine atom are preferred as these atoms offer superior reactivity.

As $X^{11}$, a bromine atom or a chlorine atom is preferred as these atoms offer superior reactivity.

The above-mentioned production method of monomer W shows a method for producing monomers for deriving the structural units represented by general formulas (a1-3-01) and (a1-3-02) above when u=0, and shows a method for producing monomers for deriving the structural unit represented by general formula (a1-3-03) above when u=1.

—Structural Unit (a2)

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the copolymer (A1-1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include groups in which one hydrogen atom has been removed from a monocyclic lactone such as γ-butyrolactone or mevalonic lactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below

[Chemical Formula 25]

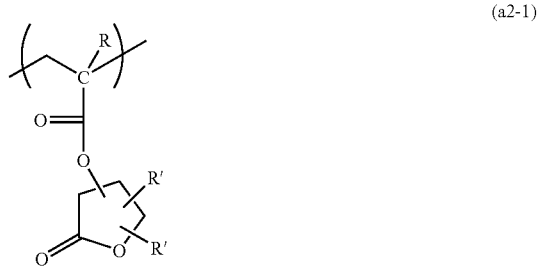

-continued

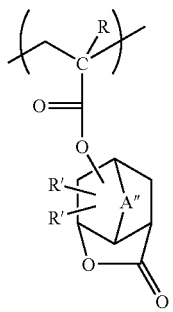 (a2-2)

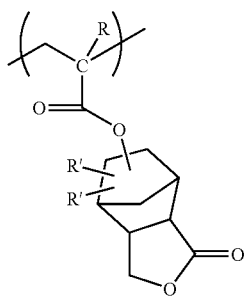 (a2-3)

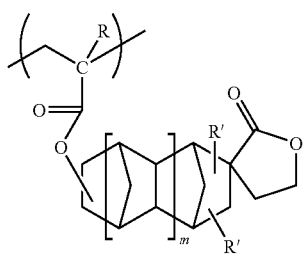 (a2-4)

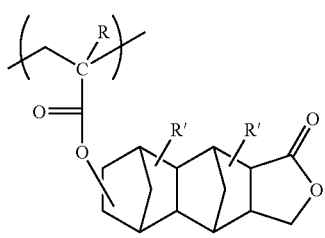 (a2-5)

wherein R represents a hydrogen atom, a lower alkyl group or a halogenated lower alkyl group; R' represents a hydrogen atom, a lower alkyl group, an alkoxy group of 1 to 5 carbon atoms or —COOR", wherein R" represents a hydrogen atom or a linear, branched or cyclic alkyl group of 1 to 15 carbon atoms; m represents an integer of 0 or 1; and A" represents an alkylene group of 1 to 5 carbon atoms which may contain an oxygen atom or a sulfur atom, an oxygen atom or a sulfur atom.

In general formulas (a2-1) to (a2-5), R is the same as R in the structural unit (a1).

The lower alkyl group for R' is the same as the lower alkyl group for R in the structural unit (a1).

When R" is a linear or branched alkyl group, it preferably has 1 to 10 carbon atoms, and more preferably 1 to 5 carbon atoms.

When R" is a cyclic alkyl group, it preferably has 3 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, and which may or may not be substituted with fluorine atoms or fluorinated alkyl groups. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

In the structural units represented by general formulas (a2-1) to (a2-5), in consideration of industrial availability, R' is preferably a hydrogen atom.

Specific examples of alkylene groups of 1 to 5 carbon atoms which may contain an oxygen atom or a sulfur atom for A" include a methylene group, ethylene group, n-propylene group, isopropylene group, —O—$CH_2$—, —$CH_2$—O—$CH_2$—, —S—$CH_2$— and —$CH_2$—S—$CH_2$—.

Specific examples of structural units represented by general formulas (a2-1) to (a2-5) above are shown below.

[Chemical Formula 26]

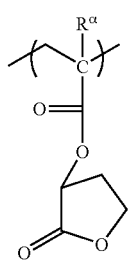 (a2-1-1)

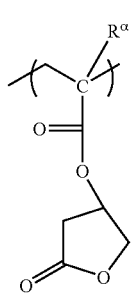 (a2-1-2)

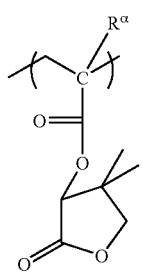 (a2-1-3)

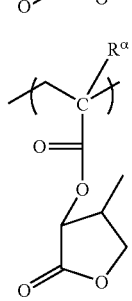 (a2-1-4)

[Chemical formula 27]
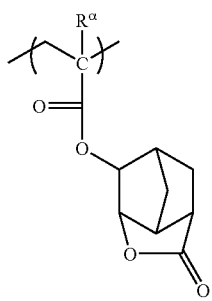 (a2-2-1)
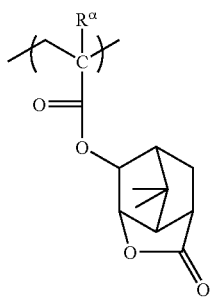 (a2-2-2)
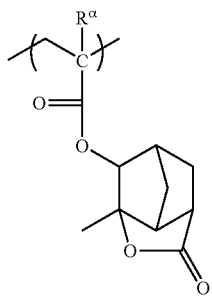 (a2-2-3)
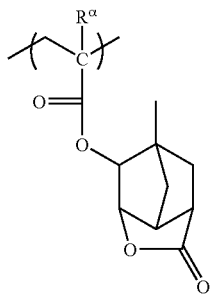 (a2-2-4)
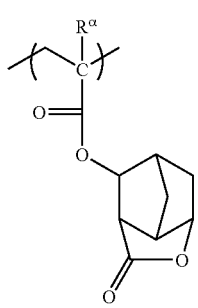 (a2-2-5)
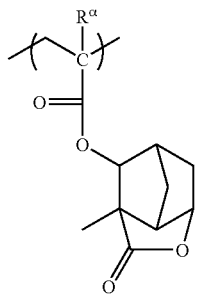 (a2-2-6)
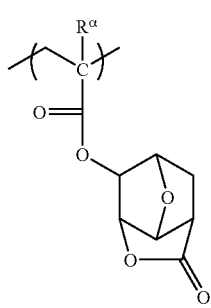 (a2-2-7)
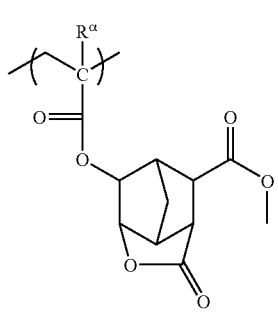 (a2-2-8)
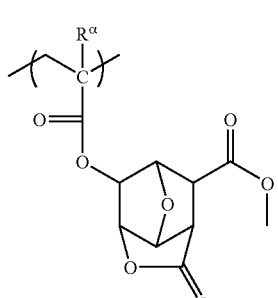 (a2-2-9)
[Chemical Formula 28]
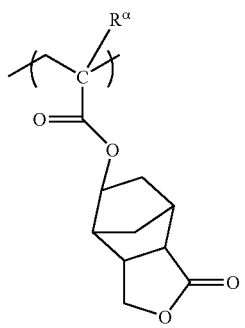 (a2-3-1)

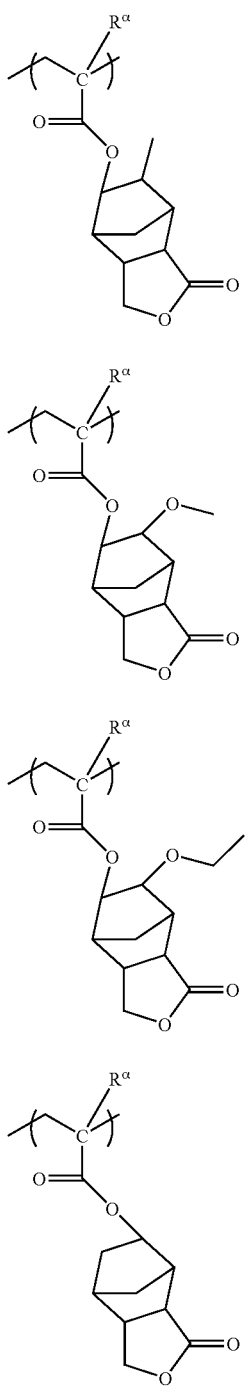
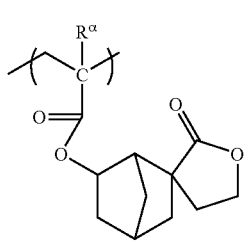
[Chemical Formula 29]
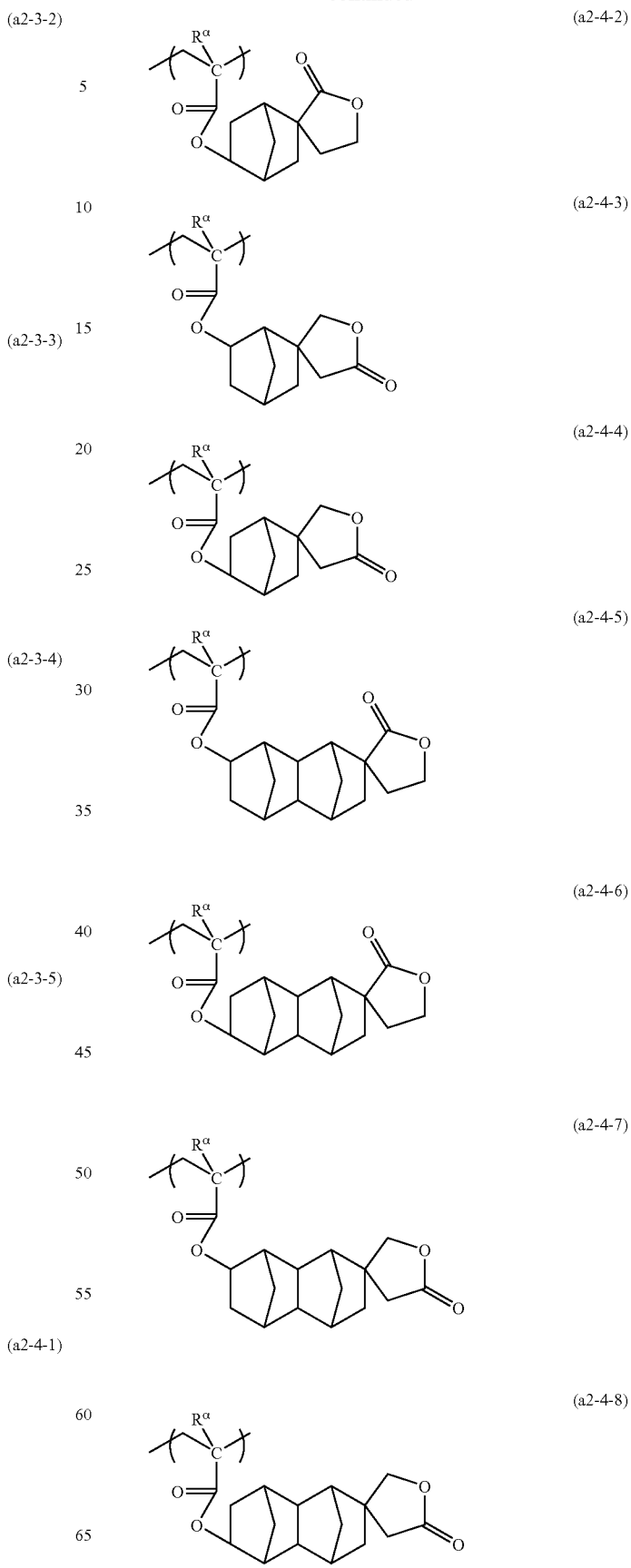

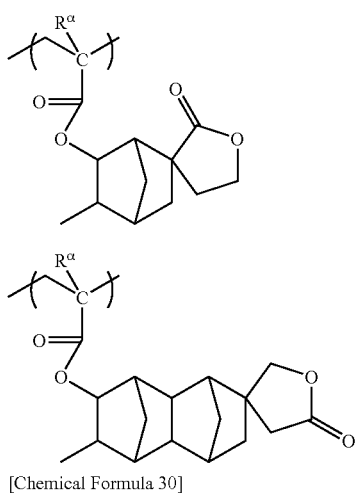

(a2-4-9)

(a2-4-10)

[Chemical Formula 30]

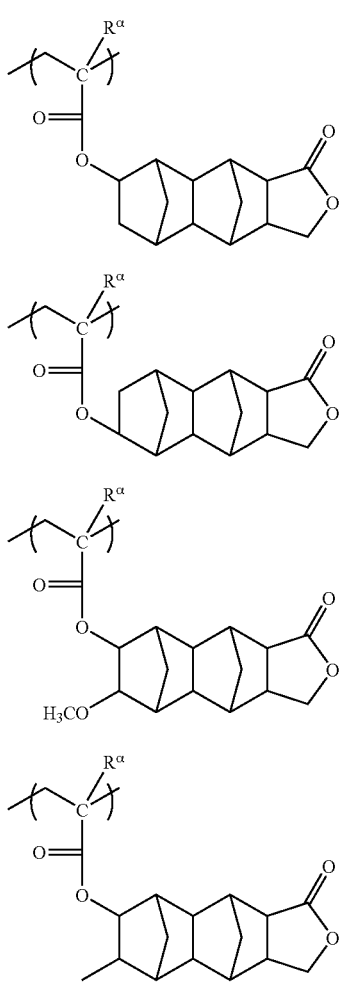

(a2-5-1)

(a2-5-2)

(a2-5-3)

(a2-5-4)

In the above formulas, Rα represents a hydrogen atom, a methyl group or a trifluoromethyl group.

In the copolymer (A1-1), as the structural unit (a2), one type of structural unit may be used alone, or two or more types of structural units may be used in combination.

As the structural unit (a2), at least one structural unit selected from the group consisting of structural units represented by formulas (a2-1) to (a2-5) is preferable, and at least one structural unit selected from the group consisting of structural units represented by formulas (a2-1) to (a2-3) is more preferable. Of these, it is particularly desirable to use at least one structural unit selected from the group consisting of structural units represented by chemical formulas (a2-1-1), (a2-2-1), (a2-2-7), (a2-3-1) and (a2-3-5).

In the copolymer (A1-1), the amount of the structural unit (a2) based on the combined total of all structural units constituting the copolymer (A1-1) is preferably 5 to 70 mol %, more preferably 10 to 65 mol %, and still more preferably 20 to 60 mol %. By making the amount of the structural unit (a2) at least as large as the lower limit of the above-mentioned range, the effect of using the structural unit (a2) can be satisfactorily achieved. On the other hand, by making the amount of the structural unit (a2) no more than the upper limit of the above-mentioned range, a good balance can be achieved with the other structural units.

—Structural Unit (a3)

The structural unit (a3) is a structural unit derived from an acrylate ester containing a polar group-containing aliphatic hydrocarbon group.

When the copolymer (A1-1) includes the structural unit (a3), the hydrophilicity of the component (A) is improved, and hence, the compatibility of the component (A) with the developing solution is improved. As a result, the alkali solubility of the exposed portions improves, which contributes to favorable improvements in the resolution.

Examples of the polar group include a hydroxyl group, a cyano group, a carboxyl group, or a hydroxyalkyl group in which a part of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that includes an aliphatic polycyclic group containing a hydroxyl group, cyano group, carboxyl group or a hydroxyalkyl group in which some of the hydrogen atoms of the alkyl group have been substituted with fluorine atoms are particularly desirable. Examples of the polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, groups in which two or more hydrogen atoms have been removed from norbornane, and groups in which two or more hydrogen atoms have been removed from tetracyclododecane are preferred industrially.

When the hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, preferable

[Chemical Formula 31]

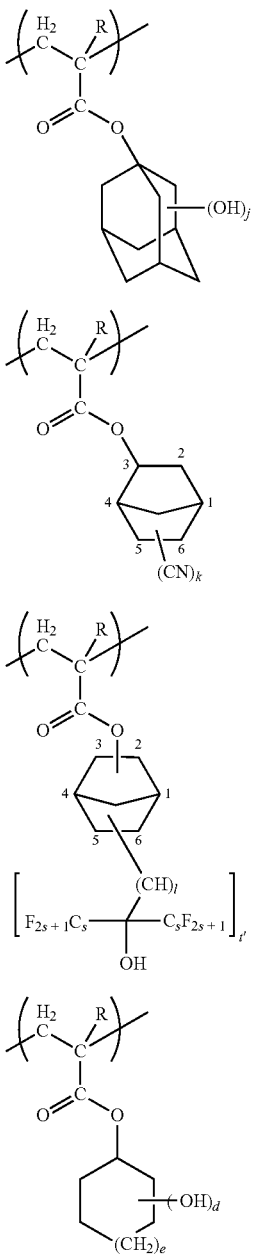

(a3-1)

(a3-2)

(a3-3)

(a3-4)

wherein R represents a hydrogen atom, a lower alkyl group or a halogenated lower alkyl group; j represents an integer of 1 to 3; k represents an integer of 1 to 3; t' represents an integer of 1 to 3; l represents an integer of 1 to 5; s represents an integer of 1 to 3; d represents an integer of 1 to 3; and e represents 0 or 1.

In general formulas (a3-1) to (a3-4), the lower alkyl group and halogenated lower alkyl group for R are the same as the lower alkyl group and halogenated lower alkyl group which can be bonded to the α-position of the aforementioned acrylate ester.

In general formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1, l is preferably 1 and s is preferably 1. Further, it is preferable that a 2-norbornyl group or 3-norbornyl group be bonded to the Further, it is preferable that a 2-norbornyl group or 3-norbornyl group be bonded to the terminal of the carboxyl group of the acrylic acid. The fluorinated alkyl alcohol $(-(CH_2)_l-C(C_s F_{2s+1})_2-OH)$ is preferably bonded to the 5th or 6th position of the norbornyl group.

In formula (a3-4), d is preferably 1 or 2, and more preferably 1. Although there are no particular limitations on the bonding position of the hydroxyl group, when d is 1, the bonding position of the hydroxyl group is preferably the 2nd position in terms of availability and low cost. When d is 2 or 3, any combination of the substitution positions is suitable.

As the structural unit (a3), one type of structural unit may be used alone, or two or more types of structural units may be used in combination.

In the copolymer (A1-1), the amount of the structural unit (a3) based on the combined total of all structural units constituting the copolymer (A1-1) is preferably 5 to 50 mol %, more preferably 5 to 40 mol %, and still more preferably 5 to 25 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

—Structural Unit (a4)

The copolymer (A1-1) may also have a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), for example, a structural unit derived from an acrylate ester that contains a non-acid-dissociable aliphatic polycyclic group is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 32]

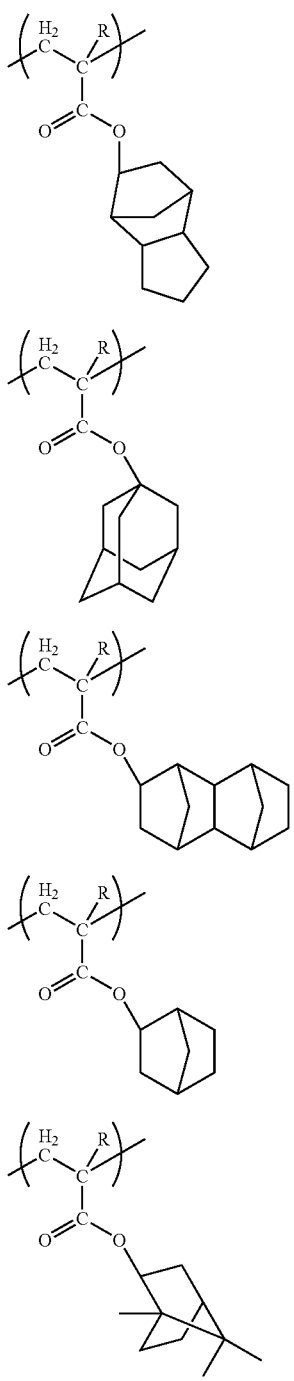

(a4-1)
(a4-2)
(a4-3)
(a4-4)
(a4-5)

wherein R represents a hydrogen atom, a lower alkyl group or a halogenated lower alkyl group.

In general formulas (a4-1) to (a4-5) above, the lower alkyl group and halogenated lower alkyl group for R are the same as the lower alkyl group and halogenated lower alkyl group which may be bonded to the α-position of the aforementioned acrylate ester.

When the structural unit (a4) is included in the copolymer (A1-1), the amount of the structural unit (a4) based on the combined total of all the structural units that constitute the component (A1) is preferably within the range from 1 to 30 mol %, and more preferably from 10 to 20 mol %.

In the present invention, the copolymer (A1-1) is preferably a copolymer having the structural units (a1), (a2) and (a3). Examples of such a copolymer include a copolymer formed from the structural units (a1) and (a2) and (a3), and a copolymer formed from the structural units (a1), (a2), (a3) and (a4).

In the component (A), as the copolymer (A1-1), one type of copolymer may be used alone, or two or more types may be used in combination.

In the present invention, it is particularly desirable that the copolymer (A1-1) include a combination of structural units such as that shown below.

[Chemical Formula 33]

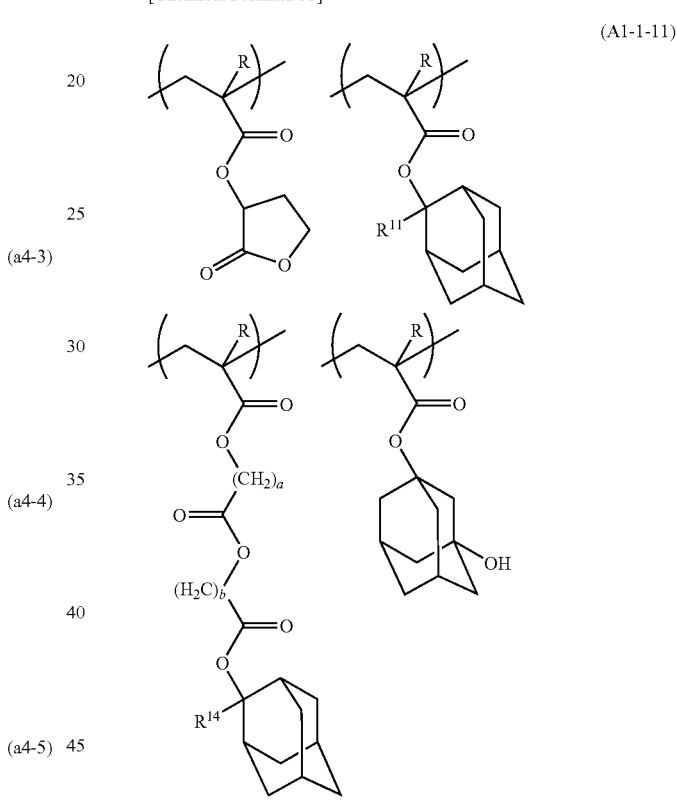

(A1-1-11)

In the above-mentioned general formula (a1-1-11), R is as defined above, and the plurality of R may be either the same or different from each other. $R^{11}$, $R^{14}$ and a are the same as defined above, and b represents an integer of 1 to 10.

In the above formula (A1-1-11), the lower alkyl group for $R^{11}$ is most preferably an ethyl group.

The lower alkyl group for $R^{14}$ is preferably a methyl group or an ethyl group, and most preferably a methyl group.

a represents an integer of 1 to 10, is preferably 1 or 2, and is most preferably 1.

b represents an integer of 1 to 10, is preferably 1 or 2, and is most preferably 1.

The copolymer (A1-1) can be obtained, for example, by a conventional radical polymerization or the like of the monomers corresponding with each of the structural units, using a radical polymerization initiator such as azobisisobutyronitrile (AIBN) and dimethyl azobisisobutyrate.

Furthermore, in the component (A1), by using a chain transfer agent such as HS—$CH_2$—$CH_2$—$CH_2$—$C(CF_3)_2$—

OH during the polymerization, a —C(CF$_3$)$_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the copolymer (A1-1) is not particularly limited, but is preferably 2,000 to 50,000, more preferably 3,000 to 30,000, and most preferably 5,000 to 20,000. By ensuring that the weight average molecular weight is no more than the upper limit of the above-mentioned range, the copolymer (A1-1) exhibits satisfactory solubility in a resist solvent when used as a resist. On the other hand, by ensuring that the weight average molecular weight is at least as large as the lower limit of the above-mentioned range, the dry etching resistance and cross-sectional shape of the resist pattern become satisfactory.

Further, the dispersity (Mw/Mn) is preferably 1.0 to 5.0, more preferably 1.0 to 3.0, and most preferably 1.2 to 2.5. Here, Mn is the number average molecular weight.

[Component (A1-2)]

As the component (A1-2), a low molecular compound is preferable, which has a molecular weight of at least 500 and less than 2,000, and contains an acid dissociable, dissolution inhibiting group exemplified above in connection with the copolymer (A1-1) and a hydrophilic group. Specific examples include compounds containing a plurality of phenol skeletons in which a part of the hydrogen atoms within hydroxyl groups have been substituted with the aforementioned acid dissociable, dissolution inhibiting groups.

Preferred examples of the component (A1-2) include low molecular weight phenolic compounds that are known, for example, as sensitizers or heat resistance improvers for use in non-chemically amplified g-line or i-line resists, wherein some of the hydrogen atoms within the hydroxyl group of these compounds have been substituted with the acid dissociable, dissolution inhibiting groups exemplified above, and any of these compounds may be used.

Examples of these low molecular weight phenolic compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. It goes without saying that the low molecular weight phenolic compound is not limited to these examples.

Also, there are no particular limitations on the acid dissociable, dissolution inhibiting group, and suitable examples include the groups described above.

In the component (A), as the component (A1-2), one type may be used alone, or two or more types may be used in combination.

As the component (A1), one type may be used alone, or two or more types may be used in combination.

Of the various possibilities described above, the component (A1) preferably includes the copolymer (A1-1).

In the resist composition of the present invention, the amount of the component (A) can be appropriately adjusted depending on the thickness of the resist film to be formed, and the like.

<Component (A2)>
[Copolymer (A2-1)]
—Structural Unit (a1')

The component (A2) preferably includes a structural unit (a1') that contains, within the main chain, an aliphatic cyclic group having a fluorinated hydroxyalkyl group as described earlier.

In the structural unit (a1'), the "aliphatic cyclic group having a fluorinated hydroxyalkyl group" refers to a group in which a fluorinated hydroxyalkyl group is bonded to a carbon atom that constitutes part of a ring of an aliphatic cyclic group.

Furthermore, the description of the aliphatic cyclic group as being "within the main chain" means that at least one, and preferably two or more carbon atoms within the ring structure of the aliphatic cyclic group constitute part of the main chain of the copolymer (A2-1).

In the present invention, by including the copolymer (A2-1) that contains the structural unit (a1'), the solubility of the component (A2) within an alkali developing solution enhances, and lithographic properties such as the resist pattern shape and line width roughness (LWR) may also be improved. Further, because the structural unit (a1') includes the aliphatic cyclic group (such as a norbornane or tetracyclododecane structure) within the main chain, the carbon density is increased, yielding an improvement in the etching resistance.

Here, a "fluorinated hydroxyalkyl group" refers to a hydroxyalkyl group, in which a portion of the hydrogen atoms of an alkyl group have been substituted with hydroxyl groups, wherein some or all of the remaining hydrogen atoms within the hydroxyalkyl group have been substituted with fluorine atoms.

In a fluorinated hydroxyalkyl group, the fluorination increases the ease with which the hydrogen atom of the hydroxyl group is released.

In the fluorinated hydroxyalkyl group, the alkyl group is preferably a linear or branched alkyl group.

Although there are no particular limitations on the number of carbon atoms within the alkyl group, the number of carbon atoms is preferably from 1 to 20, more preferably from 4 to 16, and most preferably from 4 to 12.

There are no particular limitations on the number of hydroxyl groups within the fluorinated hydroxyalkyl group, although a single hydroxyl group is preferred.

Of the various possibilities, groups in which a fluorinated alkyl group and/or a fluorine atom is bonded to the carbon atom to which the hydroxyl group is bonded (which refers to the α-position carbon atom of the hydroxyalkyl group) are preferred as the fluorinated hydroxyalkyl group.

Further, the fluorinated alkyl group bonded to the α-position is preferably a group in which all of the hydrogen atoms of the alkyl group have been substituted with fluorine atoms. Furthermore, as the alkyl group of this fluorinated alkyl group, a linear or branched alkyl group of 1 to 5 carbon atoms is preferred, and an alkyl group of one carbon atom is the most desirable.

The term "aliphatic" in the expression "aliphatic cyclic group having a fluorinated hydroxyalkyl group" is a relative concept used in relation to the term "aromatic", and defines a group or compound or the like that contains no aromaticity. The aliphatic cyclic group may be either monocyclic or polycyclic.

The expression "monocyclic aliphatic cyclic group" describes a monocyclic group that contains no aromaticity, whereas the expression "polycyclic aliphatic cyclic group" describes a polycyclic group that contains no aromaticity.

In the structural unit (a1'), the aliphatic cyclic group is preferably a polycyclic group, as such groups provide superior etching resistance and the like.

The aliphatic cyclic group includes both hydrocarbon groups formed solely from carbon and hydrogen (alicyclic groups), and heterocyclic groups in which a portion of the carbon atoms that constitute the ring structure of an alicyclic group have been substituted with a hetero atom such as an oxygen atom, nitrogen atom, or sulfur atom. These aliphatic cyclic groups may include substituent groups, and examples of these substituent groups include alkyl groups of 1 to 5 carbon atoms.

The expression "include substituent groups" means that some or all of the hydrogen atoms bonded to the carbon atoms that constitute the ring structure of the aliphatic cyclic group have been substituted with substituent groups (atoms or groups other than a hydrogen atom). In the present invention, an alicyclic group is preferred as the aliphatic cyclic group.

The aliphatic cyclic group may be either saturated or unsaturated, although a saturated group is preferred, as such groups exhibit superior transparency to ArF excimer lasers and the like, and also exhibit excellent resolution and depth of focus (DOF) and the like.

The number of carbon atoms within the aliphatic cyclic group is preferably within a range from 5 to 15.

Specific examples of the aliphatic cyclic group include the groups described below.

Examples of the monocyclic groups include groups in which two or more hydrogen atoms have been removed from a cycloalkane. Specific examples include groups in which two or more hydrogen atoms have been removed from cyclopentane or cyclohexane, and groups in which two or more hydrogen atoms have been removed from cyclohexane are preferred.

Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane.

These types of aliphatic cyclic groups can be selected appropriately from the multitude of groups that have been proposed for the resins of photoresist compositions used in ArF excimer laser processes.

Of the various possibilities, groups in which two or more hydrogen atoms have been removed from cyclohexane, adamantane, norbornane or tetracyclododecane are readily available industrially, and are consequently preferred.

Of the alicyclic groups described above, groups such as those shown in a structural unit (a1'-1) below, in which three hydrogen atoms have been removed from norbornane or tetracyclododecane, are preferred, and groups in which three hydrogen atoms have been removed from norbornane are particularly desirable.

Of the units included within the definition of the structural unit (a1'), structural unit (a1'-1) represented by general formula (a1'-1) shown below is preferred. Including the structural unit (a1'-1) particularly improves the solubility in an alkali developing solution. Furthermore, the lithography properties such as the resolution are also improved.

[Chemical Formula 34]

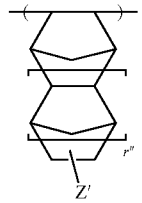

(a1'-1)

wherein Z' represents a fluorinated hydroxyalkyl group, and r" is either 0 or 1.

In formula (a1'-1), r" is either 0 or 1. In terms of industrial availability, r" is preferably 0.

Further, in formula (a1'-1), examples of the "fluorinated hydroxyalkyl group" represented by Z' include the same groups as those described above. Of these, Z' is preferably a group represented by general formula (a1'-1-1) shown below, as such groups yield a particularly superior resist pattern shape as well as reduced levels of line edge roughness (LER).

"Line edge roughness (LER)" refers to non-uniform unevenness in the side walls of pattern lines.

[Chemical Formula 35]

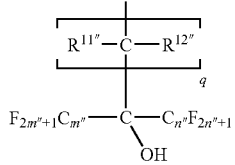

(a1'-1-1)

wherein $R^{11''}$ and $R^{12''}$ each independently represents a hydrogen atom or a lower alkyl group of 1 to 5 carbon atoms, m" and n" each independently represents an integer of 1 to 5, and q also represents an integer of 1 to 5.

In formula (a1'-1-1), $R^{11''}$ and $R^{12''}$ each independently represents a hydrogen atom or a lower alkyl group.

As the lower alkyl group, a linear or branched lower alkyl group of 1 to 5 carbon atoms is preferred, and specific examples include a methyl group, an ethyl group, a propyl group, an isopropyl group, an n-butyl group, an isobutyl group, a tert-butyl group, a pentyl group, an isopentyl group or a neopentyl group, and a methyl group is particularly desirable.

Of the various possibilities, groups in which both $R^{11''}$ and $R^{12''}$ are hydrogen atoms are particularly desirable.

q represents an integer of 1 to 5, and preferably an integer of 1 to 3, and is most preferably 1.

m" and n" each independently represents an integer of 1 to 5, and preferably an integer of 1 to 3. Groups in which both m" and n" are 1 are particularly desirable in terms of ease of synthesis and the effects achieved for the present invention.

The structural unit (a1') may be either a single type of structural unit or a mixture of two or more different structural units.

The proportion of the structural unit (a1') within the copolymer (A2-1), relative to the combined total of all the structural units that constitute the copolymer (A2-1), is preferably within a range from 45 to 90 mol %, more preferably from 50 to 90 mol %, and still more preferably from 55 to 80 mol %. Making this proportion at least as large as the lower limit of the above-mentioned range yields an improvement in the effects achieved by including the structural unit (a1'), whereas by making the proportion no more than the upper limit of the above-mentioned range, a good balance can be achieved with the other structural units.

—Structural Unit (a2')

The copolymer (A2-1) preferably includes a structural unit (a2') having a hydroxyalkyl group.

In the present invention, by including the copolymer (A2-1) that contains the structural unit (a2'), the solubility of the component (A2) within an alkali developing solution may be enhanced. Further, the cross-linking of the component (A2) with the component (C) is enhanced, meaning the difference in the solubility within the alkali developing solution (the contrast) between the exposed portions and the unexposed portions can be increased, enabling the composition to function more effectively as a negative resist.

As the structural unit (a2'), units such as a structural unit (a210) that contains, within the main chain, an aliphatic cyclic group having a hydroxyalkyl group (hereafter abbreviated as "structural unit (a210)") are preferred.

The structural unit (a2') may be either a single type of structural unit or a mixture of two or more different structural units.

—Structural Unit (a210)

In the present invention, the structural unit (a210) is a structural unit that contains, within the main chain, an aliphatic cyclic group having a hydroxyalkyl group.

Examples of the structural unit (a210) include the same units as those described above for the structural unit (a1'), with the exception that the "fluorinated hydroxyalkyl group" within the structural unit (a1') is replaced with an unfluorinated hydroxyalkyl group, namely a hydroxyalkyl group in which a portion of the hydrogen atoms of an alkyl group have been substituted with hydroxyl groups, and the remaining hydrogen atoms have not been substituted with fluorine atoms.

Of the units included within the definition of the structural unit (a210), structural units (a2'-1) represented by general formula (a2'-1) shown below are preferred. By including the structural unit (a2'-1), lithographic properties such as the resist pattern shape and line width roughness (LWR) are improved. Further, a favorable contrast is more readily obtained, and the etching resistance may also improve.

[Chemical Formula 36]

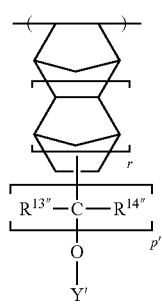

(a2'-1)

wherein $R^{13''}$ and $R^{14''}$ each independently represents a hydrogen atom or a lower alkyl group of 1 to 5 carbon atoms;

Y' represents a hydrogen atom or a hydroxyalkyl group; r represents either 0 or 1; and p' represents an integer of 1 to 3.

The structural unit (a2'-1) represented by general formula (a2'-1) is a structural unit containing, within the main chain, a norbornane or tetracyclododecane structure having a hydroxyalkyl group.

In formula (a2'-1), $R^{13''}$ and $R^{14''}$ each independently represents a hydrogen atom or a lower alkyl group. Examples of the lower alkyl group include the same groups as those described above in relation to the lower alkyl groups represented by $R^{11''}$ and $R^{12''}$ in formula (a1'-1-1) above. Of the various possibilities, groups in which both $R^{13''}$ and $R^{14''}$ are hydrogen atoms are particularly desirable.

Y' represents a hydrogen atom or a hydroxyalkyl group.

As the hydroxyalkyl group, a linear or branched hydroxyalkyl group of 1 to 10 carbon atoms is preferred, a linear or branched hydroxyalkyl group of 1 to 8 carbon atoms is more preferred, and a linear lower hydroxyalkyl group of 1 to 3 carbon atoms is still more preferred.

There are no particular limitations on the number of hydroxyl groups or the bonding positions of those hydroxyl groups within the hydroxyalkyl group, although a single hydroxyl group is typical, and this hydroxyl group is preferably bonded to the alkyl group terminal.

Y' is most preferably a hydrogen atom.

r is either 0 or 1, and is preferably 0.

p' represents an integer of 1 to 3, is preferably 1 or 2, and is most preferably 1.

Specific examples of the structural unit (a2'-1) include units represented by chemical formulas (a2'-1-1) to (a2'-1-7) shown below.

[Chemical Formula 37]

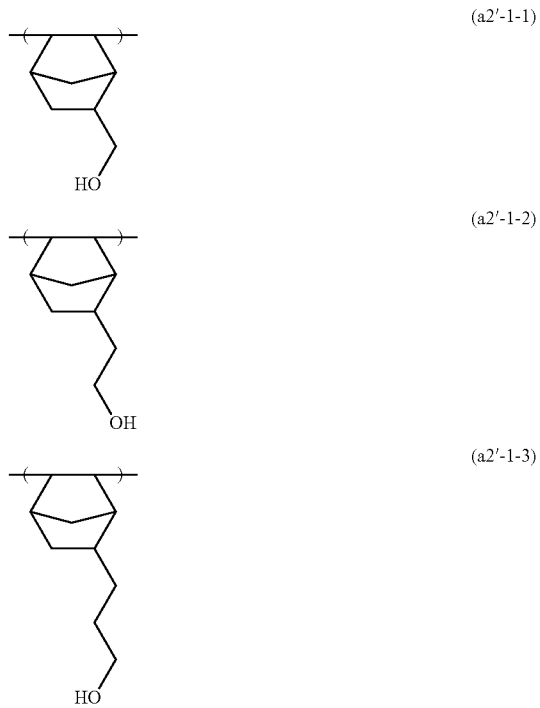

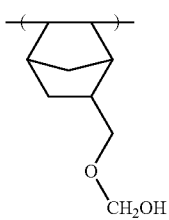 (a2'-1-4)

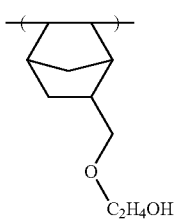 (a2'-1-5)

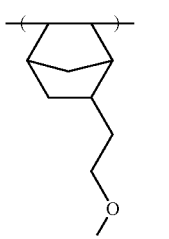 (a2'-1-6)

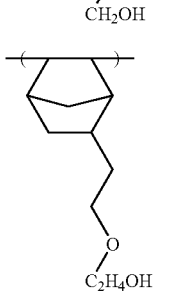 (a2'-1-7)

Of these structural units, those represented by the above-mentioned chemical formulas (a2'-1-1) to (a2'-1-3) are preferred.

The structural unit (a210) may be either a single type of structural unit or a mixture of two or more different structural units.

The proportion of the structural unit (a210) within the copolymer (A2-1), relative to the combined total of all the structural units that constitute the copolymer (A2-1), is preferably within a range from 10 to 50 mol %, more preferably from 15 to 45 mol %, and still more preferably from 20 to 40 mol %. Making this proportion at least as large as the lower limit of the above-mentioned range improves the effects achieved by including the structural unit (a2') such as improving the alkali solubility and making a favorable contrast more readily obtainable. In contrast, by making the proportion no more than the upper limit of the above-mentioned range, a good balance can be achieved with the other structural units.

—Other Structural Units

In the negative resist composition of the present invention, besides the structural units (a1') and (a2') described above, the component (A) may also include another structural unit (a3') typically used in the component (A2) of conventional chemically amplified resist compositions.

However, in terms of the effects achieved for the present invention, the copolymer (A2-1) is preferably a resin in which the structural units (a1') and (a2') represent the main components.

Here, the term "main components" means that the combined quantity of the structural units (a1') and (a2') represents at least 70 mol %, and preferably 80 mol % or greater, of all the structural units. Of the various possibilities, copolymers formed solely from the structural units (a1') and (a2') are the most desirable.

In the present invention, the combination of the structural unit (a1') and the structural unit (a2') within the copolymer (A2-1) is preferably a combination of the structural unit (a1') and the structural unit (a210). Examples of such combinations of structural units include the combinations of structural units represented by chemical formulas (A2-1-1) to (A2-1-4) shown below.

[Chemical Formula 38]

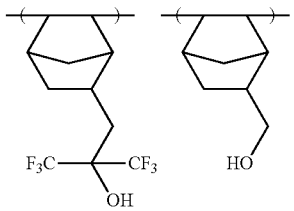 (A2-1-1)

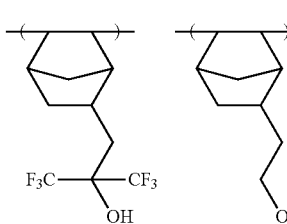 (A2-1-2)

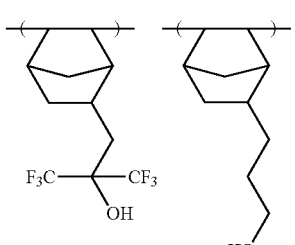 (A2-1-3)

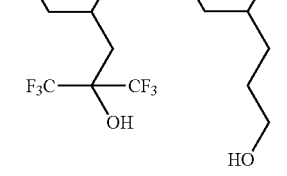 (A2-1-4)

In the copolymer (A2-1) containing the structural unit (a1') and the structural unit (a210), the proportion of the structural unit (a1') within the copolymer (A2-1), relative to the combined total of the structural unit (a1') and the structural unit (a210), is preferably within a range from 50 to 90 mol %, more preferably from 55 to 85 mol %, and still more preferably from 60 to 80 mol %.

Further, the proportion of the structural unit (a210) relative to the combined total of the structural unit (a1') and the structural unit (a210) is preferably within a range from to 50 mol %, more preferably from 15 to 45 mol %, and still more preferably from 20 to 40 mol %.

In the present invention, the weight average molecular weight (Mw, the polystyrene equivalent molecular weight measured by gel permeation chromatography) of the copolymer (A2-1) is preferably within a range from 2,000 to 10,000, more preferably from 3,000 to 6,000, and most preferably from 3,000 to 5,000. Ensuring that this molecular weight is at least as large as the lower limit of the above-mentioned range enables good contrast to be obtained, whereas ensuring the molecular weight is no more than the upper limit of the above-mentioned range can suppress swelling of the resist pattern. As a result, the resolution can be improved. Further, suppressing swelling of the pattern also yields an improvement in the depth of focus (DOF) properties and improved suppression of line edge roughness (LER).

Furthermore, ensuring a weight average molecular weight within the above range is preferred in terms of achieving a large suppression effect on resist pattern swelling. Lower weight average molecular weights within the above-mentioned range tend to yield more favorable properties.

Further, the degree of dispersion (Mw/Mn) is preferably from 1.0 to 5.0, and more preferably from 1.0 to 2.5. Here, Mn is the number average molecular weight.

When the copolymer (A2-1) is used in the component (A2), one type of the above-mentioned copolymer (A2-1) may be used alone, or a mixture of two or more types may be used.

In those cases where the copolymer (A2-1) is used, the proportion of the copolymer (A2-1) within the component (A2) is preferably at least 70% by weight, more preferably at least 80% by weight, and is most preferably 100% by weight.

The component (A2) used in the present invention can be synthesized, for example, by a method in which the monomers that give rise to each of the structural units are subjected to a radical polymerization using normal methods, or the method disclosed in International Publication WO2004/076495.

Further, as the component (A2), an alkali-soluble resin component other than the copolymer (A2-1), for example, other polymeric compounds used in conventional negative resist compositions (such as hydroxystyrene resins, novolak resins or acrylic resins) may also be used.

The quantity of the component (A2) within the negative resist composition may be adjusted in accordance with the resist film thickness that is to be formed.

<Component (B)>

The resist composition of the present invention includes an acid-generator component (B) which generates acid upon exposure, wherein the acid-generator component (B) includes an acid generator (B1) (hereafter, referred to as "component (B1)") composed of a compound having a base dissociable group within a cation moiety.

Here, a "base dissociable group" refers to a group which is dissociated by the action of an alkali developing solution (aqueous alkali solution). As an alkali developing solution, alkali developing solutions generally used in the fields of lithography may be used. In the present invention, it is preferable that the base dissociable group be a group which is dissociated by the action of a 2.38% by weight aqueous solution of tetramethylammonium hydroxide at 23° C.

Further, in the present invention, the component (B1) included in the component (B) is not particularly limited as long as it is an acid generator having a base dissociable group within a cation moiety, but is preferably an acid generator including the compound that has a group represented by general formula (I) shown below as a base dissociable group. Furthermore, it is more preferable that the component (B1) is an acid generator including the compound represented by general formula (b1-11) shown below.

In the group represented by general formula (I) shown below, the C—O bond within the —C(=O)—O— moiety is cleaved (hydrolyzed) by the action of the aforementioned alkali developing solution, thereby forming a carboxyl group.

[Chemical Formula 39]

(b1-11)

wherein $R^{7''}$ to $R^{9''}$ each independently represents an aryl group or an alkyl group, wherein two of $R^{7''}$ to $R^{9''}$ may be bonded to each other to form a ring with the sulfur atom in the formula, and at least one of $R^{7''}$ to $R^{9''}$ represents a substituted aryl group having a group represented by general formula (I) shown below as a substituent; and $X^-$ represents an anion.

[Chemical Formula 40]

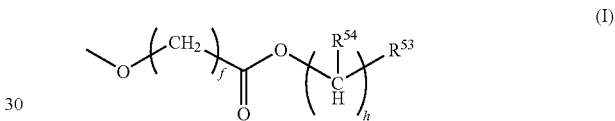

(I)

wherein $R^{53}$ represents a hydrogen atom or a fluorinated alkyl group; $R^{54}$ represents a hydrogen atom, an alkyl group or a fluorinated alkyl group; f represents 0 or 1; and h represents 1 or 2.

—Cation Moiety of the Component (B1)

In formula (b1-11), $R^{7''}$ to $R^{9''}$ each independently represents an aryl group which may have a substituent or an alkyl group which may have a substituent.

At least one of $R^{7''}$ to $R^{9''}$ represents a substituted aryl group having a group represented by general formula (I) shown above as a substituent, and two of $R^{7''}$ to $R^{9''}$ may be bonded to each other to form a ring with the sulfur atom in the formula.

The aryl group for $R^{7''}$ to $R^{9''}$ is not particularly limited. For example, an aryl group having 6 to 20 carbon atoms may be used in which some or all of the hydrogen atoms of the aryl group may or may not be substituted with substituents other than the substituent group represented by general formula (I) above, such as alkyl groups, alkoxy groups, halogen atoms or hydroxyl groups. As such aryl groups, aryl groups having 6 to 10 carbon atoms are preferred because they can be synthesized at a low cost. Specific examples thereof include a phenyl group and a naphthyl group.

The alkyl group, with which hydrogen atoms of the aryl group may be substituted, is preferably an alkyl group having 1 to 5 carbon atoms, more preferably a methyl group, an ethyl group, a propyl group, an n-butyl group, or a tert-butyl group, and most preferably a methyl group.

The alkoxy group, with which hydrogen atoms of the aryl group may be substituted, is preferably an alkoxy group having 1 to 5 carbon atoms, and more preferably a methoxy group, an ethoxy group, an n-propoxy group, an iso-propoxy group, an n-butoxy group or a tert-butoxy group.

The halogen atom, with which hydrogen atoms of the aryl group may be substituted, is preferably a fluorine atom.

The alkyl group for $R^{7'''}$ to $R^{9'''}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. Of these various possibilities, a methyl group is most preferable because it is excellent in resolution and can be synthesized at a low cost.

When two of $R^{7'''}$ to $R^{9'''}$ are bonded to each other to form a ring with the sulfur atom in the formula, it is preferable that the two of $R^{7'''}$ to $R^{9'''}$ form a 3 to 10-membered ring including the sulfur atom, and it is particularly desirable that the two of $R^{7'''}$ to $R^{9'''}$ form a 5 to 7-membered ring including the sulfur atom.

When two of $R^{7'''}$ to $R^{9'''}$ are bonded to each other to form a ring with the sulfur atom in the formula, the remaining one of $R^{7'''}$ to $R^{9'''}$ is preferably an aryl group. The aryl group is preferably a substituted aryl group having a group represented by general formula (I) above as a substituent.

In the compound represented by general formula (b1-11) above, at least one of $R^{7'''}$ to $R^{9'''}$ represents a substituted aryl group having a group represented by general formula (I) above as a substituent (hereafter, referred to as a substituted aryl group (I)).

The number of groups represented by general formula (I) above included in one substituted aryl group (I) is preferably within a range from 1 to 3, and is most preferably 1.

Further, in the substituted aryl group (I), the aryl group to which the group represented by general formula (I) bonds is preferably a phenyl group or a naphthyl group, and a phenyl group is particularly desirable. In this case, the group represented by general formula (I) above preferably bonds to the para position of the phenyl group.

The substituted aryl group (I) may also include another substituent other than the group represented by general formula (I). Examples of the substituent other than the group represented by general formula (I) include an alkyl group, an alkoxy group, an ether group, a halogen atom, a halogenated alkyl group, and a hydroxyl group. As the alkyl group, alkoxy group and halogen atom, the same alkyl group, alkoxy group and halogen atom mentioned above as the substituent groups for the substituted aryl group can be used. Examples of the halogenated alkyl group include a group in which hydrogen atoms within the aforementioned alkyl group have been substituted with the aforementioned halogen atoms. Examples of the ether group include a group represented by formula —O—$R^{O1}$—$R^{O2}$ (wherein $R^{O1}$ represents an alkylene group and $R^{O2}$ represents an alkyl group). The alkylene group for $R^{O1}$ may be linear, branched or cyclic, and is preferably linear or branched. Further, the number of carbon atoms within the alkylene group is preferably within a range from 1 to 10, and more preferably within a range from 1 to 5. Specific examples of the alkylene group include groups in which one hydrogen atom has been removed from the alkyl groups exemplified above as unsubstituted alkyl groups. The alkyl group for $R^{O2}$ may be linear, branched or cyclic, and is preferably linear or branched. Further, the number of carbon atoms within the alkyl group is preferably within a range from 1 to 10, and more preferably within a range from 1 to 5. More specifically, as the alkyl group, the same as the unsubstituted alkyl groups exemplified above can be mentioned.

The number of the substituents other than the group represented by general formula (I) included in one substituted aryl group (I) is preferably within a range from 0 to 2.

One, two or all three of $R^{7'''}$ to $R^{9'''}$ may be a substituted aryl group (I). However, it is most preferable that only one of $R^{7'''}$ to $R^{9'''}$ be a substituted aryl group (I).

In this case, it is preferable that the remaining two of $R^{7'''}$ to $R^{9'''}$ either represent an aryl group that may have another substituent other than the group represented by formula (I), or be bonded to each other to form a ring with the sulfur atom in the formula.

When the remaining two of $R^{7'''}$ to $R^{9'''}$ represent an aryl group that may have a substituent, the aryl group is preferably an unsubstituted aryl group, more preferably a phenyl group or a naphthyl group, and most preferably a phenyl group.

In general formula (I) above, $R^{53}$ represents a hydrogen atom or a fluorinated alkyl group.

The fluorinated alkyl group for $R^{53}$ may be either a group in which part of the hydrogen atoms within an unsubstituted alkyl group described below has been substituted with fluorine atoms, or a group in which all of the hydrogen atoms within an unsubstituted alkyl group described below has been substituted with fluorine atoms (i.e., a perfluoroalkyl group).

The above-mentioned unsubstituted alkyl group may be a linear or branched alkyl group.

The unsubstituted linear alkyl group preferably has 1 to 10 carbon atoms, and more preferably 1 to 8 carbon atoms. Specific examples include a methyl group, an ethyl group, an n-propyl group, an n-butyl group, an n-pentyl group, an n-hexyl group, an n-heptyl group, an n-octyl group, an n-nonyl group and an n-decanyl group.

The unsubstituted branched alkyl group preferably has 3 to 10 carbon atoms, more preferably 3 to 8 carbon atoms, and is most preferably a tertiary alkyl group.

The fluorinated alkyl group for $R^{53}$ is preferably a linear perfluoroalkyl group in which all of the hydrogen atoms within an unsubstituted alkyl group described above have been substituted with fluorine atoms. More specifically, a trifluoromethyl group, a pentafluoroethyl group, a heptafluoro-n-propyl group, and a nonafluoro-n-butyl group are particularly desirable.

In general formula (I) above, $R^{54}$ represents a hydrogen atom, an alkyl group or a fluorinated alkyl group.

As the alkyl group for $R^{54}$, the same unsubstituted alkyl groups as those mentioned above for $R^{53}$ can be mentioned. As the fluorinated alkyl group for $R^{54}$, the same fluorinated alkyl groups as those mentioned above for $R^{53}$ can be mentioned.

$R^{54}$ is most preferably a hydrogen atom.

In general formula (I) above, f represents either 0 or 1, and is preferably 1.

[Chemical Formula 41]

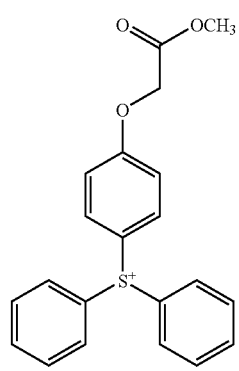

(b1-11-1)

(b1-11-2)
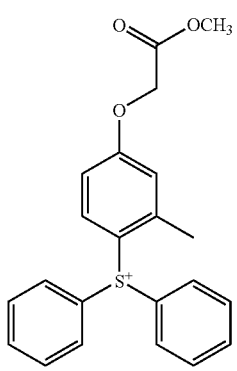
(b1-11-3)
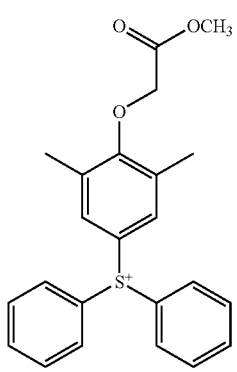
(b1-11-4)
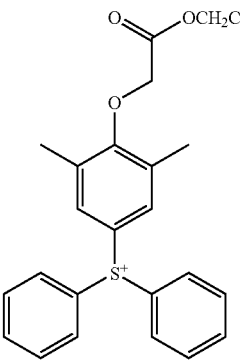
(b1-11-5)
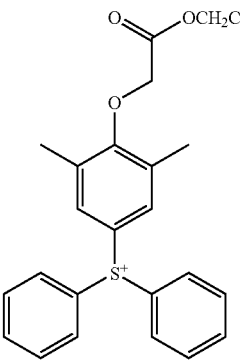
(b1-11-6)
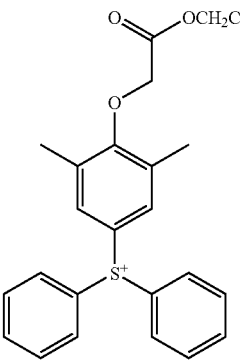
[Chemical Formula 42]
(b1-11-7)
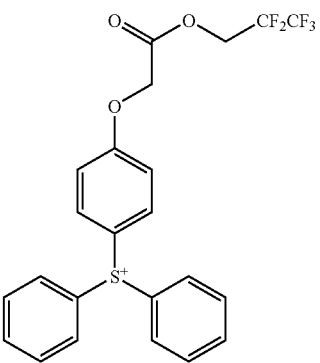
(b1-11-8)
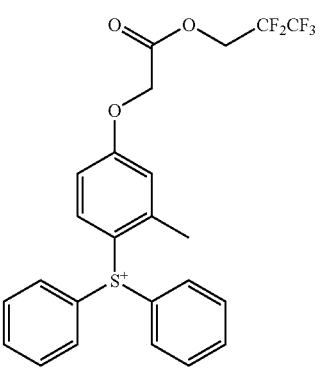
(b1-11-9)
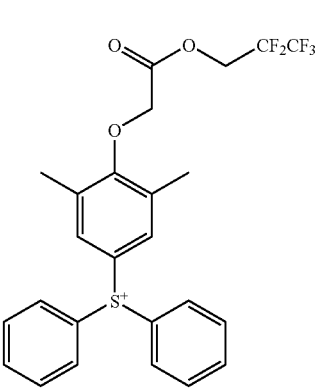

(b1-11-10)
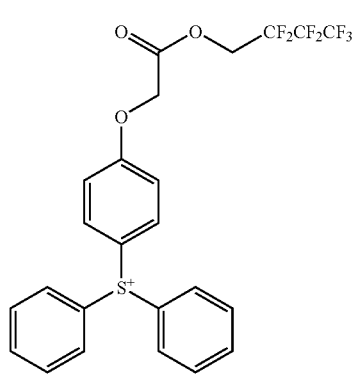
(b1-11-11)
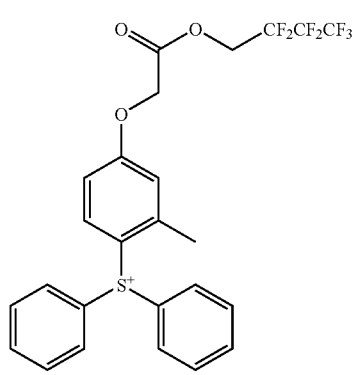
(b1-11-12)
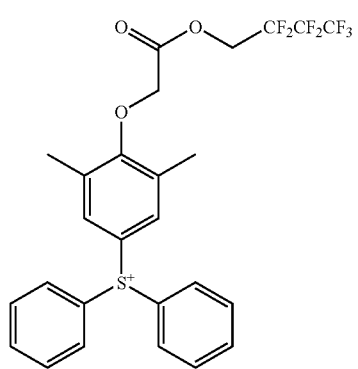
(b1-11-13)
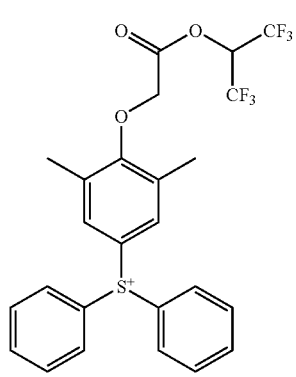
(b1-11-14)
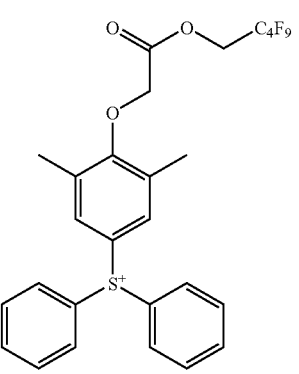
[Chemical Formula 43]
(b1-11-15)
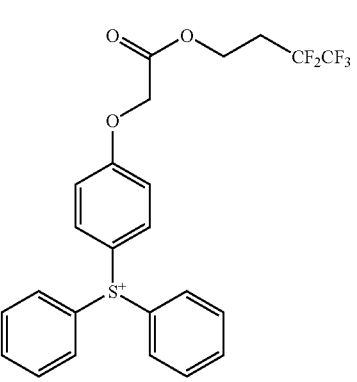
(b1-11-16)
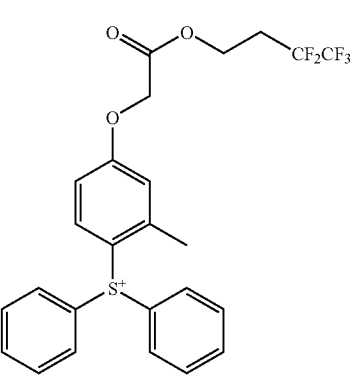
(b1-11-17)
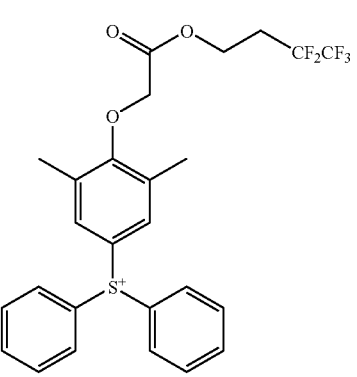

(b1-11-18)
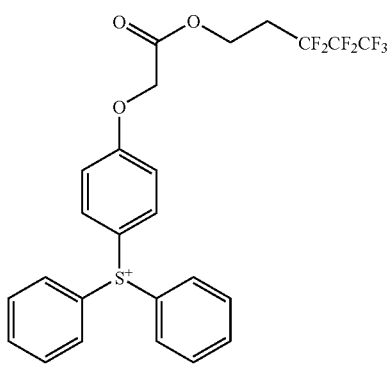

(b1-11-19)
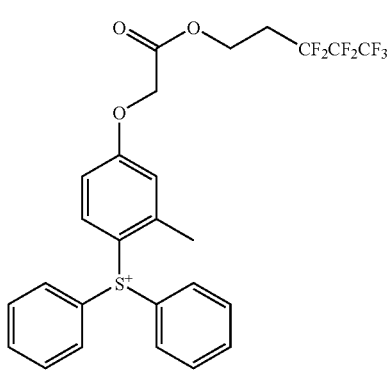

(b1-11-20)
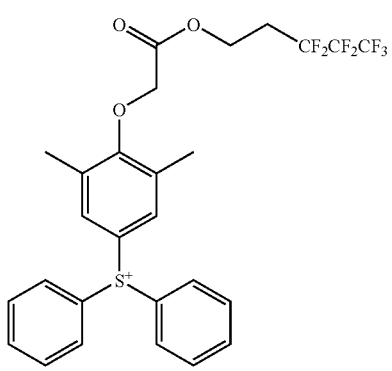

(b1-11-21)
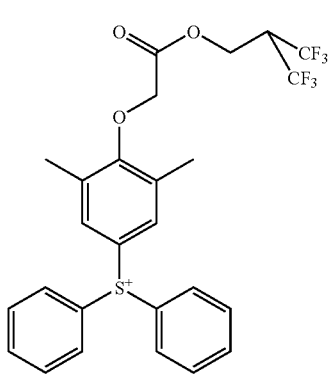

(b1-11-22)
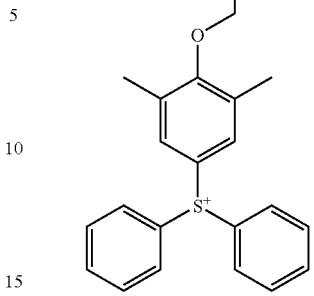

—Anion Moiety of the Component (B1)

In formula (b1-11), there are no particular limitations on the anion for X⁻, and examples of anions include sulfonate anions, imide anions, and methide anions.

Preferred examples of the sulfonate anions include an anion represented by general formula (x-1) shown below.

[Chemical Formula 44]

$$R^{4'''}-SO_3^-  \quad (x\text{-}1)$$

wherein $R^{4'''}$ represents an alkyl group, a halogenated alkyl group, an aryl group or an alkenyl group which may have a substituent.

The alkyl group for $R^{4'''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms. The cyclic group may be either a monocyclic or polycyclic group, and specific examples thereof include a cyclopentyl group, a cyclohexyl group, an adamantyl group, a norbornyl group, an isobornyl group, a tricyclodecanyl group, and a tetracyclododecanyl group.

When $R^{4'''}$ represents an alkyl group, the component (B) exhibits weak acid strength, but can be used favorably in a negative resist composition for example.

Examples of the halogenated alkyl group for $R^{4'''}$ include groups in which some or all of the hydrogen atoms of an above-mentioned linear, branched or cyclic alkyl group have been substituted with halogen atoms. Examples of the halogen atom include a fluorine atom, a chlorine atom, a bromine atom and an iodine atom, and a fluorine atom is particularly desirable.

In the halogenated alkyl group, the percentage of the number of halogen atoms relative to the combined total of halogen atoms and hydrogen atoms within the halogenated alkyl group (namely, the halogenation ratio (%)) is preferably 10 to 100%, more preferably 50 to 100%, and most preferably 100%. Higher halogenation ratios are preferred, as they result in increased acid strength.

The aryl group for $R^{4'''}$ is preferably an aryl group of 6 to 20 carbon atoms.

The alkenyl group for $R^{4'''}$ is preferably an alkenyl group of 2 to 10 carbon atoms.

With respect to $R^{4'''}$, the expression "may have a substituent" means that part of or all of the hydrogen atoms within the alkyl group, halogenated alkyl group, aryl group or alkenyl group may be substituted with a substituent (an atom other than a hydrogen atom or a group).

$R^{4''}$ may have one substituent, or two or more substituents.

Examples of the substituent include a halogen atom, a hetero atom, an alkyl group, and a group represented by formula Z-$Q^1$-[wherein $Q^1$ represents a divalent linking group containing an oxygen atom, and Z represents a hydrocarbon group of 3 to 30 carbon atoms which may have a substituent].

Examples of the halogen atom include the same halogen atoms as those described above with respect to the halogenated alkyl group for $R^{4''}$.

Examples of the alkyl group include the same alkyl groups as those described above for $R^{4''}$.

Examples of the hetero atom include an oxygen atom (=O, —O—), a nitrogen atom, and a sulfur atom.

In the group represented by formula Z-$Q^1$-, $Q^1$ represents a divalent linking group containing an oxygen atom.

$Q^1$ may include another atom other than an oxygen atom. Examples of the atom other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an amide bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group.

Specific examples of the combinations of the aforementioned non-hydrocarbon, oxygen atom-containing linking groups and an alkylene group include —$R^{91}$—O—, —$R^{92}$—O—C(=O)—, —O—$R^{92}$—O—C(=O)—, —C(=O)—O—$R^{93}$—O—C(=O)— and —C(=O)—O—$R^{93}$— (wherein each of $R^{91}$ to $R^{93}$ independently represents an alkylene group).

The alkylene group for $R^{91}$ to $R^{93}$ is preferably a linear or branched alkylene group, and the alkylene group preferably has 1 to 12 carbon atoms, more preferably 1 to 5 carbon atoms, and most preferably 1 to 3 carbon atoms.

Specific examples of the alkylene group include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$; an ethylene group [—$CH_2CH_2$—]; alkylethylene groups such as —CH($CH_3$)$CH_2$—, —CH($CH_3$)CH($CH_3$)—, —C($CH_3$)$_2CH_2$—, —CH($CH_2CH_3$)$CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

As $Q^1$, a divalent linking group containing an ester bond or an ether bond is preferable, and groups represented by formulas —O—, —$R^{91}$—O—, —O—C(=O)—, —O—$R^{92}$—O—C(=O)—, —$R^{92}$—O—C(=O)—, —C(=O)—O—$R^{93}$—O—C(=O)— and —C(=O)—O—$R^{93}$— are preferred, and groups represented by formulas —O—C(=O)—, —C(=O)—O—$R^{93}$—O—C(=O)— and —C(=O)—O—$R^{93}$— are particularly desirable.

In the group represented by the formula Z-$Q^1$-, the hydrocarbon group for Z may be either an aromatic hydrocarbon group or an aliphatic hydrocarbon group.

An aromatic hydrocarbon group is a hydrocarbon group having an aromatic ring. The aromatic hydrocarbon ring preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. Here, the number of carbon atoms within a substituent(s) is not included in the number of carbon atoms of the aromatic hydrocarbon group.

Specific examples of the aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an arylalkyl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atoms, more preferably 1 or 2 carbon atoms, and most preferably 1 carbon atom.

The aromatic hydrocarbon group may have a substituent. For example, a part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which a part of the carbon atoms constituting the ring within the aforementioned aryl group has been substituted with a hetero atom such as an oxygen atom, a sulfur atom or a nitrogen atom, and a heteroarylalkyl group in which a part of the carbon atoms constituting the aromatic hydrocarbon ring within the aforementioned arylalkyl group has been substituted with the aforementioned hetero atom can be used.

In the latter example, as the substituent for the aromatic hydrocarbon group, an alkyl group, an alkoxy group, a halogen atom, a halogenated alkyl group, a hydroxyl group, an oxygen atom (=O) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Examples of the halogenated alkyl group as the substituent for the aromatic hydrocarbon group include a group in which a part or all of the hydrogen atoms within the aforementioned alkyl group have been substituted with the aforementioned halogen atoms.

The aliphatic hydrocarbon group for Z may be either a saturated aliphatic hydrocarbon group, or an unsaturated aliphatic hydrocarbon group. Further, the aliphatic hydrocarbon group may be any of linear, branched or cyclic.

In the aliphatic hydrocarbon group for Z, a part of the carbon atoms constituting the aliphatic hydrocarbon group may be substituted with a substituent group containing a hetero atom, or a part or all of the hydrogen atoms constituting the aliphatic hydrocarbon group may be substituted with a substituent group containing a hetero atom.

As the "hetero atom" for Z, there is no particular limitation as long as it is an atom other than a carbon atom and a hydrogen atom, and examples thereof include a halogen atom, an oxygen atom, a sulfur atom and a nitrogen atom.

Examples of the halogen atom include a fluorine atom, a chlorine atom, an iodine atom and a bromine atom.

The substituent group containing a hetero atom may consist solely of the above-mentioned hetero atom, or may be a group containing a group or atom other than the above-mentioned hetero atom.

Specific examples of the substituent group for substituting a part of the carbon atoms include —O—, —C(=O)—O—, —C(=O)—, —O—C(=O)—O—, —C(=O)—NH—, —NH— (wherein H may be substituted with a substituent such as an alkyl group or an acyl group), —S—, —S(=O)$_2$— and —S(=O)$_2$—O—. When the aliphatic hydrocarbon group is cyclic, the aliphatic hydrocarbon group may contain these substituent groups in the ring structure.

Examples of the substituent group for substituting a part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Examples of the aforementioned halogenated alkyl group include a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15 carbon atoms, and most preferably 1 to 10 carbon atoms. Specific examples include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15 carbon atoms, and most preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5 carbon atoms, still more preferably 2 to 4 carbon atoms, and most preferably 3 carbon atoms. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably to 30 carbon atoms, still more preferably 5 to 20 carbon atoms, still more preferably 6 to 15 carbon atoms, and most preferably 6 to 12 carbon atoms.

Examples thereof include groups in which one or more of the hydrogen atoms have been removed from a monocycloalkane; and groups in which one or more of the hydrogen atoms have been removed from a polycycloalkane such as a bicycloalkane, a tricycloalkane, or a tetracycloalkane. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L5) and (S1) to (S4) shown below.

[Chemical Formula 45]

(L1)

(L2)

(L3)

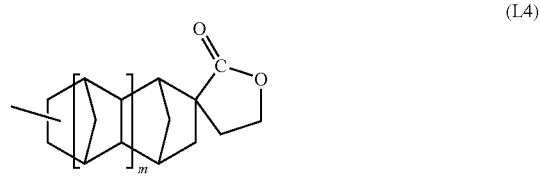
(L4)

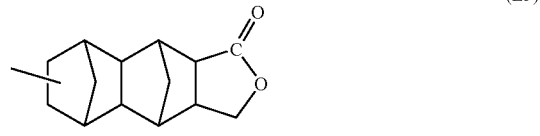
(L5)

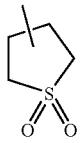 (S1)

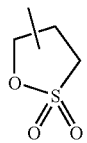 (S2)

 (S3)

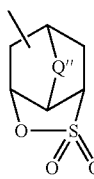 (S4)

wherein Q″ represents an alkylene group of 1 to 5 carbon atoms, —O—, —S—, —O—$R^{94}$— or —S—$R^{95}$— (wherein each of $R^{94}$ and $R^{95}$ independently represents an alkylene group of 1 to 5 carbon atoms); and m represents an integer of 0 or 1.

In the formula above, as the alkylene group for Q″, $R^{94}$ and $R^{95}$, the same alkylene groups as those described above for $R^{91}$ to $R^{93}$ can be used.

In these aliphatic cyclic groups, a part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the aforementioned substituent groups for substituting a part or all of the hydrogen atoms can be used.

In the present invention, Z is preferably a cyclic group which may have a substituent. The cyclic group may be an aromatic hydrocarbon group which may have a substituent or an aliphatic cyclic group which may have a substituent, and an aliphatic cyclic group which may have a substituent is preferable.

The aromatic hydrocarbon group is preferably a naphthyl group which may have a substituent or a phenyl group which may have a substituent.

As the aliphatic cyclic group which may have a substituent, an aliphatic polycyclic group which may have a substituent is preferable. As the aliphatic polycyclic group, the aforementioned groups in which one or more hydrogen atoms have been removed from polycycloalkanes, the aforementioned groups represented by formulas (L2) to (L5) and (S3) to (S4), and the like are preferable.

In the present invention, in those cases where $R^{4″}$ has Z-$Q^1$ as a substituent, $R^{4″}$ is preferably a group represented by formula Z-$Q^1$-$Y^1$— (wherein $Q^1$ and Z are the same as defined above for $Q^1$ and Z in the aforementioned formula Z-$Q^1$-; and $Y^1$ represents an alkylene group of 1 to 4 carbon atoms which may have a substituent, or a fluorinated alkylene group of 1 to 4 carbon atoms which may have a substituent).

That is, in those cases where $X^-$ is a sulfonate anion, it is preferably an anion represented by general formula (x-11) shown below.

[Chemical Formula 46]

$$Z\text{-}Q^1\text{-}Y^1\text{—}SO_3^- \tag{x-11}$$

wherein $Q^1$ represents a divalent linking group containing an oxygen atom; Z represents a hydrocarbon group of 3 to 30 carbon atoms which may have a substituent; and $Y^1$ represents an alkylene group of 1 to 4 carbon atoms which may have a substituent, or a fluorinated alkylene group of 1 to 4 carbon atoms which may have a substituent.

In formula (x-11), Z and $Q^1$ are the same as defined above for Z and $Q^1$ in the aforementioned formula Z-$Q^1$-.

As the alkylene group for $Y^1$, the same alkylene groups as those described above for $Q^1$ in which the number of carbon atoms is 1 to 4 can be used.

As the fluorinated alkylene group for $Y^1$, groups in which part of or all of the hydrogen atoms in the alkylene groups described above are substituted with fluorine atoms can be used.

Specific examples of $Y^1$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, and —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, and —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

$Y^1$ is preferably a fluorinated alkylene group, and particularly preferably a fluorinated alkylene group in which the carbon atom bonded to the adjacent sulfur atom is fluorinated. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, and —$CF(CF_2CF_3)CF_2$—; —$CH_2CF_2$—, —$CH_2CH_2CF_2$—, and —$CH_2CF_2CF_2$—; —$CH_2CH_2CH_2CF_2$—, —$CH_2CH_2CF_2CF_2$—, and —$CH_2CF_2CF_2CF_2$—.

Among these, —$CF_2$—, —$CF_2CF_2$—, —$CF_2CF_2CF_2$—, and $CH_2CF_2CF_2$— are preferable, —$CF_2$—, —$CF_2CF_2$— and —$CF_2CF_2CF_2$— are more preferable, and —$CF_2$— is particularly desirable.

The alkylene group or fluorinated alkylene group for $Y^1$ may have a substituent. The alkylene group or fluorinated alkylene group "has a substituent" means that part or all of the hydrogen atoms or fluorine atoms in the alkylene group or fluorinated alkylene group have been substituted with atoms or groups other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxyl group.

Preferred examples of the anions represented by formula (x-11) include anions represented by formulas (b1) to (b8) shown below.

[Chemical Formula 47]

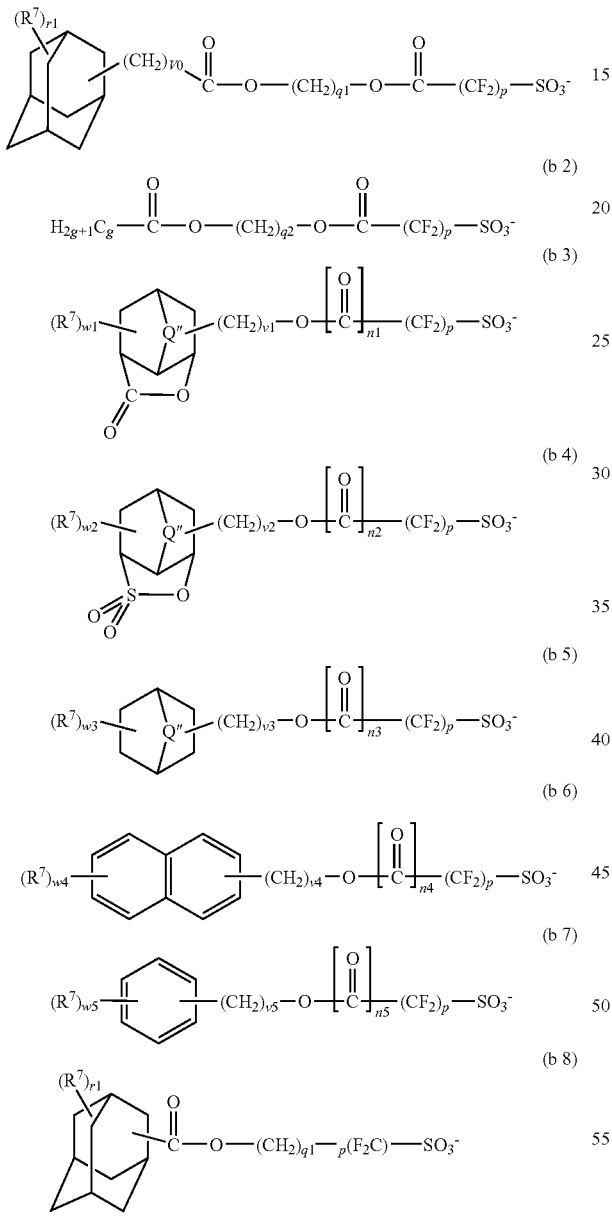

wherein p represents an integer of 1 to 3; each of q1 and q2 independently represents an integer of 1 to 5; r1 represents an integer of 0 to 3; g represents an integer of 1 to 20; $R^7$ represents a substituent; each of n1 to n5 independently represents 0 or 1; each of v0 to v5 independently represents an integer of 0 to 3; each of w1 to w5 independently represents an integer of 0 to 3; and Q″ is as defined above for Q″ in the aforementioned formulas (L1) to (L5) and (S1) to (S4).

As the substituent for $R^7$, the same groups as those which the aforementioned aliphatic hydrocarbon group or aromatic hydrocarbon group for Z may have as a substituent can be used.

When the subscripts of $R^7$ (namely, r1, and w1 to w5) represent an integer of 2 or more, the plurality of $R^7$ groups in the compound may be the same or different from each other.

Further, in those cases where $X^-$ is an imide anion, examples of the anions which can be used as $X^-$ include anions represented by general formulas (b-3) and (b-4) shown below.

[Chemical Formula 48]

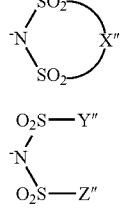

wherein X″ represents an alkylene group of 2 to 6 carbon atoms in which at least one hydrogen atom has been substituted with a fluorine atom; Y″ and Z″ each independently represents an alkyl group or halogenated alkyl group which may have a substituent.

X″ represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

The smaller the number of carbon atoms within the alkylene group for X″ within the above ranges for the number of carbon atoms, the better the solubility in a resist solvent.

In the alkylene group for X″, it is preferable that the number of hydrogen atoms substituted with fluorine atoms is as large as possible, as the acid strength increases, and the transparency to high energy radiation of 200 nm or less or electron beam is improved. The percentage of the fluorine atoms within the alkylene group, i.e., the fluorination ratio is preferably from 70 to 100%, more preferably from 90 to 100%, and it is particularly desirable that the alkylene group be a perfluoroalkylene group in which all hydrogen atoms are substituted with fluorine atoms.

Y″ and Z″ each independently represents an alkyl group or halogenated alkyl group which may have a substituent.

The alkyl group for Y″ and Z″ may be a linear, branched or cyclic alkyl group, and examples thereof include the same alkyl groups as those described above for $R^{4″}$.

Examples of the halogenated alkyl group for Y″ and Z″ include groups in which some or all of the hydrogen atoms of an above-mentioned linear, branched or cyclic alkyl group have been substituted with halogen atoms, and include the same alkyl groups as those described above for $R^{4″}$.

In the halogenated alkyl group, the ratio of the number of halogen atoms relative to the combined total of halogen atoms and hydrogen atoms within the halogenated alkyl group (namely, the halogenation ratio (%)) is preferably 10 to 100%, more preferably 50 to 100%, and is most preferably 100%. Higher halogenation ratios are preferred, as they result in increased acid strength.

With respect to Y″ and Z″, the expression "may have a substituent" means that part of or all of the hydrogen atoms within the alkyl group or halogenated alkyl group may be substituted with a substituent (atoms other than hydrogen atoms, or groups). The number of substituents within Y" and Z" may be either 1, or 2 or greater.

Examples of the substituent include a halogen atom, a hetero atom, an alkyl group, and a group represented by formula Z-$Q^1$-[wherein $Q^1$ represents a divalent linking group containing an oxygen atom, and Z represents a hydrocarbon group of 3 to 30 carbon atoms which may have a substituent].

Examples of the halogen atom include the same halogen atoms as those described above with respect to the halogenated alkyl group for $R^{4"}$.

Examples of the alkyl group include the same alkyl groups as those described above for $R^{4"}$.

As the hetero atom, the same hetero atoms as those which the aforementioned alkyl group for $R^{4"}$ may have as a substituent can be used.

In the group represented by formula Z-Q-, $Q^1$ represents a divalent linking group containing an oxygen atom.

Examples of the divalent linking groups containing an oxygen atom include non-hydrocarbon, oxygen atom-containing linking groups such as an oxygen atom (an ether bond; —O—), an ester bond (—C(=O)—O—), a carbonyl group (—C(=O)—) and a carbonate bond (—O—C(=O)—O—); and combinations of the aforementioned non-hydrocarbon, oxygen atom-containing linking groups with an alkylene group.

Specific examples of the combinations of the aforementioned non-hydrocarbon, oxygen atom-containing linking groups and an alkylene group include —$R^{91}$—O— and —$R^{92}$—O—C(=O)— (wherein each of $R^{91}$ and $R^{92}$ independently represents an alkylene group).

The alkylene group for $R^{91}$ and $R^{92}$ is preferably a linear or branched alkylene group, and the alkylene group preferably has 1 to 12 carbon atoms, more preferably 1 to 5 carbon atoms, and most preferably 1 to 3 carbon atoms. More specifically, the same alkylene groups for $R^{91}$ and $R^{92}$ as those described above in relation to the substituent of $R^{4"}$ can be used.

As $Q^1$, a divalent linking group containing an ester bond or an ether bond is preferable.

In the group represented by the formula Z-$Q^1$-, as the hydrocarbon group for Z, the same alkylene groups for $R^{91}$ and $R^{92}$ as those described above in relation to the substituent of $R^{4"}$ can be used. Z is preferably an aliphatic hydrocarbon group, and more preferably a linear or cyclic aliphatic hydrocarbon group.

Preferred examples of the anions in those cases where the formula (b4) has Z-$Q^1$ as a substituent include anions represented by formulas (b4-1) to (b4-11) shown below.

[Chemical Formula 49]

(b4-1)

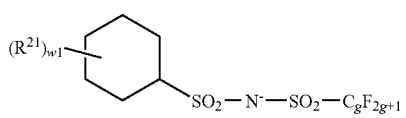

(b4-2)

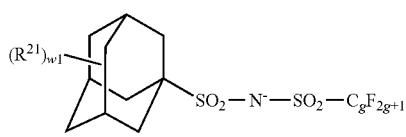

(b4-3)

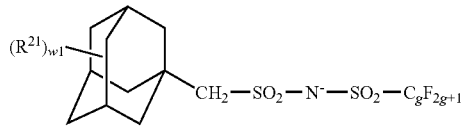

(b4-4)

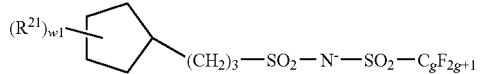

(b4-5)

$CH_3$—$(CH_2)_{10}$—$SO_2$—$N^-$—$SO_2$—$C_gF_{2g+1}$ (b4-6)

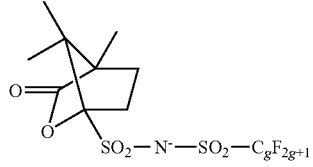

[Chemical Formula 50]

(b4-7)

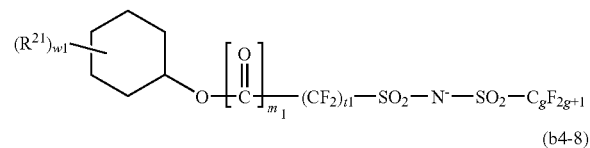

(b4-8)

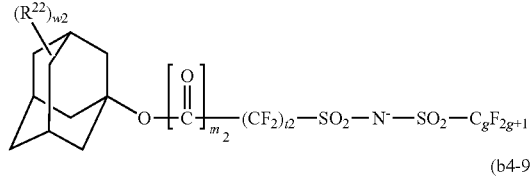

(b4-9)

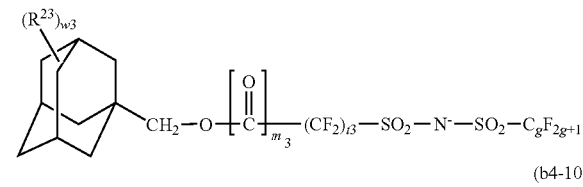

(b4-10)

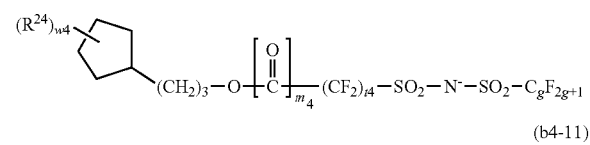

(b4-11)

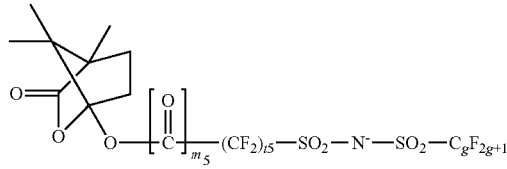

wherein g represents an integer of 1 to 4; each of t1 to t5 represents an integer of 1 to 4; each of $m_1$ to $m_5$ represents either 0 or 1; each of w1 to w5 independently represents an integer of 0 to 3; and each of $R^{21}$ to $R^{24}$ represents a substituent.

g represents an integer of 1 to 4 and is preferably 1 or 2, and is most preferably 1.

Each of t1 to t5 independently represents an integer of 1 to 4, is preferably 1 or 2, and is most preferably 2.

Each of $m_1$ to $m_5$ independently represents either 0 or 1, and is preferably 0.

Each of w1 to w5 independently represents an integer of 0 to 3, is preferably 0 or 1, and is most preferably 1.

As the substituent for $R^{21}$ to $R^{24}$, the same groups as those which the aforementioned aliphatic hydrocarbon group for Z may have as a substituent can be used.

When the subscripts of $R^{21}$ to $R^{24}$ (namely, w1 to w4) represent an integer of 2 or more, the plurality of $R^{21}$ to $R^{24}$ groups in the compound may be the same or different from each other.

With respect to Y" and Z", in those cases where one represents an alkyl group while the other represents a fluorinated alkyl group, —$SO_2$— bonded to the alkyl group may be substituted with —C(=O)—. As the alkyl group, the same as those described above for $R^{4"}$ may be used. More specifically, preferred examples include those having a cyclic alkyl group such as a methyladamantyl group and an adamantyl group.

Further, in those cases where $X^-$ is a methide anion, examples of the methide anion include anions represented by general formula (b-c1) shown below.

[Chemcial Formula 51]

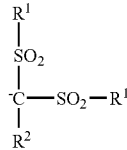

(b-c1)

wherein $R^1$ represents an alkyl group of 1 to 10 carbon atoms in which at least one hydrogen atom is substituted with a fluorine atom; and $R^2$ represents a hydrocarbon group which may have a substituent, or —$SO_2$—$R^1$.

In general formula (b-c1), $R^1$ represents an alkyl group of 1 to 10 carbon atoms in which at least one hydrogen atom is substituted with a fluorine atom. The alkyl group may be a linear, branched or cyclic alkyl group. In the present invention, $R^1$ is preferably a linear or branched alkyl group, and more preferably a linear alkyl group.

When $R^2$ represents a hydrocarbon group which may have a substituent in general formula (b-c1) (the expression "hydrocarbon group which may have a substituent" means that a part or all of the hydrogen atoms constituting the hydrocarbon group may be substituted with a substituent), the hydrocarbon group for $R^2$ may be either an aliphatic hydrocarbon group or an aromatic hydrocarbon group. Specific examples thereof include the same as those described for Z in the above formula Z-$Q^1$-.

$R^2$ is preferably a halogenated aryl group, and examples thereof include an aryl group of 6 to 10 carbon atoms, such as a phenyl group and a naphthyl group, in which a part or all of the hydrogen atoms of the aryl groups have been substituted with the aforementioned halogen atoms (preferably fluorine atoms).

Further, in those cases where $X^-$ is a halogen anion, examples of $X^-$ include a fluorine anion, a chlorine anion, a bromine anion and an iodine anion.

In the present invention, of the various possibilities described above, $X^-$ is preferably an anion in which $R^{4"}$ in general formula (x-1) above represents a fluorinated alkyl group which may have a substituent (namely, a fluorinated alkylsulfonate ion which may have a substituent).

Examples of the fluorinated alkyl group which may have a substituent include groups in which a part or all of the hydrogen atoms of the aforementioned alkyl groups for $R^{4"}$ have been substituted with fluorine atoms. However, an alkyl group or fluorinated alkyl group having 6 or more carbon atoms is hardly decomposable, and hence, in consideration of safety in handling in terms of bioaccumulation, those having 4 or less carbon atoms, for example, a nonafluorobutanesulfonic acid ion or the like is particularly desirable.

As the component (B1), one type may be used alone, or two or more types may be used in combination.

The proportion of the component (B1) within the component (B) is preferably from 1 to 100% by weight, more preferably from 20 to 100% by weight, and still more preferably from 50 to 100% by weight.

In the resist composition of the present invention, the component (B) may further include an acid generator component other than the component (B1) (hereafter, referred to as "component (B2)").

As the component (B2), there is no particular limitation, and any of the known acid generators used in conventional chemically amplified resist compositions can be used. Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator, a compound represented by general formula (b-1) or (b-2) shown below can be used.

[Chemical Formula 52]

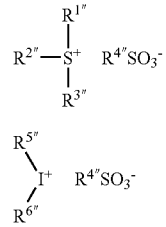

(b-1)

(b-2)

wherein $R^{1"}$ to $R^{3"}$, $R^{5"}$ and $R^{6"}$ each independently represents an aryl group or an alkyl group, wherein two of $R^{1"}$ to $R^{3"}$ in general formula (b-1) may be bonded to each other to form a ring with the sulfur atom in the formula; with the proviso that at least one of $R^{1"}$ to $R^{3"}$ represents an aryl group, and at least one of $R^{5"}$ and $R^{6"}$ represents an aryl group; and $R^{4"}$ is the same as $R^{4"}$ in the above general formula (x-1).

In general formula (b-1), $R^{1"}$ to $R^{3"}$ each independently represents an aryl group or an alkyl group. In general formula (b-1), two of $R^{1"}$ to $R^{3"}$ may be bonded to each other to form a ring with the sulfur atom in the formula.

Further, among $R^{1"}$ to $R^{3"}$, at least one group represents an aryl group. Among $R^{1"}$ to $R^{3"}$, two or more groups are preferably aryl groups, and it is particularly desirable that all of $R^{1"}$ to $R^{3"}$ are aryl groups.

The aryl group for $R^{1"}$ to $R^{3"}$ is not particularly limited. For example, an aryl group having 6 to 20 carbon atoms may be used in which some or all of the hydrogen atoms of the aryl group may or may not be substituted with alkyl groups, alkoxy groups, ether groups, halogen atoms, halogenated alkyl groups, hydroxyl groups, or the like. The aryl group is preferably an aryl group having 6 to 10 carbon atoms because it can be synthesized at a low cost. Specific examples thereof include a phenyl group and a naphthyl group.

As the alkyl groups, ether groups, halogen atoms and halogenated alkyl groups, with which hydrogen atoms of the aryl group may be substituted, the same alkyl groups, ether groups, halogen atoms and halogenated alkyl groups as those mentioned above which the aryl group for $R^{7'''}$ to $R^{9'''}$ may have as a substituent can be used.

The alkyl group for $R^{1'''}$ to $R^{3'''}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

It is particularly desirable that each of $R^{1'''}$ to $R^{3'''}$ is a phenyl group or a naphthyl group.

When two of $R^{1'''}$ to $R^{3'''}$ in general formula (b-1) are bonded to each other to form a ring with the sulfur atom in the formula, it is preferable that the two of $R^{1'}$ to $R^{3'}$ form a 3 to 10-membered ring including the sulfur atom, and it is particularly desirable that the two of $R^{1'''}$ to $R^{3'''}$ form a 5 to 7-membered ring including the sulfur atom.

When two of $R^{1'''}$ to $R^{3'''}$ in general formula (b-1) are bonded to each other to form a ring with the sulfur atom in the formula, the remaining one of $R^{1'''}$ to $R^{3'''}$ is preferably an aryl group. As examples of the aryl group, the same as the above-mentioned aryl groups for $R^{1'''}$ to $R^{3'''}$ can be exemplified.

In general formula (b-2), $R^{5'''}$ and $R^{6'''}$ each independently represents an aryl group or an alkyl group. At least one of $R^{5'''}$ and $R^{6'''}$ represents an aryl group. It is preferable that both of $R^{5'''}$ and $R^{6'''}$ represent an aryl group.

As the aryl group for $R^{5'''}$ and $R^{6'''}$, the same as the aryl groups for $R^{1'''}$ to $R^{3'''}$ can be used.

As the alkyl group for $R^{5'''}$ and $R^{6'''}$, the same as the alkyl groups for $R^{1'''}$ to $R^{3'''}$ can be used.

It is particularly desirable that both of $R^{5'''}$ and $R^{6'''}$ represents a phenyl group.

As $R^{4'''}$ in general formula (b-2), the same as those mentioned above for $R^{4'''}$ in the aforementioned general formula (b-1) can be used.

Specific examples of suitable onium salt-based acid generators represented by general formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts is replaced by methanesulfonate, n-propanesulfonate, n-butanesulfonate, or n-octanesulfonate.

Further, onium salt-based acid generators in which the anion moiety in the aforementioned general formula (b-1) or (b-2) is replaced by an anion moiety represented by the aforementioned general formula (b-3) or (b-4) (the cation moiety is the same as (b-1) or (b-2)) may also be used.

Furthermore, as an onium salt-based acid generator, a sulfonium salt having a cation moiety represented by general formula (b-5) or (b-6) shown below may also be used.

[Chemical Formula 53]

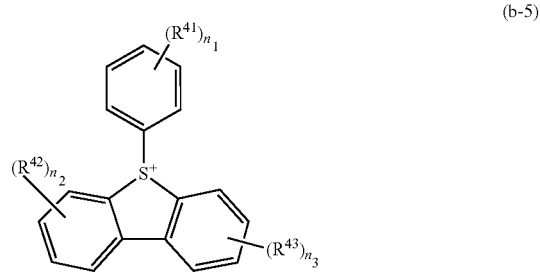

(b-5)

-continued

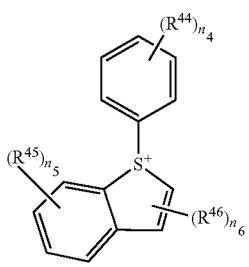
(b-6)

wherein $R^{41}$ to $R^{46}$ each independently represents an alkyl group, an acetyl group, an alkoxy group, a carboxyl group, a hydroxyl group or a hydroxyalkyl group; n1 to n5 each independently represents an integer of 0 to 3; and n6 represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, an ethyl group, a propyl group, an isopropyl group, an n-butyl group or a tert-butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably an aforementioned alkyl group in which one or more hydrogen atoms have been substituted with hydroxy groups, and examples thereof include a hydroxymethyl group, a hydroxyethyl group and a hydroxypropyl group.

When the subscripts $n_1$ to $n_6$ of $R^{41}$ to $R^{46}$ represent an integer of 2 or more, the plurality of $R^{41}$ to $R^{46}$ may be the same or different from each other.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5) or (b-6) is not particularly limited, and the same anion moieties as those used within previously proposed onium salt-based acid generators may be used. Examples of such anion moieties include fluorinated alkylsulfonate ions such as anion moieties ($R^{4"}SO_3^-$) for onium salt-based acid generators represented by general formula (b-1) or (b-2) shown above; and anion moieties represented by general formula (b-3) or (b-4) shown above. Among these, a fluorinated alkylsulfonate ion is preferable, a fluorinated alkylsulfonate ion of 1 to 4 carbon atoms is more preferable, and a linear perfluoroalkylsulfonate ion of 1 to 4 carbon atoms is particularly desirable. Specific examples thereof include a trifluoromethylsulfonate ion, a heptafluoro-n-propylsulfonate ion and a nonafluoro-n-butylsulfonate ion.

In the present description, an oxime sulfonate-based acid generator is a compound having at least one group represented by general formula (B-1) shown below, and has a feature of generating acid by irradiation. Such oxime sulfonate-based acid generators are widely used for a chemically amplified resist composition, and can be selected as appropriate.

[Chemical Formula 54]

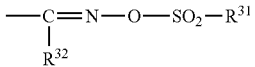
(B-1)

wherein $R^{31}$ and $R^{32}$ each independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, or a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "having a substituent" means that some or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, a partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, an aryl group, or a cyano group is preferable. Examples of the alkyl group and the aryl group for $R^{32}$ are the same as those of the alkyl group and the aryl group for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below

[Chemical Formula 55]

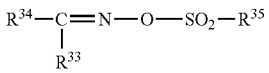
(B-2)

Wherein $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 56]

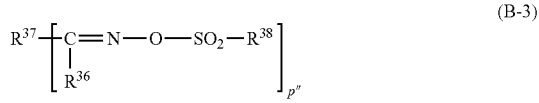
(B-3)

wherein $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2) above, the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably have 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, and still more preferably 90% or more. A completely fluorinated alkyl group in which 100% of the hydrogen atoms are substituted with fluorine atoms is particularly desirable.

In general formula (B-3) above, the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same alkyl groups having no substituent or the halogenated alkyl groups mentioned above for $R^{35}$ can be used.

P" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichloro cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described on pages 65 to 85) may be preferably used.

Furthermore, as preferable examples, the following can be exemplified.

[Chemical Formula 57]

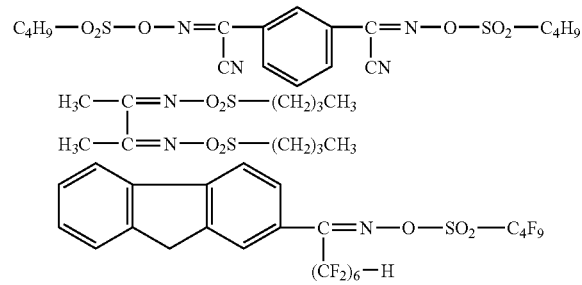

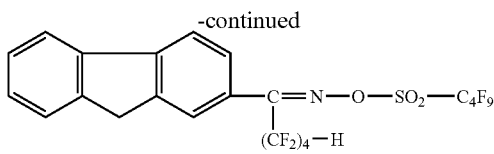

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may also be used favorably.

Furthermore, as examples of poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be given.

As the component (B2), any one type of these acid generators may be used alone, or two or more types may be used in combination.

Of these, as the component (B2), an onium salt-based acid generator having an anion in which the aforementioned $R^{4''}$ represents a fluorinated alkyl group which may have a substituent (namely, a fluorinated alkylsulfonate ion which may have a substituent) is preferable. An onium salt-based acid generator in which $Y^1$ in the aforementioned general formula (x-11) represents a fluorinated alkylene group of 1 to 4 carbon atoms which may have a substituent is particularly desirable.

When the component (B2) is included in the component (B), the amount of the component (B2) within the component (B) is preferably 10 to 90% by weight, and more preferably 50 to 75% by weight.

The ratio (molar ratio) between the blend quantities of the component (B1) and the component (B2) within the component (B) is preferably within a range from (B1):(B2)=9:1 to 1:9, more preferably from 4:1 to 1:4, and still more preferably from 1:1 to 1:3.

The total amount of the component (B) within the resist composition of the present invention is preferably from 0.5 to 50 parts by weight, and more preferably from 1 to 40 parts by weight, relative to 100 parts by weight of the component (A). When the amount of the component (B) is within the abovementioned range, formation of a resist pattern can be satisfactorily performed. Further, by virtue of the above-mentioned range, a uniform solution can be obtained and the storage stability becomes satisfactory.

<Component (C)>

There are no particular limitations on the component (C), which may be selected appropriately from the various cross-linking agents used within conventional chemically amplified negative resist compositions.

Specific examples include aliphatic cyclic hydrocarbons containing a hydroxyl group and/or a hydroxyalkyl group, or oxygen-containing derivatives thereof, such as 2,3-dihydroxy-5-hydroxymethylnorbornane, 2-hydroxy-5,6-bis(hydroxymethyl)norbornane, cyclohexanedimethanol, 3,4,8 (or 9)-trihydroxytricyclodecane, 2-methyl-2-adamantanol, 1,4-dioxane-2,3-diol, and 1,3,5-trihydroxycyclohexane.

Furthermore, other suitable examples include compounds produced by reacting an amino group-containing compound such as melamine, acetoguanamine, benzoguanamine, urea, ethylene urea, propylene urea or glycoluril with either formaldehyde or a combination of formaldehyde and a lower alcohol of 1 to 5 carbon atoms, thereby substituting the hydrogen atoms of the amino group with hydroxymethyl groups or lower alkoxymethyl groups of 1 to 5 carbon atoms; and compounds having an epoxy group.

Of these, compounds that use melamine are referred to as melamine-based cross-linking agents, compounds that use urea are referred to as urea-based cross-linking agents, compounds that use an alkylene urea such as ethylene urea or propylene urea are referred to as alkylene urea-based cross-linking agents, compounds that use glycoluril are referred to as glycoluril-based cross-linking agents, and compounds that use a compound having an epoxy group are referred to as epoxy-based cross-linking agents.

As the component (C), at least one type of cross-linking agent selected from the group consisting of melamine-based cross-linking agents, urea-based cross-linking agents, alkylene urea-based cross-linking agents, glycoluril-based cross-linking agents and epoxy-based cross-linking agents is preferred, and a glycoluril-based cross-linking agent is particularly desirable.

Examples of the melamine-based cross-linking agents include compounds obtained by reacting melamine with formaldehyde, thereby substituting the hydrogen atoms of the amino group with hydroxymethyl groups, and compounds obtained by reacting melamine with formaldehyde and a lower alcohol of 1 to 5 carbon atoms, thereby substituting the hydrogen atoms of the amino group with lower alkoxymethyl groups of 1 to 5 carbon atoms. Specific examples include hexamethoxymethylmelamine, hexaethoxymethylmelamine, hexapropoxymethylmelamine and hexabutoxybutylmelamine, and of these, hexamethoxymethylmelamine is preferred.

Examples of the urea-based cross-linking agents include compounds obtained by

Examples of the urea-based cross-linking agents include compounds obtained by reacting urea with formaldehyde, thereby substituting the hydrogen atoms of the amino group with hydroxymethyl groups, and compounds obtained by reacting urea with formaldehyde and a lower alcohol of 1 to 5 carbon atoms, thereby substituting the hydrogen atoms of the amino group with lower alkoxymethyl groups of 1 to 5 carbon atoms. Specific examples include bismethoxymethylurea, bisethoxymethylurea, bispropoxymethylurea and bisbutoxymethylurea, and of these, bismethoxymethylurea is preferred.

Examples of the alkylene urea-based cross-linking agents include compounds represented by general formula (C-1) shown below.

[Chemical Formula 58]

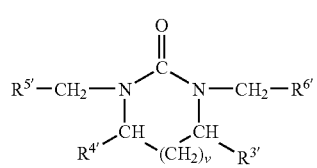

(C-1)

wherein $R^{5'}$ and $R^{6'}$ each independently represents a hydroxyl group or a lower alkoxy group, $R^{3'}$ and $R^{4'}$ each independently represents a hydrogen atom, a hydroxyl group or a lower alkoxy group, and v represents 0 or an integer of 1 to 2.

The lower alkoxy group for $R^{5'}$ and $R^{6'}$ may be either a linear or branched group, and is preferably an alkoxy group of 1 to 4 carbon atoms. $R^{5'}$ and $R^{6'}$ may be either the same or different, and are preferably the same.

The lower alkoxy group for $R^{3'}$ and $R^{4'}$ may be either a linear or branched group, and is preferably an alkoxy group of 1 to 4 carbon atoms. $R^{3'}$ and $R^{4'}$ may be either the same or different, and are preferably the same.

v is either 0 or an integer of 1 or 2, and is preferably 0 or 1.

As the alkylene urea-based cross-linking agent, compounds in which v is 0 (ethylene urea-based cross-linking agents) and/or compounds in which v is 1 (propylene urea-based cross-linking agents) are preferred.

Compounds represented by general formula (C-1) above can be obtained by a condensation reaction between an alkylene urea and formalin, and by further reacting the resulting product with a lower alcohol of 1 to 5 carbon atoms.

Specific examples of the alkylene urea-based cross-linking agents include ethylene urea-based cross-linking agents such as mono- and/or di-hydroxymethylated ethylene urea, mono- and/or di-methoxymethylated ethylene urea, mono- and/or di-ethoxymethylated ethylene urea, mono- and/or di-propoxymethylated ethylene urea, and mono- and/or di-butoxymethylated ethylene urea; propylene urea-based cross-linking agents such as mono- and/or di-hydroxymethylated propylene urea, mono- and/or di-methoxymethylated propylene urea, mono- and/or di-ethoxymethylated propylene urea, mono- and/or di-propoxymethylated propylene urea, and mono- and/or di-butoxymethylated propylene urea; as well as 1,3-di(methoxymethyl)-4,5-dihydroxy-2-imidazolidinone, and 1,3-di(methoxymethyl)-4,5-dimethoxy-2-imidazolidinone.

Examples of the glycoluril-based cross-linking agents include glycoluril derivatives in which the N-position is substituted with either one or both of a hydroxyalkyl group and an alkoxyalkyl group of 1 to 4 carbon atoms. These glycoluril derivatives can be obtained by a condensation reaction between glycoluril and formalin, and by further reacting the resulting product with a lower alcohol of 1 to 5 carbon atoms.

Specific examples of glycoluril-based cross-linking agents include mono-, di-, tri-, and/or tetra-hydroxymethylated glycoluril; mono-, di-, tri-, and/or tetra-methoxymethylated glycoluril; mono-, di-, tri-, and/or tetra-ethoxymethylated glycoluril; mono-, di-, tri-, and/or tetra-propoxymethylated glycoluril; and mono-, di-, tri-, and/or tetra-butoxymethylated glycoluril.

There are no particular limitations on the epoxy-based cross-linking agents, and any cross-linking agent having an epoxy group may be used. Of such cross-linking agents, those having two or more epoxy groups are preferred. Including two or more epoxy groups improves the cross-linking reaction.

The number of epoxy groups is preferably at least two, more preferably from 2 to 4, and is most preferably 2.

Preferred examples of the epoxy-based cross-linking agents are shown below.

[Chemical Formula 59]

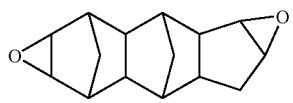

-continued

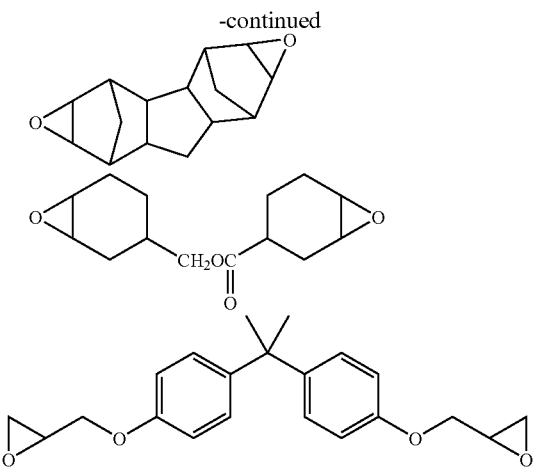

As the component (C), one type of cross-linking agent may be used alone, or two or more types may be used in combination.

The quantity of the component (C) is preferably within a range from 1 to 50 parts by weight, more preferably from 3 to 30 parts by weight, still more preferably from 3 to 15 parts by weight, and most preferably from 5 to 10 parts by weight, relative to 100 parts by weight of the component (A). By ensuring that the quantity of the component (C) is at least as large as the lower limit of the above-mentioned range, the formation of cross-linking is able to proceed favorably, and a favorable resist pattern with minimal swelling is obtained. On the other hand, by ensuring that the quantity is not more than the upper limit of the above-mentioned range, the storage stability of the resist coating liquid improves, and deterioration over time in the sensitivity can be suppressed.

<Component (F)>

In the resist composition of the present invention, the fluorine-containing compound (F) (namely, component (F)) is not particularly limited and may be either a polymeric compound (a polymer or copolymer) including a recurring unit, or a low molecular weight compound (a non-polymer).

In the resist composition of the present invention, by including the component (F), the hydrophobicity of the surface of the resist film improves, yielding a resist composition that is ideal also for immersion exposure.

Examples of the polymeric compounds (polymers or copolymers) used as the component (F) include a polymeric compound having a recurring unit that contains a fluorine atom. More specifically, a polymeric compound including one or more recurring units that contain a fluorine atom; and a polymeric compound including recurring units composed of a structural unit containing a fluorine atom and a structural unit with no fluorine atom, can be mentioned.

Further, examples of the low molecular weight compounds (non-polymers) used as the component (F) include a monomer for deriving structural units containing a fluorine atom which constitute the aforementioned polymeric compounds (polymers or copolymers).

Among these, the component (F) is preferably a polymeric compound (a polymer or copolymer).

—Structural Unit Containing a Fluorine Atom (Structural Unit (f1))

The structural unit containing a fluorine atom (hereafter, referred to as "structural unit (f1)") is not particularly limited as long as it is a structural unit containing a fluorine atom. For example, in the structural unit, a fluorine atom may be included within the side chain or may be directly bonded to the main chain, or a fluorine atom may be included in a substituent which is directly bonded to the main chain.

Of these various possibilities, as the structural unit (f1), a structural unit containing a fluorine atom within the side chain thereof is preferable. Specific examples include a structural unit having a group represented by general formula (f1-1-0) shown below; a structural unit having an acid dissociable, dissolution inhibiting group that contains a fluorine atom; and a structural unit having a non-acid dissociable fluorinated alkyl group of 1 to 20 carbon atoms.

[Chemical Formula 60]

(f1-1-0)

wherein $R^8$ represents an organic group having a fluorine atom; with the proviso that the carbon atom within a —C(=O)— moiety is not directly bonded to the main chain. (Structural Unit Having a Group Represented by General Formula (f1-1-0))

In the general formula (f1-1-0) above, $R^8$ represents an organic group having a fluorine atom.

An "organic group" is a group containing at least one carbon atom.

In the organic group having a fluorine atom for $R^8$, the structure of $R^8$ may be linear, branched or cyclic, and is preferably linear or branched.

With respect to $R^8$, the organic group preferably has 1 to 20 carbon atoms, more preferably 1 to 15 carbon atoms, still more preferably 1 to 10 carbon atoms, and most preferably 1 to 5 carbon atoms.

With respect to $R^8$, the fluorination ratio of the organic group is preferably 25% or more, more preferably 50% or more, and most preferably 60% or more, as the hydrophobicity of the resist film is enhanced.

The term "fluorination ratio" refers to the ratio (%) of the number of fluorine atoms relative to the total number of hydrogen atoms and fluorine atoms contained within the organic group.

More specifically, preferred examples of $R^8$ include a fluorinated hydrocarbon group which may have a substituent.

In the fluorinated hydrocarbon group, the hydrocarbon group (a hydrocarbon group which is not fluorinated) may be either an aliphatic hydrocarbon group or an aromatic hydrocarbon group, and an aliphatic hydrocarbon group is preferable.

An aliphatic hydrocarbon group refers to a hydrocarbon group having no aromaticity. The aliphatic hydrocarbon group may be either saturated or unsaturated, but in general, the aliphatic hydrocarbon group is preferably saturated.

As $R^8$, a fluorinated, saturated hydrocarbon group or a fluorinated, unsaturated hydrocarbon group is preferable, more preferably a fluorinated, saturated hydrocarbon group, and most preferably a fluorinated alkyl group.

Examples of fluorinated alkyl groups include groups in which part or all of the hydrogen atoms within the below described unsubstituted alkyl groups (groups which do not have a substituent described later) have been substituted with a fluorine atom.

The fluorinated alkyl group may be either a group in which part of the hydrogen atoms within an unsubstituted alkyl group described below has been substituted with a fluorine atom, or a group in which all of the hydrogen atoms within an unsubstituted alkyl group described below have been substituted with a fluorine atom (i.e., a perfluoroalkyl group).

The unsubstituted alkyl group may be any of linear, branched or cyclic. Alternatively, the unsubstituted alkyl group may be a combination of a linear or branched alkyl group with a cyclic alkyl group.

The unsubstituted linear alkyl group preferably has 1 to 10 carbon atoms, and more preferably 1 to 8 carbon atoms. Specific examples include a methyl group, an ethyl group, an n-propyl group, an n-butyl group, an n-pentyl group, an n-hexyl group, an n-heptyl group, an n-octyl group, an n-nonyl group and an n-decanyl group.

The unsubstituted branched alkyl group preferably has 3 to 10 carbon atoms, and more preferably 3 to 8 carbon atoms. As the branched alkyl group, a tertiary alkyl group is preferable.

As an example of an unsubstituted cyclic alkyl group, a group in which one hydrogen atom has been removed from a monocycloalkane or a polycycloalkane such as a bicycloalkane, tricycloalkane or tetracycloalkane can be given. Specific examples include monocycloalkyl groups such as a cyclopentyl group and a cyclohexyl group; and polycycloalkyl groups such as an adamantyl group, a norbornyl group, an isobornyl group, a tricyclodecanyl group and a tetracyclododecanyl group.

Examples of the combination of a linear or branched alkyl group with a cyclic alkyl group include groups in which a cyclic alkyl group as a substituent is bonded to a linear or branched alkyl group, and groups in which a linear or branched alkyl group as a substituent is bonded to a cyclic alkyl group.

Examples of substituents which the fluorinated hydrocarbon group may have include an alkyl group of 1 to 5 carbon atoms.

As the fluorinated alkyl group for $R^8$, a linear or branched fluorinated alkyl group is preferable. In particular, a group represented by general formula (VII-1) or (VII-2) shown below is desirable, and a group represented by general formula (VII-1) is most preferable.

[Chemical Formula 61]

(VII-1)

(VII-2)

[In general formula (VII-1), $R^{41'}$ represents an unsubstituted alkylene group of 1 to 9 carbon atoms; and $R^{42'}$ represents a fluorinated alkyl group of 1 to 9 carbon atoms, with the provision that the total number of carbon atoms of $R^{41'}$ and $R^{42'}$ is no more than 10. In general formula (VII-2), each of $R^{81}$ to $R^{83}$ independently represents a linear alkyl group of 1 to 5 carbon atoms, with the provision that at least one of $R^{81}$ to $R^{83}$ represents an alkyl group having a fluorine atom.

In general formula (VII-1), the alkylene group for $R^{41'}$ may be linear, branched or cyclic, and is preferably linear or branched. Further, the number of carbon atoms within the alkylene group is preferably within a range of from 1 to 5.

As $R^{41'}$, a methylene group, an ethylene group or a propylene group is particularly desirable.

As $R^{42'}$, a linear or branched fluorinated alkyl group of 1 to 5 carbon atoms is preferable, and a perfluoroalkyl group is particularly desirable. Of such groups, a trifluoromethyl group and a pentafluoroethyl group are particularly preferred.

In general formula (VII-2), as the alkyl group for $R^{81}$ to $R^{83}$, an ethyl group or a methyl group is preferable, and a methyl group is particularly desirable. At least one of the alkyl groups for $R^{81}$ to $R^{83}$ is a fluorinated alkyl group, and all of the alkyl groups for $R^{81}$ to $R^{83}$ may be fluorinated alkyl groups.

In the aforementioned formula (f1-1-0), the carbon atom within a —C(=O)— portion is not directly bonded to the main chain. As a result, the group "—O—$R^8$" may dissociate satisfactorily by the action of an alkali developing solution which is weakly basic.

In other words, the group "—O—$R^8$" dissociates from a group represented by the aforementioned general formula (f1-1-0) due to hydrolysis caused by the action of an alkali developing solution. Therefore, in the group represented by the aforementioned general formula (f1-1-0), a hydrophilic group [—C(=O)—OH] is formed when the group "—O—$R^8$" dissociates. Accordingly, the hydrophilicity of the component (F) is enhanced, and hence, the compatibility of the component (F) with the alkali developing solution is improved. As a result, the hydrophilicity of the resist film surface is enhanced during developing.

In the resist composition of the present invention, as the structural unit (f1), a structural unit (f1-1) represented by general formula (f1-1-1) shown below can be mentioned as a preferred example, because favorable solubility of the composition in organic solvents can be achieved, and the hydrophobicity of the surface of the resist film can be enhanced.

[Chemical Formula 62]

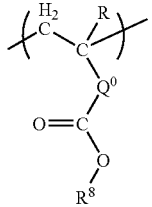

(f1-1-1)

wherein R represents a hydrogen atom, a lower alkyl group of 1 to 5 carbon atoms or a halogenated lower alkyl group of 1 to 5 carbon atoms; $Q^0$ represents a single bond or a divalent linking group; and $R^8$ represents an organic group having a fluorine atom.

—Structural Unit (f1-1)

The structural unit (f1-1) is a structural unit represented by the aforementioned general formula (f1-1-1).

In the aforementioned general formula (f1-1-1), R represents a hydrogen atom, a lower alkyl group of 1 to 5 carbon atoms or a halogenated lower alkyl group of 1 to 5 carbon atoms.

The lower alkyl group and halogenated lower alkyl group for R are the same as the lower alkyl group and halogenated lower alkyl group which may be bonded to the α-position of the aforementioned acrylate ester.

In the aforementioned formula (f1-1-1), $Q^0$ represents a single bond or a divalent linking group.

Preferred examples of the divalent linking group for $Q^0$ include a hydrocarbon group which may have a substituent, and a group containing a hetero atom.

(Hydrocarbon Group which May have a Substituent)

With respect to the divalent linking group for $Q^0$, the description that the hydrocarbon group may "have a substituent" means that some or all of the hydrogen atoms of the hydrocarbon group may be substituted with groups or atoms other than hydrogen atoms.

The hydrocarbon group for $Q^0$ may be either an aliphatic hydrocarbon group, or an aromatic hydrocarbon group.

Here, an aliphatic hydrocarbon group refers to a hydrocarbon group that has no aromaticity. The aliphatic hydrocarbon group may be either saturated or unsaturated, but in general, the aliphatic hydrocarbon group is preferably saturated.

Specific examples of aliphatic cyclic groups include a linear or branched aliphatic hydrocarbon group and an aliphatic hydrocarbon group containing a ring in the structure thereof.

The linear or branched aliphatic hydrocarbon group for $Q^0$ preferably has 1 to 10 carbon atoms, more preferably 1 to 8 carbon atoms, still more preferably 1 to 5 carbon atoms, and most preferably 1 to 3 carbon atoms.

As the linear aliphatic hydrocarbon group, linear alkylene groups are preferred, and specific examples include a methylene group, an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; alkylethylene groups such as —CH($CH_3$)$CH_2$—, —CH($CH_3$)CH($CH_3$)—, —C($CH_3$)$_2CH_2$—, —CH($CH_2CH_3$)$CH_2$— and —C($CH_2CH_3$)$_2$—$CH_2$; alkyltrimethylene groups such as —CH($CH_3$)$CH_2CH_2$— and —$CH_2$CH($CH_3$)$CH_2$—; and alkyltetramethylene groups such as —CH($CH_3$)$CH_2CH_2CH_2$— and —$CH_2$CH($CH_3$)$CH_2CH_2$—. As the alkyl group within the alkylalkylene group, a linear alkyl group of 1 to 5 carbon atoms is preferable.

The linear or branched (chain-like) aliphatic hydrocarbon group may or may not have a substituent. Examples of the substituent include a fluorine atom, a fluorinated lower alkyl group of 1 to 5 carbon atoms which is substituted by a fluorine atom, and an oxygen atom (=O).

Examples of aliphatic hydrocarbon groups containing a ring, for $Q^0$, include a cyclic aliphatic hydrocarbon group (an aliphatic hydrocarbon ring having 2 hydrogen atoms removed therefrom), a group in which the cyclic aliphatic hydrocarbon group is bonded to the terminal of the aforementioned chain-like aliphatic hydrocarbon group, and a group in which the cyclic aliphatic hydrocarbon group is positioned partway along the chain-like aliphatic hydrocarbon group.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group.

As the monocyclic group, a group in which two or more hydrogen atoms have been removed from a monocycloalkane of 3 to 6 carbon atoms is preferable. Examples of the monocycloalkane include cyclopentane and cyclohexane.

As the polycyclic group, a group in which two or more hydrogen atoms have been removed from a polycycloalkane of 7 to 12 carbon atoms is preferable. Specific examples of the polycycloalkane include adamantane, norbornane, isobornane, tricyclodecane and tetracyclododecane.

The cyclic aliphatic hydrocarbon groups may or may not have a substituent.

Examples of substituents include a lower alkyl group of 1 to 5 carbon atoms, a fluorine atom, a fluorinated lower alkyl group of 1 to 5 carbon atoms which is substituted by a fluorine atom, and an oxygen atom (=O).

Examples of aromatic hydrocarbon groups for $Q^0$ include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group;

an aromatic hydrocarbon group in which a part of the carbon atoms constituting the ring of the aforementioned divalent aromatic hydrocarbon group has been substituted with a hetero atom such as an oxygen atom, a sulfur atom or a nitrogen atom;

and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

Among these examples, the aforementioned divalent aromatic hydrocarbon group is preferable, and an aromatic hydrocarbon group in which one hydrogen atom has been removed from a phenyl group, or an aromatic hydrocarbon group in which one hydrogen atom has been removed from a naphthyl group is particularly desirable.

The alkyl chain within the arylalkyl group preferably has 1 to 4 carbon atoms, more preferably 1 or 2 carbon atoms, and most preferably 1 carbon atom.

The aromatic hydrocarbon group may or may not have a substituent. Examples of substituents include a lower alkyl group of 1 to 5 carbon atoms, a fluorine atom, a fluorinated lower alkyl group of 1 to 5 carbon atoms which is substituted by a fluorine atom, and an oxygen atom (=O).

Among the above-mentioned examples, as the hydrocarbon group which may have a substituent, a linear, branched or cyclic aliphatic hydrocarbon group or a divalent aromatic hydrocarbon group is preferable, and a methylene group, an ethylene group, —CH(CH$_3$)—, a group in which one hydrogen atom has been removed from a tetracyclododecanyl group, or an aromatic hydrocarbon group in which one hydrogen atom has been removed from a phenyl group is particularly desirable.

(Group Containing a Hetero Atom)

A hetero atom refers to an atom other than a carbon atom and a hydrogen atom, and examples thereof include an oxygen atom, a nitrogen atom, a sulfur atom and a halogen atom. Examples of groups containing a hetero atom include —O—, —C(=O)—, —C(=O)—O—, a carbonate bond (—O—C(=O)—O—), —NH—, —NR$^{05}$— (wherein R$^{05}$ represents an alkyl group), —NH—C(=O)—, =N—, and a combination of any of these "groups" with a divalent hydrocarbon group.

As the divalent hydrocarbon group, the same groups as those described above for the hydrocarbon group which may have a substituent can be used, and a linear or branched aliphatic hydrocarbon group is preferable.

Among the above-mentioned examples, as the group containing a hetero atom, a combination of any of the aforementioned "groups" with a divalent hydrocarbon group is preferable. More specifically, it is particularly desirable to use a combination of any of the aforementioned "groups" with the aforementioned aliphatic hydrocarbon group, or a combination of the aforementioned aliphatic hydrocarbon group, any of the aforementioned "groups" and the aforementioned aliphatic hydrocarbon group.

In the formula (f1-1-1) above, R$^8$ represents an organic group having a fluorine atom, and is the same as R$^8$ in the above-mentioned formula (f1-1-0).

Preferred examples of the structural unit (f1-1) include structural units represented by general formula (f1-1-10) or (f1-1-20) shown below.

[Chemical Formula 63]

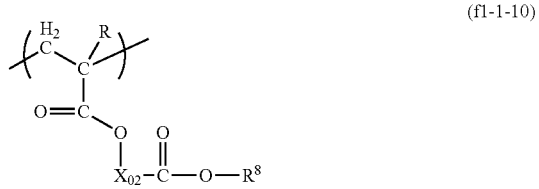

(f1-1-10)

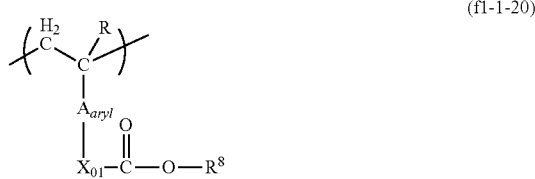

(f1-1-20)

wherein each R independently represents a hydrogen atom, a lower alkyl group of 1 to 5 carbon atoms or a halogenated lower alkyl group of 1 to 5 carbon atoms; $X_{02}$ represents a divalent organic group; $A_{aryl}$ represents a divalent aromatic cyclic group which may have a substituent; $X_{01}$ represents a single bond or a divalent linking group; and each R$^8$ independently represents an organic group having a fluorine atom.

In formulas (f1-1-10) and (f1-1-20), R$^8$ is the same as R$^8$ defined in the above-mentioned formula (f1-1-1).

In formulas (f1-1-10) and (f1-1-20), as R$^8$, a fluorinated hydrocarbon group is preferable, a fluorinated alkyl group is more preferable, a fluorinated alkyl group of 1 to 5 carbon atoms is still more preferable, and —CH$_2$—CF$_3$, —CH$_2$—CF$_2$—CF$_3$, —CH(CF$_3$)$_2$, —CH$_2$—CF$_2$—CF$_2$—CF$_3$, —CH$_2$—CH$_2$—CF$_2$—CF$_2$—CF$_3$ and —CH$_2$—CH$_2$—CF$_2$—CF$_2$—CF$_2$—CF$_3$ are most preferable.

As the lower alkyl group for R, a linear or branched lower alkyl group is preferable, and specific examples of lower alkyl groups include a methyl group, an ethyl group, a propyl group, an isopropyl group, an n-butyl group, an isobutyl group, a tert-butyl group, a pentyl group, an isopentyl group and a neopentyl group.

Specific examples of the halogenated lower alkyl group include groups in which part or all of the hydrogen atoms of the aforementioned "lower alkyl group" have been substituted with a halogen atom. Examples of the halogen atom include a fluorine atom, a chlorine atom, a bromine atom and an iodine atom, and a fluorine atom is particularly desirable.

In the present invention, as R, a hydrogen atom, a lower alkyl group or a fluorinated lower alkyl group is preferable, and a hydrogen atom or a methyl group is more preferable in terms of industrial availability.

In general formula (f1-1-10), $X_{02}$ represents a divalent organic group.

Preferred examples of $X_{02}$ include a hydrocarbon group which may have a substituent, and a group containing a hetero atom. They are the same as the hydrocarbon group which may have a substituent, and the group containing a hetero atom, respectively, which are described above in relation to the divalent linking group for $Q^0$.

In general formula (f1-1-20), $A_{aryl}$ represents a divalent aromatic cyclic group which may have a substituent. A specific example of $A_{aryl}$ includes an aromatic hydrocarbon ring (which may have a substituent) having 2 or more hydrogen atoms removed therefrom.

The ring skeleton of the aromatic cyclic group for $A_{aryl}$ preferably has 6 to 15 carbon atoms. Examples of ring skeletons include a benzene ring, a naphthalene ring, a phenanthrene ring and an anthracene ring. Among these, a benzene ring or a naphthalene ring is particularly desirable.

Examples of substituents which an aromatic cyclic group for $A_{aryl}$ may have include a halogen atom, an alkyl group, an alkoxy group, a halogenated lower alkyl group and an oxygen atom (=O). Examples of the halogen atom include a fluorine atom, a chlorine atom, an iodine atom and a bromine atom. As the substituent which an aromatic cyclic group for $A_{aryl}$ may have, a fluorine atom is preferable. As the alkyl group, the same lower alkyl groups as those described above for R can be mentioned. As the alkoxy group, alkoxy groups having 1 to 5 carbon atoms can be mentioned. As the halogenated lower alkyl group, the same halogenated lower alkyl groups as those described above for R can be mentioned.

$A_{aryl}$ may be either an aromatic cyclic group having no substituent, or an aromatic cyclic group having a substituent, although an aromatic cyclic group having no substituent is preferable.

When $A_{aryl}$ is an aromatic cyclic group having a substituent, the number of the substituent may be either 1, 2 or more, preferably 1 or 2, and more preferably 1.

In general formula (f1-1-20), $X^{01}$ represents a single bond or a divalent linking group.

Examples of divalent linking groups include an alkylene group of 1 to 10 carbon atoms, —O—, —C(=O)—, —C(=O)—O—, a carbonate bond (—O—C(=O)—O—), —NH—C(=O)—, and a combination of these groups, and a combination of —O— with an alkylene group of 1 to 10 carbon atoms or a combination of —C(=O)—O— with an alkylene group of 1 to 10 carbon atoms is more preferable.

Examples of alkylene groups of 1 to 10 carbon atoms include linear, branched or cyclic alkylene groups, and a linear or branched alkylene group of 1 to 5 carbon atoms and a cyclic alkylene group of 4 to 10 carbon atoms are preferable.

Among structural units represented by the aforementioned general formula (f1-1-10), structural units represented by general formulas (f1-1-11) to (f1-1-16) shown below are preferable.

Further, among structural units represented by the aforementioned general formula (f1-1-20), structural units represented by general formulas (f1-1-21) to (f1-1-26) shown below are preferable.

[Chemical Formula 64]

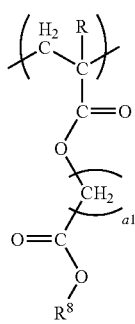

(f1-1-11)

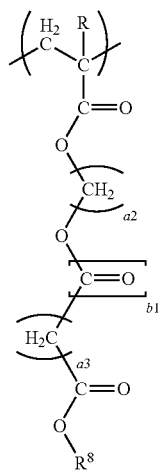

(f1-1-12)

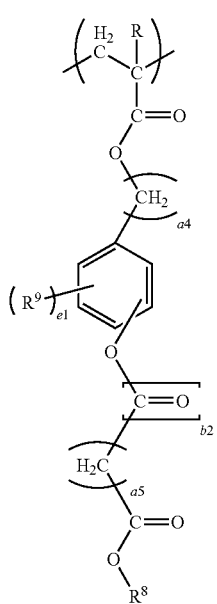

(f1-1-13)

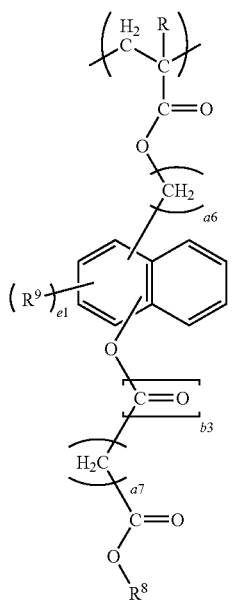

(f1-1-14)

[Chemical Formula 65]
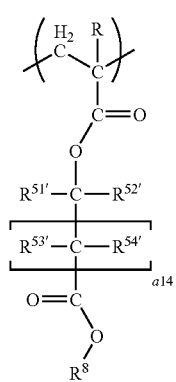
(f1-1-15)
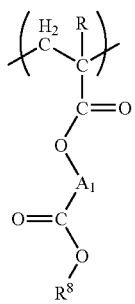
(f1-1-16)
[Chemical Formula 66]
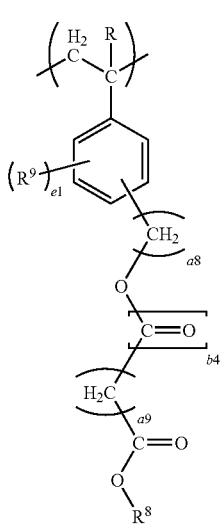
(f1-1-21)
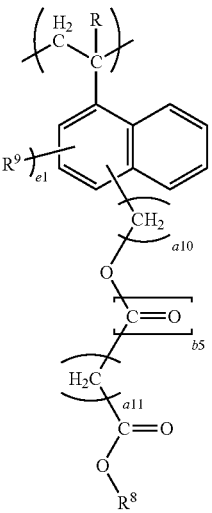
(f1-1-22)
(f1-1-23)
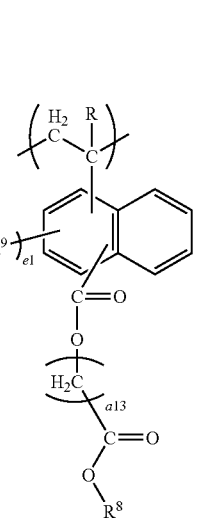
(f1-1-24)

-continued

[Chemical Formula 67]

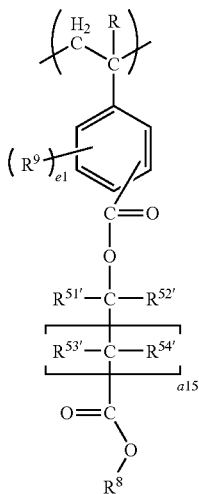

(f1-1-25)

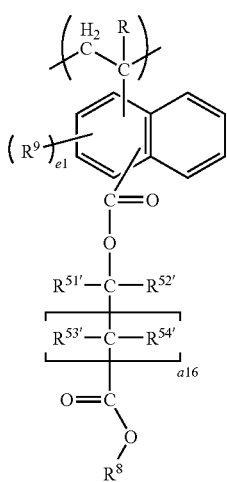

(f1-1-26)

In the above general formulas (f1-1-11) to (f1-1-16) and (f1-1-21) to (f1-1-26), R is the same as R in the above general formula (f1-1-10) or general formula (f1-1-20) and $R^8$ is the same as $R^8$ in the above general formula (f1-1-10) or general formula (f1-1-20); each of $R^{51'}$ and $R^{52'}$ independently represents an alkyl group of 1 to 10 carbon atoms; each of $R^{53'}$ and $R^{54'}$ independently represents a hydrogen atom or an alkyl group of 1 to 10 carbon atoms; each of a1, a2, a3, a5, a7 a9 and a11 to a13 independently represents an integer of 1 to 5; each of a4, a6, a8 and a10 independently represents an integer of 0 to 5; each of a14 to a16 independently represents an integer of 0 to 5; each of b1 to b5 independently represents 0 or 1; $R^9$ represents a substituent; e1 represents an integer of 0 to 2; and $A_1$ represents a cyclic alkylene group of 4 to 20 carbon atoms.

In formulas (f1-1-11) to (f1-1-16) and (f1-1-21) to (f1-1-26), as R, a hydrogen atom or a methyl group is preferable.

In formula (f1-1-11), a1 is preferably an integer of 1 to 3, and more preferably 1 or 2.

In formula (f1-1-12), it is preferable that each of a2 and a3 independently represent an integer of 1 to 3, and more preferably 1 or 2.

b1 is preferably 0.

In formula (f1-1-13), a4 is preferably an integer of 0 to 3, more preferably an integer of 0 to 2, and most preferably 0 or 1.

a5 is preferably an integer of 1 to 3, and more preferably 1 or 2.

As the substituent for $R^9$, for example, a halogen atom, a lower alkyl group, an alkoxy group of 1 to 5 carbon atoms, a halogenated lower alkyl group, or an oxygen atom (=O) can be used. As the lower alkyl group, the same lower alkyl groups as those described above for R can be mentioned. Examples of the halogen atom include a fluorine atom, a chlorine atom, an iodine atom and a bromine atom. As the halogenated lower alkyl group, the same halogenated lower alkyl groups as those described above for R can be mentioned.

e1 is preferably 0 or 1, and most preferably 0 from an industrial viewpoint.

b2 is preferably 0.

In formula (f1-1-14), a6 is preferably an integer of 0 to 3, more preferably an integer of 0 to 2, and most preferably 0 or 1.

a7 is preferably an integer of 1 to 3, and more preferably 1 or 2.

b3 is preferably 0.

$R^9$ and e1 are the same as $R^9$ and e1 in the aforementioned general formula (f1-1-13), respectively.

In formula (f1-1-15), a14 is preferably an integer of 0 to 3, more preferably an integer of 0 to 2, and most preferably 0 or 1.

It is preferable that each of $R^{51'}$ and $R^{52'}$ independently represent a linear, branched or cyclic alkyl group of 1 to 10 carbon atoms, and specific examples thereof include a methyl group, an ethyl group, an n-propyl group, an isopropyl group, an n-butyl group, an isobutyl group, a tert-butyl group, a tert-pentyl group, a cyclopentyl group, a cyclohexyl group, a cyclooctyl group, a norbornyl group, an isobornyl group, a tricyclodecanyl group, an adamantyl group and a tetracyclododecanyl group. Of these, an alkyl group of 1 to 6 carbon atoms is preferable, more preferably an alkyl group of 1 to 4 carbon atoms, and most preferably a methyl group or an ethyl group.

It is preferable that each of $R^{53'}$ and $R^{54'}$ independently represent a hydrogen atom, or a linear, branched or cyclic alkyl group of 1 to 10 carbon atoms. For $R^{53'}$ and $R^{54'}$, the linear, branched or cyclic alkyl group of 1 to 10 carbon atoms is the same linear, branched or cyclic alkyl groups of 1 to 10 carbon atoms as those described above for $R^{51'}$ and $R^{52'}$.

In formula (f1-1-16), $A_1$ represents a cyclic alkylene group of 4 to 20 carbon atoms, and is preferably a cyclic alkylene group of 5 to 15 carbon atoms, and more preferably a cyclic alkylene group of 6 to 12 carbon atoms. Specific examples of cyclic alkylene groups include those described above as the "cyclic aliphatic hydrocarbon group" for the aforementioned hydrocarbon group which may have a substituent, and the cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Specific examples of the polycycloalkane include adamantane, norbornane, isobornane, tricyclodecane and tetracyclododecane.

The cyclic aliphatic hydrocarbon groups may or may not have a substituent. Examples of substituents include a lower alkyl group of 1 to 5 carbon atoms, a fluorine atom, a fluorinated lower alkyl group of 1 to 5 carbon atoms which is substituted by a fluorine atom, and an oxygen atom (=O).

In formula (f1-1-21), a8 is preferably an integer of 0 to 3, more preferably an integer of 0 to 2, and most preferably 0 or 1.

a9 is preferably an integer of 1 to 3, and more preferably 1 or 2.

b4 is preferably 0.

$R^9$ and e1 are the same as $R^9$ and e1 in the aforementioned general formula (f1-1-13), respectively.

In formula (f1-1-22), a10 is preferably an integer of 0 to 3, more preferably an integer of 0 to 2, and most preferably 0 or 1.

a11 is preferably an integer of 1 to 3, and more preferably 1 or 2.

b5 is preferably 0.

$R^9$ and e1 are the same as $R^9$ and e1 in the aforementioned general formula (f1-1-13), respectively.

In formula (f1-1-23), a12 is preferably an integer of 1 to 3, and more preferably 1 or 2.

$R^9$ and e1 are the same as $R^9$ and e1 in the aforementioned general formula (f1-1-13), respectively.

In formula (f1-1-24), a13 is preferably an integer of 1 to 3, and more preferably 1 or 2.

$R^9$ and e1 are the same as $R^9$ and e1 in the aforementioned general formula (f1-1-13), respectively.

In formulas (f1-1-25) and (f1-1-26), each of a15 and a16 is preferably an integer of 0 to 3, more preferably an integer of 0 to 2, and most preferably 0 or 1.

$R^{51'}$, $R^{52'}$ $R^{53'}$ and $R^{54'}$ are the same as $R^{51'}$, $R^{52'}$, $R^{53'}$ and $R^{54'}$ in the aforementioned general formula (f1-1-15), respectively.

$R^9$ and e1 are the same as $R^9$ and e1 in the aforementioned general formula (f1-1-13), respectively.

Specific examples of structural units represented by the above general formulas (f1-1-11) to (f1-1-16) and (f1-1-21) to (f1-1-26) are shown below.

[Chemical Formula 68]

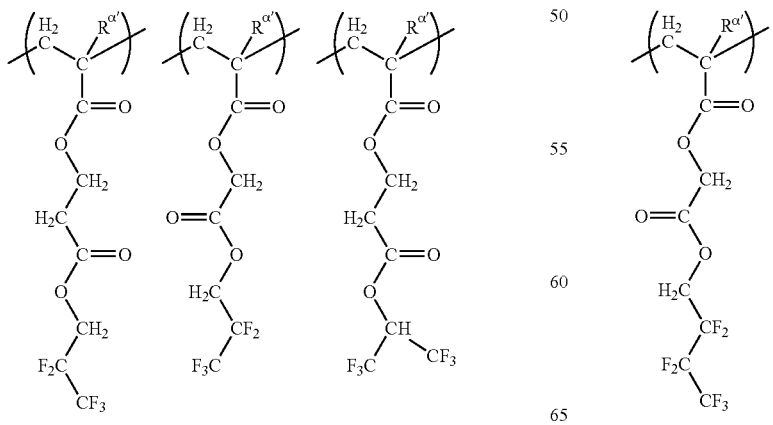

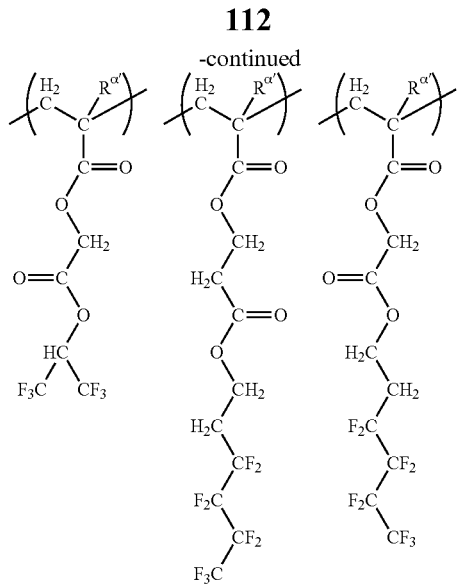

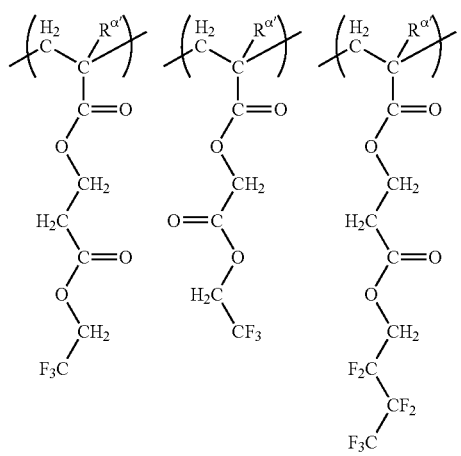

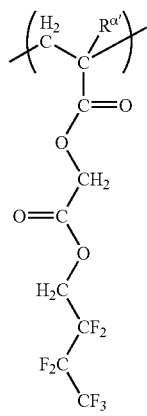

wherein $R^\alpha$ represents a hydrogen atom or a methyl group.

[Chemical Formula 69]
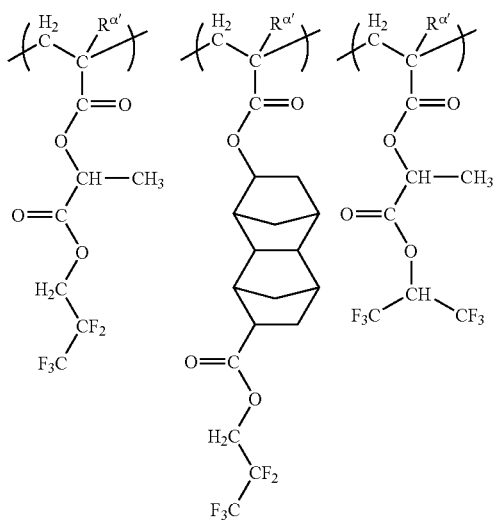
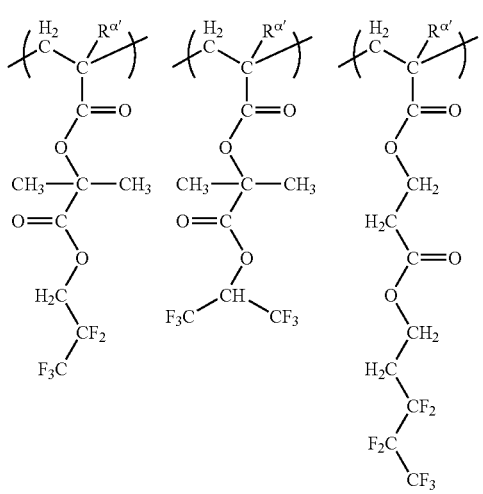
wherein $R^\alpha$ represents a hydrogen atom or a methyl group.
[Chemical Formula 70]
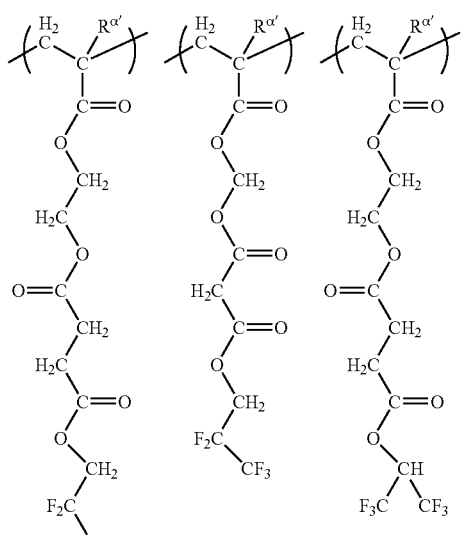
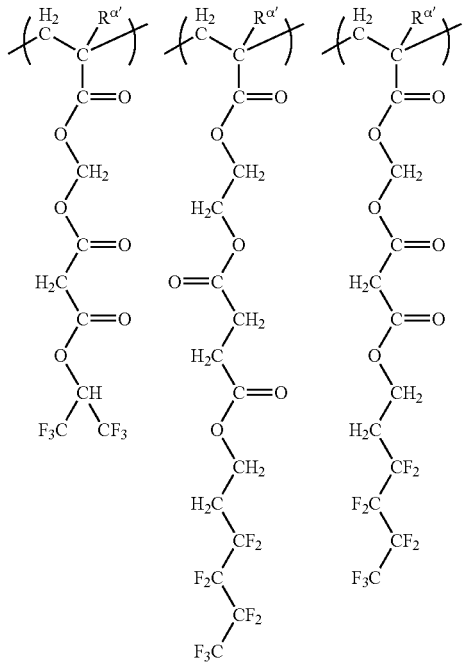
wherein $R^\alpha$ represents a hydrogen atom or a methyl group.

[Chemical Formula 71]
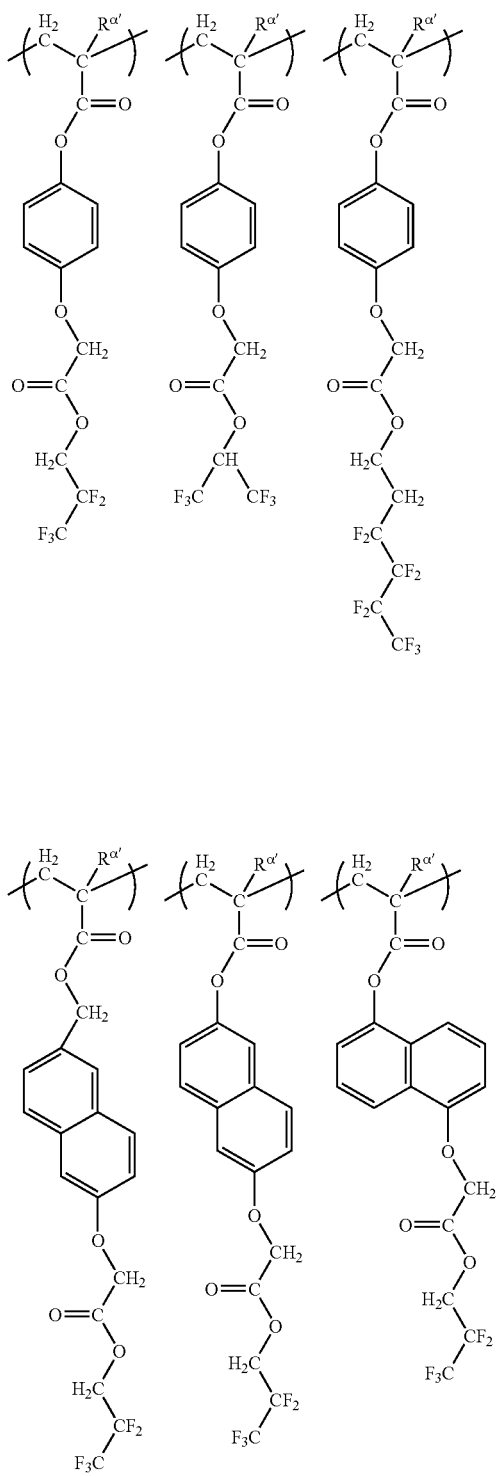
wherein $R^\alpha$ represents a hydrogen atom or a methyl group.
[Chemical Formula 72]
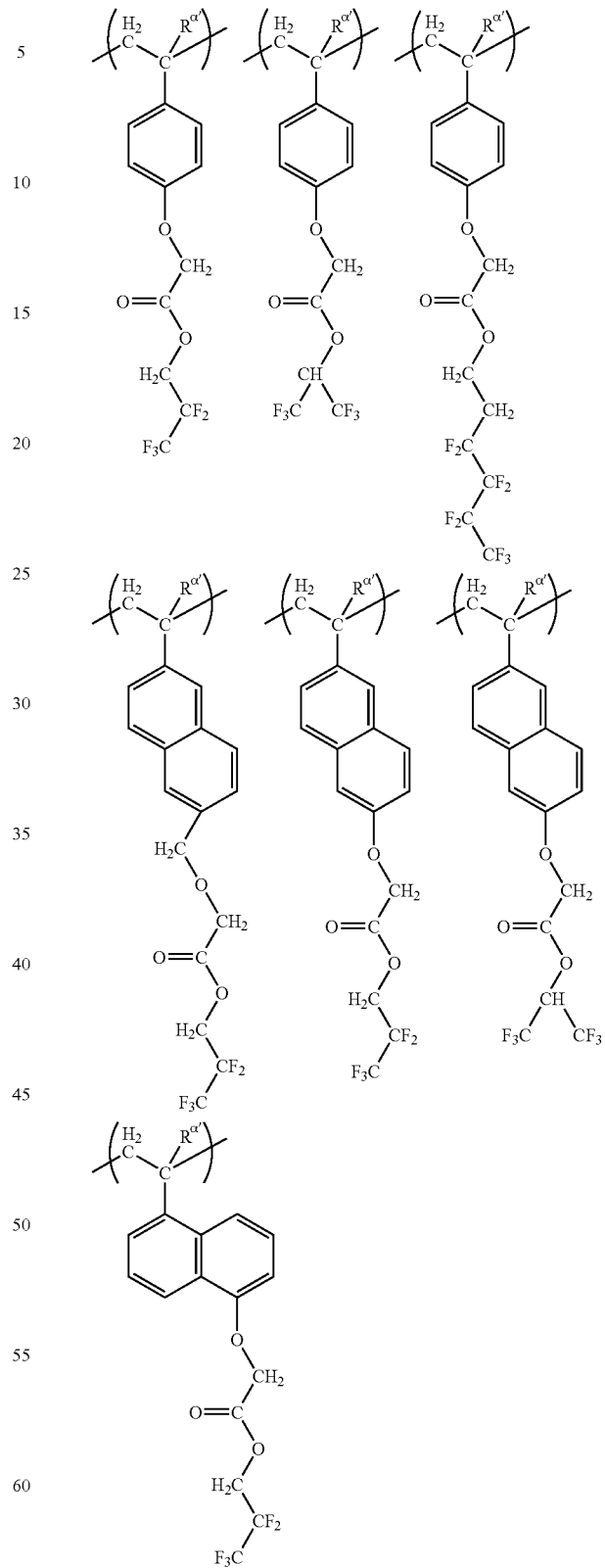
wherein $R^\alpha$ represents a hydrogen atom or a methyl group.

As the structural unit (f1-1), at least one structural unit selected from the group consisting of structural units represented by the aforementioned general formulas (f1-1-1) to (f1-1-16) and (f1-1-21) to (f1-1-26) is preferable, more preferably at least one structural unit selected from the group consisting of structural units represented by the aforementioned general formulas (f1-1-1) to (f1-1-13), (f1-1-21) and (f1-1-22), still more preferably at least one structural unit selected from the group consisting of structural units represented by the aforementioned general formulas (f1-1-11) and (f1-1-22), and most preferably structural units represented by the aforementioned general formula (f1-1-11).

In the component (F), as the structural unit (f1), one type of structural unit may be used alone, or two or more types may be used in combination.

In the component (F), the amount of the structural unit (f1) based on the combined total of all structural units constituting the component (F) is preferably 30 to 95 mol %, more preferably 40 to 90 mol %, and still more preferably 50 to 85 mol %.

When the amount of the structural unit (f1) is at least as large as the lower limit of the above-mentioned range, during resist pattern formation, the characteristic feature of enhancing hydrophobicity of the resist film is improved. On the other hand, when the amount of the structural unit (f1) is no more than the upper limit of the above-mentioned range, a good balance can be achieved with the other structural units.

When the structural unit (f1-1) is used as the structural unit (f1), in the component (F), the amount of the structural unit (f1-1) based on the combined total of all structural units constituting the component (F) is preferably 30 to 95 mol %, more preferably 40 to 90 mol %, and still more preferably 50 to 85 mol %. When the amount of the structural unit (f1-1) is at least as large as the lower limit of the above-mentioned range, the characteristic feature of enhancing hydrophobicity of the resist film is improved. On the other hand, when the amount of the structural unit (f1-1) is no more than the upper limit of the above-mentioned range, a good balance can be achieved with the other structural units.

—Other Structural Unit (Structural Unit (f2))

The component (F) may include a structural unit other than the structural unit (f1) (hereafter, referred to as "structural unit (f2)"), as long as the effects of the present invention are not impaired.

There are no particular limitations on the structural unit (f2), provided the structural unit is derived from a compound that is copolymerizable with the compound that gives rise to the structural unit (f1).

Examples of the structural unit (f2) include structural units which have been proposed for the base resin of a conventional chemically amplified resist (such as the aforementioned structural units (a1) to (a4) in the component (A1-1)). When used in a positive resist composition, the structural unit (a1) can be mentioned as a preferred example of the structural unit (f2).

In the component (F), as the structural unit (f2), one type of structural unit may be used alone, or two or more types may be used in combination.

For example, when the structural unit (a1) is used as the structural unit (f2), of the various structural units classified as the structural unit (a1), structural units represented by general formulas (a1-1) and (a1-3) are preferred, structural units represented by general formula (a1-1) are more preferred, and structural units represented by general formulas (a1-1-16) to (a1-1-23), (a1-1-27) and (a1-1-31) are particularly desirable.

In the component (F), the amount of the structural unit (a1) based on the combined total of all structural units constituting the component (F) is preferably 1 to 40 mol %, and more preferably 5 to 30 mol %.

By making the amount of the structural unit (a1) within the above-mentioned range, the water repellency is improved, and a good balance can be achieved with the other structural units.

In the resist composition of the present invention, the component (F) is preferably a polymeric compound that includes the structural unit (f1) (hereafter, referred to as "fluorine-containing resin (F1-1)").

Examples of such a fluorine-containing resin (F1-1) include a copolymer composed of the structural unit (f1) and the structural unit (f2). More specifically, a copolymer composed of the structural unit (f1) and the structural unit (a1) can be mentioned as a preferred example.

Among the above-mentioned examples, it is particularly desirable that the fluorine-containing resin (F1-1) be a copolymer composed of the structural unit (f1-1) and the structural unit (a1).

In the component (F), as the fluorine-containing resin (F1-1), one type may be used alone, or two or more types may be used in combination.

In the resist composition of the present invention, as the fluorine-containing resin (F1-1) used in a positive resist composition, a resin that includes a combination of structural units such as that shown below (namely, a fluorine-containing resin (F1-1-10)) is particularly desirable.

[Chemical Formula 73]

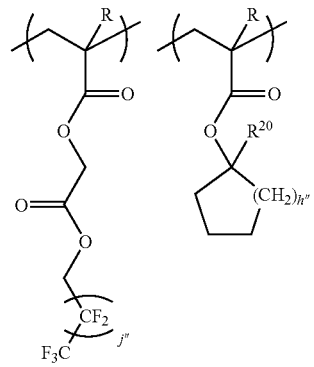

Fluorine-containing resin (F1-1-10)

wherein each R independently represents a hydrogen atom, a lower alkyl group of 1 to 5 carbon atoms or a halogenated lower alkyl group of 1 to 5 carbon atoms; and the plurality of R may be either the same or different from each other. R is as defined for R in the general formula (f1-1-10) above or as defined for R in the general formula (a1-1) above. j" represents an integer of 1 to 3 and is preferably 1 or 2, and is most preferably 1. $R^{20}$ represents a lower alkyl group of 1 to 5 carbon atoms and is the same as the lower alkyl group for R, and is preferably a methyl group or an ethyl group, and most preferably an ethyl group. h" represents an integer of 1 to 6 and is preferably 3 or 4, and is most preferably 4.

The weight average molecular weight (Mw) (the polystyrene equivalent value determined by gel permeation chromatography) of the component (F) is not particularly limited, but is preferably 2,000 to 50,000, more preferably 3,000 to 30,000, and most preferably 4,000 to 25,000. By ensuring that the weight average molecular weight is no more than the upper limit of the above-mentioned range, the component (F) exhibits satisfactory solubility in a resist solvent when used as a resist. On the other hand, by ensuring that the weight average molecular weight is at least as large as the lower limit of the above-mentioned range, the dry etching resistance and cross-sectional shape of the resist pattern become satisfactory.

Further, the dispersity (Mw/Mn) of the component (F) is preferably 1.0 to 5.0, more preferably 1.0 to 3.0, and most preferably 1.2 to 2.5. Here, Mn is the number average molecular weight.

The component (F) can be produced, for example, by a conventional radical polymerization or the like of the monomers corresponding with each of the structural units that constitute the component (F), using a radical polymerization initiator such as azobisisobutyronitrile (AIBN) or dimethyl azobisisobutyrate (V-601).

The amount of the component (F) within the resist composition according to the present invention is preferably from 0.5 to 30 parts by weight, more preferably from 1 to 20 parts by weight, and most preferably from 1 to 10 parts by weight, relative to 100 parts by weight of the component (A). By ensuring that the amount of the component (F) is at least as large as the lower limit of the above-mentioned range, the hydrophobicity of a resist film formed using the resist composition of the present invention is enhanced, which is also suitable for immersion exposure. On the other hand, by ensuring that the amount of the component (F) is no more than the upper limit of the above-mentioned range, solubility of the component (F) in a resist solvent (organic solvent) is improved. Further, the lithography properties are also improved.

<Optional Components>

The resist composition of the present invention may further include a nitrogen-containing organic compound (D) (hereafter referred to as "component (D)") as an optional component.

There are no particular limitations on the component (D) as long as it acts as an acid diffusion control agent, that is, a quencher that entraps the acid generated from the component (B) upon exposure, and because a multitude of these components (D) have already been proposed, any of these known compounds may be used. Examples thereof include amines such as an aliphatic amine and an aromatic amine, and an aliphatic amine, and particularly a secondary aliphatic amine or tertiary aliphatic amine is preferable. Here, an "aliphatic amine" refers to an amine having one or more aliphatic groups, and the aliphatic groups preferably have 1 to 20 carbon atoms.

Examples of these aliphatic amines include amines in which at least one hydrogen atom of ammonia ($NH_3$) has been substituted with an alkyl group or hydroxyalkyl group of 1 to 20 carbon atoms (i.e., alkylamines or alkyl alcohol amines), and cyclic amines.

Specific examples of the alkylamines and alkyl alcohol amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, tri-n-octanolamine, stearyl diethanolamine and lauryl diethanolamine. Among these, trialkylamines and/or alkyl alcohol amines are preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of aromatic amines include aniline, pyridine, 4-dimethylaminopyridine, pyrrole, indole, pyrazole, imidazole and derivatives thereof, diphenylamine, triphenylamine and tribenzylamine.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, and tris[2-{2-(2-hydroxyethoxy)ethoxy}ethyl]amine.

Either one type of amine may be used, or two or more types may be used in combination.

The component (D) is typically used in an amount within a range from 0.01 to 5.0 parts by weight, relative to 100 parts by weight of the component (A). By making the amount of the component (D) within the above-mentioned range, the resist pattern shape, the post exposure stability of the latent image formed by the pattern-wise exposure of the resist layer, and the like can be improved.

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as "component (E)") selected from the group consisting of organic carboxylic acids, and phosphorus oxo acids and derivatives thereof may be added.

Examples of suitable organic carboxylic acids include acetic acid, malonic acid, citric acid, malic acid, succinic acid, benzoic acid, and salicylic acid.

Examples of phosphorus oxo acids and derivatives thereof include phosphoric acid, phosphonic acid and phosphinic acid, and among these, phosphonic acid is particularly desirable.

Examples of phosphorus oxo acid derivatives include esters in which a hydrogen atom within an above-mentioned oxo acid is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

<Organic Solvent>

The resist composition of the present invention can be prepared by dissolving the materials for the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone and 2-heptanone; polyhydric alcohols such as ethylene glycol, diethylene glycol, propylene glycol and dipropylene glycol; polyhydric alcohol derivatives including compounds having an ester bond, such as ethylene glycol monoacetate, diethylene glycol monoacetate, propylene glycol monoacetate and dipropylene glycol monoacetate, and compounds having an ether bond, such as a monoalkyl ether (such as a monomethyl ether, monoethyl ether, monopropyl ether or monobutyl ether) or a monophenyl ether of any of the above polyhydric alcohols or compounds having an ester bond [among these derivatives, propylene glycol monomethyl ether acetate (PGMEA) and propylene glycol monomethyl ether (PGME) are preferred]; cyclic ethers such as dioxane; esters such as methyl lactate, ethyl lactate (EL), methyl acetate, ethyl acetate, butyl acetate, methyl pyruvate, ethyl pyruvate, methyl methoxypropionate and ethyl ethoxypropionate; aromatic organic solvents such as anisole, ethyl benzyl ether, cresyl methyl ether, diphenyl ether, dibenzyl ether, phenetole, butyl phenyl ether, ethylbenzene, diethylbenzene, pentylbenzene, isopropylbenzene, toluene, xylene, cymene and mesitylene; and dimethyl sulfoxide (DMSO).

These organic solvents can be used individually, or in combination as a mixed solvent.

Among these, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA or PGME with a polar solvent is preferable. The mixing ratio (weight ratio) of the mixed solvent can be appropriately determined, taking into consideration the compatibility of the PGMEA or PGME with the polar solvent, but is preferably in a range from 1:9 to 9:1, and more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Further, a mixed solvent of PGME with dimethyl sulfoxide is also preferable. In this case, the mixing ratio (former:latter) of such a mixed solvent is preferably from 9:1 to 1:9, more preferably from 8:2 to 2:8, and most preferably from 7:3 to 5:5.

The amount of the component (S) is not particularly limited, and is adjusted appropriately to a concentration that enables application of a coating solution to a substrate in accordance with the thickness of the coating film. In general, the component (S) is used in an amount that yields a solid content for the resist composition that is within a range from 2 to 20% by weight, and preferably from 3 to 15% by weight.

Dissolving of the materials for a resist composition in the component (S) can be conducted, for example, by simply mixing and stirring each of the above components together using conventional methods, and where required, the composition may also be mixed and dispersed using a dispersion device such as a dissolver, a homogenizer, or a triple roll mill. Furthermore, following mixing, the composition may also be filtered using a mesh, or a membrane filter or the like.

The resist composition of the present invention is a novel composition which was conventionally unknown.

Further, according to the resist composition of the present invention, because the solubility of the component (B1) in an alkali developing solution is high following exposure, the risk of reprecipitation of the component (B1) is low, and a resist pattern with minimal defects can be formed.

It is thought that the reasons this effect is achieved are as follows. The substituent (base dissociable group) included in the cation moiety of the component (B1) and represented by the aforementioned general formula (I) is decomposed by an alkali developing solution such as tetramethylammonium hydroxide (TMAH) used in the developing step following exposure of a resist film. As a result, a carboxyl group is produced, thereby enhancing the alkali solubility of the cation moiety, as compared to the cation moiety of a conventional acid generator, and also making the resist components that should be removed in the developing step to dissolve in an alkali developing solution more efficiently and to be removed completely. Accordingly, the levels of defects that occur following exposure caused by the reprecipitation of resist components, undissolved residues, and the reattachment of alkali-insoluble materials can be reduced.

Furthermore, although compounds having high solubility in a developing solution generally exhibit relatively high solubility in water as well, the compound according to the present invention hardly dissolves in water because it exhibits low solubility in water prior to the decomposition by the developing solution.

From these characteristics described above, the compound according to the present invention is also useful as an acid generator to be used in a resist composition for immersion exposure. It is even more effective when $R^{53}$ or $R^{54}$ in the cation moiety of the component (B1) represented by the aforementioned general formula (I) is a substituent typified by a fluorinated alkyl group for the following reasons; that is, water repellency is particularly enhanced, and moreover, because a fluorinated alkyl group having a low surface free energy is introduced to the cation moiety of the component (B1), when a resist film is formed using the resist composition of the present invention, uneven distribution of the component (B1) near the resist film surface is expected (in other words, the component (B1) including a fluorinated alkyl group that exhibits high water repellency is unevenly distributed in the surface of a resist film).

As described later in detail, immersion exposure is a method in which exposure (immersion exposure) is conducted in a state where the region between the lens and the resist layer formed on a wafer (which is conventionally filled with air or an inert gas such as nitrogen) is filled with a solvent (an immersion medium) that has a larger refractive index than the refractive index of air. In immersion exposure, when the resist film comes into contact with the immersion medium, elution of substances within the resist film (component (B), component (D), and the like) into the immersion medium (namely, substance elution) occurs. This elution of a substance causes phenomenon such as degeneration of the resist film and change in the refractive index of the immersion medium, thereby adversely affecting the lithography properties. The amount of the eluted substance is affected by the properties of the resist film surface (e.g., hydrophilicity, hydrophobicity, and the like). For example, by enhancing the hydrophobicity of the resist film surface, it is presumed that the degree of substance elution can be reduced. Alternatively, lowering of the solubility of substances in water may also be a possible option.

Because it enables suppression of substance elution, using the resist composition of the present invention also enables suppression of degeneration of the resist film and variation in the refractive index of the immersion solvent during immersion exposure. Further, as variation in the refractive index of the immersion medium can be suppressed, a resist pattern having an excellent shape can be formed. Furthermore, the level of contamination of the lens within the exposure apparatus can be lowered. Therefore, there is no need for protection against these disadvantages, and hence, the present invention can contribute to simplifying the process and the exposure apparatus.

<<Method of Forming a Resist Pattern>>

The method of forming a resist pattern according to the second aspect of the present invention includes: forming a resist film on a substrate using the resist composition according to the first aspect of the present invention, subjecting the resist film to exposure, and subjecting the resist film to alkali developing to form a resist pattern.

A preferred example of the method of forming a resist pattern according to the present invention is described below, where a resist film is exposed by the immersion exposure. However, the present invention is not limited to the above example, and the exposure of the resist film may be performed through a general exposure (dry exposure) which is conducted in air or an inert gas such as nitrogen.

Firstly, a resist composition of the present invention is applied onto a substrate using a spinner or the like, and a prebake (post applied bake (PAB)) is conducted to form a resist film.

The substrate is not specifically limited and a conventionally known substrate can be used. For example, substrates for electronic components, and such substrates having wiring patterns formed thereon can be used. Specific examples of the material of the substrate include a silicon wafer; metals such as copper, chromium, iron and aluminum; and glass. Suitable materials for the wiring pattern include copper, aluminum, nickel, and gold. Further, as the substrate, any one of the above-exemplified substrates provided with an inorganic and/or organic film on the surface thereof may also be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is a method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed. The multilayer resist method can be broadly classified into a method in which a double-layer structure consisting of an upper-layer resist film and a lower-layer organic film is formed (a double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film is formed (a three-layer resist method).

After formation of a resist film, an organic antireflection film may be provided on the resist film, thereby forming a triple layer laminate consisting of the substrate, the resist film and the antireflection film. The antireflection film provided on top of the resist film is preferably soluble in an alkali developing solution.

The steps up until this point can be conducted by using conventional techniques. The operating conditions and the like are preferably selected appropriately in accordance with the formulation and the characteristics of the resist composition being used.

Subsequently, the obtained resist film is subjected to selective immersion exposure (liquid immersion lithography) through a desired mask pattern. At this time, the region between the resist film and the lens at the lowermost point of the exposure apparatus is pre-filled with a solvent (immersion medium) that has a larger refractive index than the refractive index of air, and the exposure (immersion exposure) is conducted in this state.

There are no particular limitations on the wavelength used for the exposure, and an ArF excimer laser, KrF excimer laser or $F_2$ laser, or the like can be used. The resist composition according to the present invention is effective for KrF and ArF excimer lasers, and is particularly effective for an ArF excimer laser.

The immersion medium preferably exhibits a refractive index larger than the refractive index of air but smaller than the refractive index of the resist film formed from the resist composition of the present invention. The refractive index of the immersion medium is not particularly limited as long at it satisfies the above-mentioned requirements.

Examples of this immersion medium that exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which preferably have a boiling point within a range from 70 to 180° C. and more preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable.

Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point: 102° C.), and an example of a suitable perfluoroalkylamine compound is perfluorotributylamine (boiling point: 174° C.).

A resist composition of the present invention is particularly resistant to any adverse effects caused by water, and because the resulting lithography properties such as the sensitivity and shape of the resist pattern profile are excellent, water is preferably used as the immersion medium in the present invention. Furthermore, water is also preferred in terms of cost, safety, environmental friendliness, and versatility.

Subsequently, following completion of the immersion exposure step, post exposure baking (PEB) is conducted. A PEB treatment is typically conducted under temperature conditions of 80 to 150° C. for 40 to 120 seconds, preferably 60 to 90 seconds.

Subsequently, developing is conducted using an alkali developing solution composed of an aqueous alkali solution such as a 0.1 to 10% by weight aqueous solution of tetramethylammonium hydroxide (TMAH).

Thereafter, a water rinse is preferably conducted with pure water. This water rinse can be conducted by dripping or spraying water onto the surface of the substrate while rotating the substrate, and washes away the developing solution and those portions of the resist composition that have been dissolved by the developing solution.

By subsequently drying the resist, a resist pattern is obtained in which the resist film (the coating of the resist composition) has been patterned into a shape faithful to the mask pattern.

<<Compound>>

A compound according to the third aspect of the present invention is a compound represented by the aforementioned general formula (b1-11) (hereafter, referred to as "compound (b1-11)").

The compound (b1-11) is the same as the component (B1) in the resist composition according to the first aspect of the present invention.

The compound (b1-11) is a novel compound that has been unknown until now. Further, the compound (b1-11) is useful as an acid generator of a resist composition.

The compound (b1-11) can be produced by using normal methods.

More specifically, for example, when $R^{7''}$ is an aryl group having one group represented by the aforementioned formula (I), the compound (hereafter, referred to as "compound (b1-11-a)") can be produced as follows.

First, a compound represented by general formula (b1-01) and a compound represented by general formula (b1-02) are added to a solution of an organic acid $H^+B^-$ (wherein $B^-$ represents an anion moiety of an organic acid, such as methanesulfonate ion), and reacted. Then, pure water and an organic solvent (for example, dichloromethane, tetrahydrofuran or the like) are added thereto, and the organic phase is collected, to thereby obtain a compound represented by general formula (b1-03) from the organic phase.

Then, a compound represented by general formula (b1-03) is added to an organic solvent (for example, acetone, dichloromethane, tetrahydrofuran or the like) and cooled, and a compound represented by general formula (b1-04-1) shown below is added thereto, and reacted. The resultant is subjected to liquid separation and washing with water, to thereby obtain a compound represented by general formula (b1-05) shown below from the organic phase.

Subsequently, pure water is added to the compound represented by general formula (b1-05), and hydrolysis is conducted to dissociate (deprotect) $-OR^x$, to thereby obtain a compound represented by general formula (b1-06) shown below. The hydrolysis can be conducted by the addition of an acid (hydrochloric acid, sulfuric acid, p-toluenesulfonic acid, or the like) or a base, followed by heating.

Subsequently, the compound represented by general formula (b1-06) is added to an organic solvent (for example, acetone, dichloromethane, tetrahydrofuran or the like) and cooled, and a compound represented by general formula (b1-07) shown below is added thereto, and reacted. The resultant is subjected to liquid separation and washing with water, to thereby obtain a compound represented by general formula (b1-08) shown below from the organic phase.

Subsequently, the compound represented by general formula (b1-08) shown below is dissolved in a mixed solvent of an organic solvent (for example, dichloromethane, tetrahydrofuran or the like) and water. Then, an alkali metal salt $L^+X^-$ (wherein $L^+$ represents an alkali metal cation such as a lithium ion or potassium ion) having a desired anion $X^-$ is added thereto, and reacted. The resultant is subjected to liquid separation and washing with water, to thereby obtain the compound (b1-11-a) from the organic phase.

Alternatively, as a different production method, the compound represented by general formula (b1-03) is added to an organic solvent (for example, acetone, dichloromethane, tetrahydrofuran or the like) and cooled, and a compound represented by general formula (b1-04-2) shown below is added thereto, and reacted. The resultant is subjected to liquid separation and washing with water, to thereby obtain the compound represented by general formula (b1-08) shown below from the organic phase.

Subsequently, the compound represented by general formula (b1-08) shown below is dissolved in a mixed solvent of an organic solvent (for example, dichloromethane, tetrahydrofuran or the like) and water. Then, an alkali metal salt $L^+X^-$ (wherein $L^+$ represents an alkali metal cation such as a lithium ion or potassium ion) having a desired anion $X^-$ is added thereto, and reacted. The resultant is subjected to liquid separation and washing with water, to thereby obtain the compound (b1-11-a) from the organic phase.

[Chemical Formula 74]

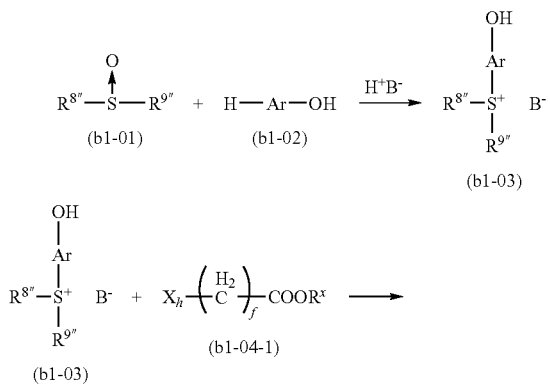

-continued

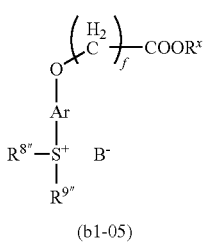
(b1-05)

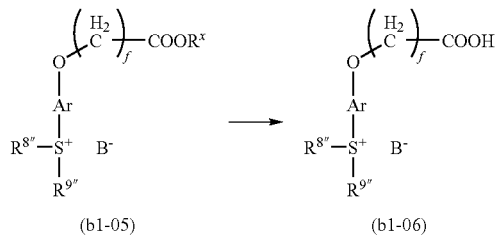
(b1-05) (b1-06)

[Chemical Formula 75]

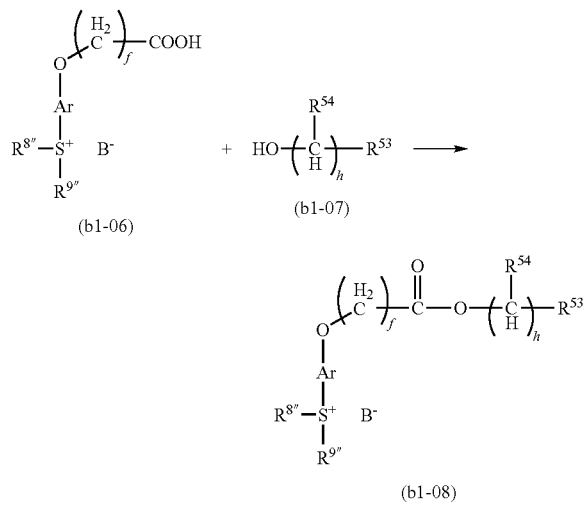
(b1-06) (b1-07)

(b1-08)

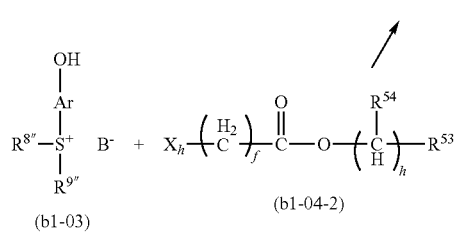
(b1-03) (b1-04-2)

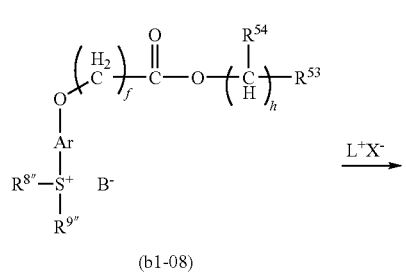
(b1-08)

-continued

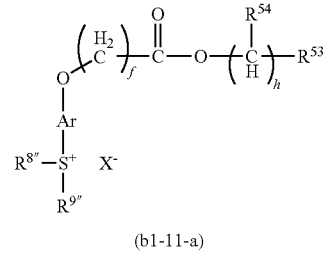
(b1-11-a)

wherein $R^{8''}$, $R^{9'''}$ and X are the same as $R^{8''}$, $R^{9'''}$ and $X^-$ in general formula (b1-11) above; $R^{53}$, $R^{54}$, f and h are the same as $R^{53}$, $R^{54}$, f and h in general formula (I) above; Ar represents an arylene group; $B^-$ represents an anion moiety of an organic acid; $L^+$ represents an alkali metal cation; $X_h$ represents a halogen atom; and $R^x$ represents a protective group.

Examples of the arylene group for Ar include a group in which one hydrogen atom has been removed from the aryl group which may have a substituent exemplified above for $R^{7'''}$ to $R^{9'''}$.

$B^-$ represents an anion moiety of the aforementioned organic acid, and examples thereof include a methanesulfonate ion.

As the halogen atom for $X_h$, a bromine atom or a chlorine atom is preferable.

There are no particular limitations on the protective group for $R^x$ as long as it is an organic group capable of becoming deprotected due to hydrolysis, and when hydrolysis is conducted, for example, under acidic conditions, acid dissociable, dissolution inhibiting groups described above with respect to the structural unit (a1) can be used.

Methods for producing the compound (b1-11-a) are not particularly limited to the method described above. For example, in the production method described above, by using $X_h$—$(CH_2)_f$—COOH [wherein h and f are the same as h and f in the aforementioned general formula (I)] instead of the compound represented by formula (b1-04-1), it is also possible to obtain the compound represented by general formula (b1-06) by directly introducing —$(CH_2)_f$—COOH to the hydroxyl group of the compound represented by general formula (b1-03).

The structure of the obtained compound can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Acid Generator>>

An acid generator according to the fourth aspect of the present invention is an acid generator including the compound according to the third aspect of the present invention.

The acid generator is added to a resist composition for use. The resist composition to which the acid generator is added can be used for both dry exposure and immersion exposure, and is especially suited for immersion exposure.

There are no particular limitations on the resist composition to which the acid generator according to the fourth aspect of the present invention is added, although a chemically amplified resist composition including a base component that exhibits changed solubility in an alkali developing solution under the action of acid, and an acid generator component that generates acid upon exposure is ideal.

EXAMPLES

As follows is a more detailed description of the present invention based on a series of examples, although the scope of the present invention is in no way limited by these examples.

Synthesis Example 1

16.0 g of a compound (1-1) (manufactured by Wako Pure Chemical Industries, Ltd.) and 131.7 g of pure water were added to a three-necked flask, and 5.20 g of hydrochloric acid was then dropwise added thereto. The resultant was then refluxed while heating for 12 hours. The obtained aqueous phase was then washed with 131.7 g of t-butyl methyl ether (TBME), thereby yielding 10.0 g of a compound (1-2).

Then, the compound (1-2) was analyzed by NMR.

$^1$H-NMR (DMSO-d6, 400 MHz): δ (ppm)=2.30 (d, 6H, Ha), 4.53 (s, 2H, Hb), 7.59 (s, 2H, Ar), 7.71-7.89 (m, 10H, Ar).

From the results shown above, it was confirmed that the compound (1-2) had the structure shown below.

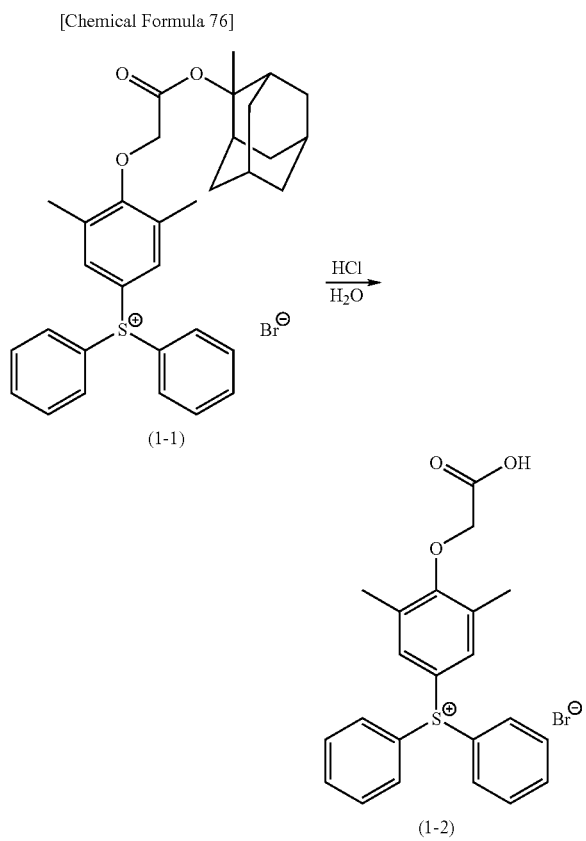

Synthesis Example 2

45.3 g of pure water and 90.5 g of dichloromethane were added to 20 g of the compound (1-2), and 16.8 g of potassium nonafluorobutane sulfonate was further added thereto, followed by stirring at room temperature for 15 hours. Thereafter, the resultant was subjected to liquid separation to collect a dichloromethane phase, and the obtained dichloromethane phase was washed twice with 45.3 g of diluted hydrochloric acid, and was then washed four times with 45.3 g of pure water. The resulting dichloromethane phase was concentrated, dried and solidified, thereby obtaining 26.4 g of a compound (2-1) in the form of a white solid.

Then the compound (2-1) was analyzed by NMR.

$^1$H-NMR (DMSO-d6, 400 MHz): δ (ppm)=2.30 (d, 6H, Ha), 4.39 (s, 2H, Hb), 7.32 (s, 2H, Ar), 7.70-7.87 (m, 10H, Ar).

$^{19}$F-NMR (DMSO-d6, 376 MHz): δ (ppm)=−123.7, −119.3, −112.4, −78.6.

From the results shown above, it was confirmed that the compound (2-1) had the structure shown below.

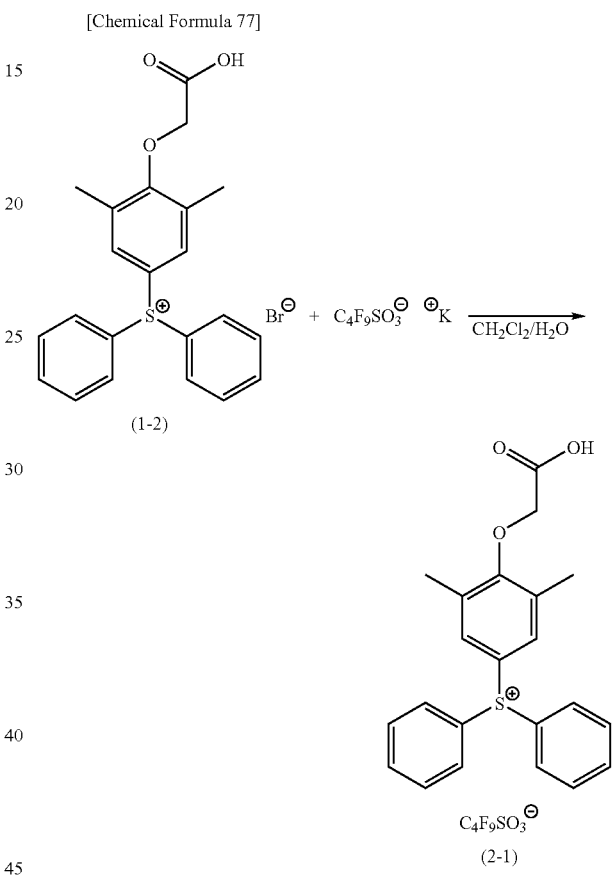

Synthesis Example 3

In a nitrogen atmosphere, 8.54 g of the compound (2-1) and 42.7 g of THF were added to a three-necked flask, and the compound (2-1) was completely dissolved in THF and cooled to 5° C. or lower. 4.81 g of ethyl-N,N-dimethylaminopropyl carbodiimide hydrochloride was added to the resulting solution, followed by stirring at 10° C. or lower for 5 minutes, and 3.77 g of 1H,1H-pentafluoropropanol was then dropwise added thereto. Thereafter, following stirring for 5 minutes, 0.31 g of N,N-dimethylaminopyridine was added thereto, followed by elevating the temperature to room temperature, and a reaction was then effected at room temperature for 30 hours. After completion of the reaction, the organic phase separated by filtration was concentrated, and 42.7 g of dichloromethane was then added thereto to completely dissolve the concentrated organic phase. The obtained dichloromethane phase was washed with diluted hydrochloric acid, and was then further washed with pure water repeatedly until it became neutral. Thereafter, dichloromethane was removed by distillation under reduced pressure, and the obtained oily substance was dried, thereby yielding 9.80 g of a compound (3-1).

Then, the compound (3-1) was analyzed by NMR.

$^1$H-NMR (DMSO-d6, 400 MHz): δ (ppm)=7.75-7.87 (m, 10H, ArH), 7.63 (s, 2H, ArH), 4.94 (t, 2H, OCH$_2$CF$_2$), 4.84 (s, 2H, OCH$_2$), 2.37 (s, 6H, CH$_3$).

$^{19}$F-NMR (DMSO-d6, 376 MHz): δ (ppm)=−77.8, −80.4, −111.9, −118.5, −119.7, −123.

From the results shown above, it was confirmed that the compound (3-1) had the structure shown below.

[Chemical Formula 78]

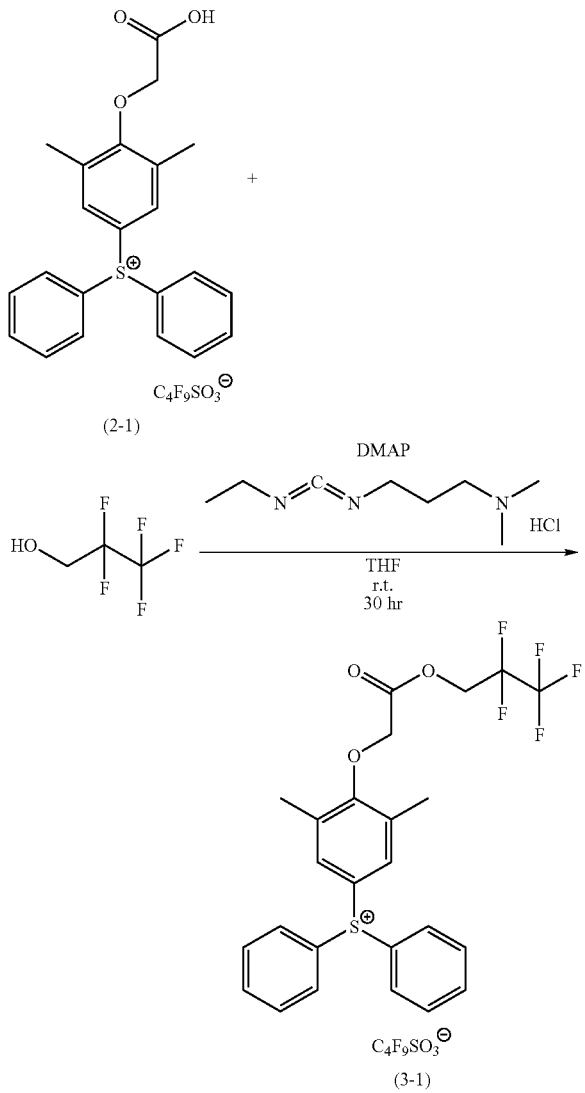

(2-1)

(3-1)

Synthesis Example 4

To 60.75 g of methanesulfonic acid controlled to 20° C. or lower was added 8.53 g of phosphorus oxide, 8.81 g of 2,6-dimethylphenol and 12.2 g of diphenylsulfoxide in small amounts. The resultant was matured for 30 minutes while maintaining the temperature at 15 to 20° C., followed by elevating the temperature to 40° C. and maturing for 2 hours. Then, the reaction liquid was dropwise added to 109.35 g of pure water cooled to 15° C. or lower. Thereafter, 54.68 g of dichloromethane was added and stirred, and the dichloromethane phase was collected. 386.86 g of hexane at a temperature of to 25° C. was charged into a separate vessel, and the dichloromethane phase was dropwise added thereto.

Then, the resultant was matured at 20 to 25° C. for 30 minutes, followed by filtration, thereby obtaining a compound (4-1) (yield: 70.9%).

[Chemical Formula 79]

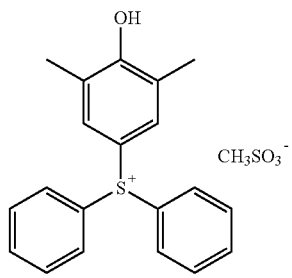

(4-1)

Synthesis Example 5

In a nitrogen atmosphere, 4.03 g of the compound (4-1) and 80.4 g of dichloromethane were added to a three-necked flask, and the compound (4-1) was completely dissolved in dichloromethane. 6.91 g of potassium carbonate was added to the resulting solution, followed by stirring for 10 minutes. A solution formed by dissolving 1.84 g of methyl bromoacetate in 5.5 g of dichloromethane was then dropwise added thereto, and a reaction was then effected under reflux for 19 hours. Following completion of the reaction, potassium carbonate was removed by filtration, and the obtained organic phase was washed with water, followed by the removal of dichloromethane therefrom by distillation under reduced pressure. The obtained crude product was redissolved in 30 g of pure water, and the resulting solution was washed with 30.3 g of t-butyl methyl ether. Thereafter, 2.71 g of potassium nonafluorobutane sulfonate and 34 g of dichloromethane were added thereto, followed by stirring at room temperature for 1 hour. After completion of the reaction, the resulting reaction solution was washed with diluted hydrochloric acid and then with water. Dichloromethane was then removed by distillation under reduced pressure, and the obtained oily substance was dried, thereby yielding 3.08 g of a compound (5-1).

Then, the compound (5-1) was analyzed by NMR.

$^1$H-NMR (DMSO-d6, 400 MHz): δ (ppm)=7.72-7.84 (m, 10H, ArH), 7.59 (s, 2H, ArH), 4.64 (s, 2H, CH$_2$), 3.70 (s, OCH$_3$), 2.29 (s, 6H, CH$_3$).

$^{19}$F-NMR (DMSO-d6, 376 MHz): δ (ppm)=−77.3, −111.5, −118.1, −122.4.

From the results shown above, it was confirmed that the compound (5-1) had a structure shown below.

[Chemical Formula 80]

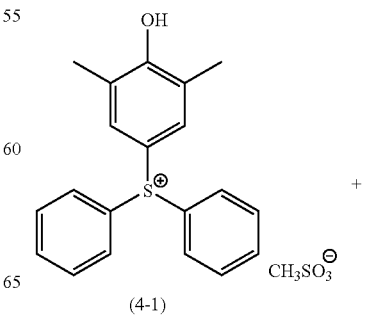

(4-1)

-continued

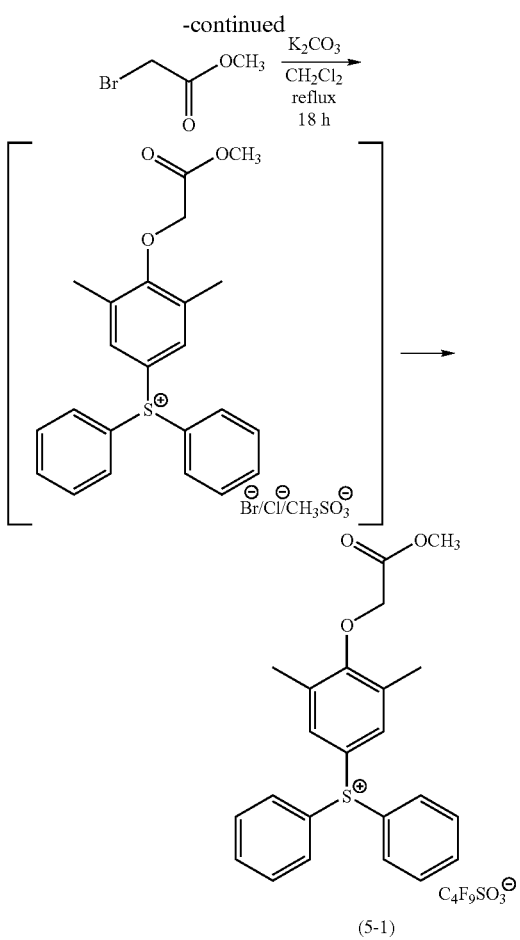

(5-1)

Examples 1 and 2, Comparative Examples 1 and 2

The components shown below in Table 1 were mixed together and dissolved to prepare a series of resist composition solutions for evaluation.

The meanings of the abbreviations used in Table 1 are as shown below. The numerical values within the brackets [ ] represent blend quantities (parts by weight).

TABLE 1

|  | Component (A) | Component (B) | Component (S) |
|---|---|---|---|
| Example 1 | (A)-1 [100] | (B)-1 [7.1] | (S)-1 [2,400] |
| Example 2 | (A)-1 [100] | (B)-2 [6.0] | (S)-1 [2,400] |
| Comparative Example 1 | (A)-1 [100] | (B)-3 [5.9] | (S)-1 [2,400] |
| Comparative Example 2 | (A)-1 [100] | (B)-4 [5.0] | (S)-1 [2,400] |

(A)-1: a polymeric compound represented by chemical formula (A1-1) shown below (manufactured by Promerus LLC). In the polymeric compound (A1-1), the ratio between the structural units (a1:a2, molar ratio), the weight average molecular weight (Mw) and the dispersity (Mw/Mn) are as shown below.

(B)-1: the aforementioned compound (3-1)

(B)-2: the aforementioned compound (5-1)
(B)-3: the aforementioned compound (2-1)
(B)-4: triphenylsulfonium nonafluoro-n-butane sulfonate.
(S)-1: a mixed solvent of PGMEA/PGME=6/4 (weight ratio)

[Chemical Formula 81]

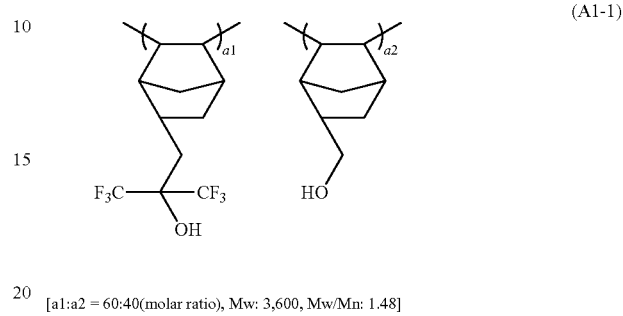

[a1:a2 = 60:40(molar ratio), Mw: 3,600, Mw/Mn: 1.48]

<Evaluation of Defects>

Each resist composition solution for evaluation shown in Table 1 was applied onto an 8-inch silicon wafer using a spinner, and was then prebaked (PAB) on a hotplate at 100° C. for 60 seconds and dried, thereby forming a resist film having a film thickness of 120 nm.

Thereafter, a 2.38% by weight aqueous solution of tetramethylammonium hydroxide (TMAH) was dropwise added from an LD-nozzle to this resist film, and a developing treatment was conducted at 23° C. for 60 seconds. Then, the resist film was washed for 30 seconds with pure water, followed by drying by shaking. Then, the resist film was further heated and dried at 100° C. for 60 seconds.

Subsequently, the resist film surface was observed and the number of defects thereon was measured using a wafer surface inspection apparatus (SP2) manufactured by KLA-TENCOR Corporation. Further, the occurrence of defects at the central portion of a wafer, like the shape of a doughnut, was verified. The results are shown in Table 2.

Defects, that is, forming the shape like a doughnut on a wafer, tend to occur more easily when an acid generator that is highly likely to reprecipitate is used (In a rinsing step following the above-mentioned developing step, the water discharged from a nozzle is poured onto the central portion of a wafer. Accordingly, the concentration of the developing solution at the central portion becomes extremely low very rapidly, and hence, the use of an acid generator with low solubility in the developing solution would highly likely lead to reprecipitation of the acid generator. As a result, because the number of defects at the central portion of the wafer increases, the wafer looks like a doughnut when observed).

TABLE 2

|  | Number of defects | Doughnut-like defects | Amount of elution ($10^{-12}$ mol/cm$^2 \cdot$ sec) | |
|---|---|---|---|---|
|  |  |  | Cation | Anion |
| Example 1 | 217 | Absent | 0.09 | 3.28 |
| Example 2 | 856 | Absent | 0.62 | 3.57 |
| Comparative Example 1 | 2,192 | Absent | 0.89 | 16.23 |

TABLE 2-continued

|  | Number of defects | Doughnut-like defects | Amount of elution ($10^{-12}$ mol/cm$^2$·sec) | |
| --- | --- | --- | --- | --- |
|  |  |  | Cation | Anion |
| Comparative Example 2 | 67,325 | Present | 4.32 | 5.97 |

<Evaluation of Elution>

Each resist composition solution for evaluation shown in Table 1 was applied onto an 8-inch silicon wafer using a spinner, and was then prebaked (PAB) on a hotplate at 90° C. for 60 seconds and dried, thereby forming a resist film having a film thickness of 120 nm.

Then, with respect to the resist film, using VRC310S (product name; manufactured by S.E.S Co., Ltd.), one droplet of pure water (150 μl) was moved from the center of the wafer in a circular manner at room temperature at a constant linear velocity (total area of the resist film that came in contact with the droplet: 221.56 cm$^2$).

Thereafter, the droplet of pure water was collected, and the amount of cations and anions ($10^{-12}$ mol/cm$^2$·sec) of the component (B) eluted to the pure water droplet was measured using an analyzing apparatus Agilent-HP1100 LC-MSD (product name; manufactured by Agilent Technologies). The results are shown in Table 2.

Examples 3 and 4, Comparative Examples 3 and 4

The components shown in the following Table 3 were mixed together and dissolved to obtain negative resist composition solutions.

TABLE 3

|  | Component (A) | Component (B) | Component (C) | Component (D) | Component (S) |
| --- | --- | --- | --- | --- | --- |
| Example 3 | (A)-1 | (B)-1 | (C)-1 | (D)-1 | (S)-1 |
|  | [100] | [6.2] | [5.5] | [0.6] | [2,100] |
| Example 4 | (A)-1 | (B)-2 | (C)-1 | (D)-1 | (S)-1 |
|  | [100] | [5.3] | [5.5] | [0.6] | [2,100] |
| Comparative Example 3 | (A)-1 | (B)-3 | (C)-1 | (D)-1 | (S)-1 |
|  | [100] | [10.4] | [5.5] | [0.6] | [2,100] |
| Comparative Example 4 | (A)-1 | (B)-4 | (C)-1 | (D)-1 | (S)-1 |
|  | [100] | [4.4] | [5.5] | [0.6] | [2,100] |

In Table 3, the meanings of the abbreviations used for the components (A), (B) and (S) are the same as those used in Table 1, and the meanings of the abbreviations used for the components (C) and (D) are as shown below. Further, the values in brackets [ ] indicate the amount (in terms of parts by weight) of the component added.

(C)-1: tetraethoxymethylated glycoluril.
(D)-1: triisopropanolamine.

<Evaluation of Lithography Properties>

Using the negative resist compositions of Examples 3 and 4 and Comparative Examples 3 and 4 obtained as described above, resist patterns were formed by the following method of forming resist patterns.

[Method of Forming a Negative Resist Pattern]

An organic antireflection film composition (product name: AR-46, manufactured by Rohm and Haas Company) was applied uniformly onto a silicon wafer using a spinner, and the composition was then baked and dried on a hotplate at 215° C. for 60 seconds, thereby forming an organic antireflection film having a film thickness of 31 nm.

Then, the negative resist composition obtained from each example was uniformly applied onto the organic antireflection film using a spinner, and was then prebaked (PAB) on a hotplate at 90° C. for 60 seconds, thereby forming a resist film having a film thickness of 160 nm.

Subsequently, the resist film was subjected to selective exposure with an ArF excimer laser (193 nm) through a mask pattern (6% half tone), using an ArF exposure apparatus NSR-S302A (product name; manufactured by Nikon Corporation, NA (numerical aperture)=0.60, ⅔ annular illumination).

Thereafter, a post exposure bake (PEB) treatment was conducted at 110° C. for 60 seconds, followed by alkali development for 60 seconds at 23° C. in a 2.38% by weight aqueous tetramethylammonium hydroxide (TMAH) solution (product name: NMD-3; manufactured by Tokyo Ohka Kogyo Co., Ltd.). Then, the resist was washed for 30 seconds with pure water, followed by drying by shaking. Then, the resist film was further heated and dried at 100° C. for 60 seconds.

As a result, in Examples 3 and 4 and Comparative Examples 3 and 4, a line and space pattern (L/S pattern) in which lines having a line width of 120 nm were spaced at equal intervals (pitch: 240 nm) was formed. Furthermore, in these examples, no foreign matter was observed on the L/S patterns.

In Examples 3 and 4 and Comparative Examples 3 and 4, the optimum exposure dose Eop (mJ/cm$^2$; sensitivity) with which an L/S pattern having a line width of 120 nm and a pitch of 240 nm was formed was determined. The results are shown in Table 4.

Further, the cross-sectional shape of the L/S patterns formed at the above Eop value and having a line width of 120 nm and a pitch of 240 nm was observed using a measuring SEM (product name: S-9220, manufactured by Hitachi, Ltd.), and the rectangularity of the patterns was evaluated based on the following criteria. The results are shown in Table 4.

(Criteria)

A: No footing of the resist pattern was observed.

B: Footing of the resist pattern was observed, and rectangularity of the resist pattern was also low.

TABLE 4

|  | Eop (mJ/cm$^2$) | Cross-sectional shape |
| --- | --- | --- |
| Example 3 | 33.0 | A |
| Example 4 | 34.0 | A |
| Comparative Example 3 | 38.0 | B |
| Comparative Example 4 | 24.0 | A |

From the results shown above, it was confirmed that the compound according to the present invention is useful as an acid generator to be used in a resist composition. Further, it was confirmed that because of excellent solubility of the compound in an alkali developing solution, the level of defects could be reduced, and the level of elution of the compound in pure water was also low.

Therefore, the compound exhibited high solubility in an alkali developing solution as well as low solubility in water, and hence, the compound is suited also as an acid generator used in a resist composition for immersion exposure.

In general, when the resist composition is a negative resist composition, because unexposed portions (namely, the portions in which an acid generator does not react) need to dissolve, there is a high risk of reprecipitation of the acid generator. On the other hand, when the resist composition is a positive resist composition, although exposed portions need to dissolve, because an acid generator generates an acid upon exposure and is decomposed, the risk of reprecipitation of the acid generator is low.

[Preparation of Positive Resist Composition Solution]

The components shown in Table 5 below were mixed together to obtain positive resist composition solutions.

TABLE 5

|  | Component (A) | Component (B) |  | Component (D) | Component (F) | Component (S) |
|---|---|---|---|---|---|---|
| Example 5 | (A)-2 | (B)-5 | (B)-1 | (D)-1 | (F)-1 | (S)-1 |
|  | [100] | [10] | [2.7] | [0.35] | [2.1] | [2,400] |
| Example 6 | (A)-2 | (B)-6 | (B)-1 | (D)-1 | (F)-1 | (S)-1 |
|  | [100] | [10] | [2.7] | [0.35] | [2.1] | [2,400] |
| Example 7 | (A)-2 | (B)-5 | (B)-1 | (D)-1 | (F)-1 | (S)-1 |
|  | [100] | [4.6] | [6.2] | [0.35] | [2.1] | [2,400] |
| Reference Example 5 | (A)-2 | (B)-5 | — | (D)-1 | (F)-1 | (S)-1 |
|  | [100] | [10] |  | [0.35] | [2.1] | [2,400] |
| Reference Example 6 | (A)-2 | (B)-5 | — | (D)-1 | — | (S)-1 |
|  | [100] | [10] |  | [0.35] |  | [2,400] |

In Table 5, the components (B)-1 and (S)-1 are as defined above. The meanings of the abbreviations used for the other components in Table 5 are as shown below. The numerical values within the brackets [ ] represent blend quantities (parts by weight).

(A)-2: a polymeric compound (copolymer) (A)-2 synthesized in the following Reference Example (A)-2.

(B)-5: an acid generator (B)-5 represented by formula shown below.

(B)-6: an acid generator (B)-6 represented by formula shown below.

(D)-1: tri-n-pentylamine.

(F)-1: a polymeric compound (F)-1 synthesized in the following Reference Example (F)-1 (l/m=75/25; Molecular weight: 23,900; Dispersity: 1.5).

[Chemical Formula 82]

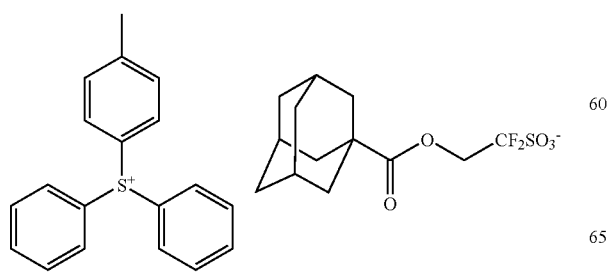

(B)-5

[Chemical Formula 83]

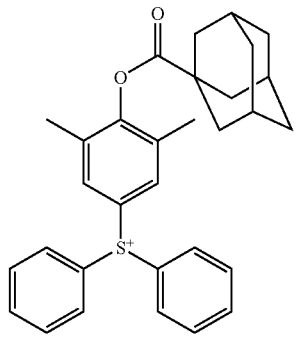

(B)-6

[Chemical Formula 84]

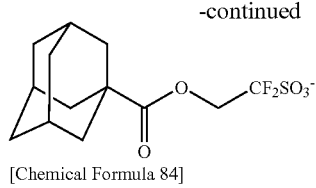

(F)-1

Reference Example (A)-2

Synthesis of Polymeric Compound (A)-2

The polymeric compound (copolymer) (A)-2 was obtained through [Synthesis Example 6] to [Synthesis Example 8] described below.

Synthesis Example 6

Synthesis of 2-(2-(2-methyl-2-adamantyloxy)-2-oxoethoxy)-2-oxo ethanol 37.6 g (494 mmol) of glycolic acid, 700 mL of DMF, 86.5 g (626 mmol) of potassium carbonate, and 28.3 g (170 mmol) of potassium iodide were charged into a 2 L three-necked flask equipped with a thermometer, a cooling pipe, and a stirrer, followed by stirring at room temperature for 30 minutes. Then, 300 mL of a dimethylformamide solution containing 100 g (412 mmol) of 2-methyl-2-adamantyl chloroacetate was gradually added thereto. The resultant was heated to 40° C., and was then stirred for 4 hours. Following completion of the reaction, 2,000 mL of diethyl ether was added to the reaction mixture, followed by filtration of the resulting mixture. The obtained solution was washed three times with 500 mL of distilled water, followed by crystallization using a mixed solution containing 300 mL of toluene and 200 mL of heptane, thereby obtaining 78 g of an objective compound in the form of a colorless solid (yield: 67%, GC purity: 99%).

Synthesis Example 7

Synthesis of 2-(2-(2-methyl-2-adamantyloxy)-2-oxoethoxy)-2-oxoethyl methacrylate (compound 3)

165 g (584 mmol) of 2-(2-(2-methyl-2-adamantyloxy)-2-oxoethoxy)-2-oxoethanol, 2,000 mL of THF, 105 mL (754 mmol) of triethylamine, and 0.165 g (1,000 ppm) of p-methoxyphenol were added to and dissolved in a 2 L three-necked flask equipped with a thermometer, a cooling pipe, and a stirrer. Following completion of the dissolution, 62.7 mL (648 mmol) of methacryloyl chloride was gradually added thereto while cooling in an ice bath. The temperature of the resultant was then elevated to room temperature, and the resultant was stirred for 3 hours. Following the completion of the reaction, 1,000 mL of diethyl ether was added thereto, followed by washing with 200 mL of distilled water 5 times. Thereafter, the extraction liquid was concentrated, thereby obtaining 198 g of an objective substance (namely, a compound 3 having the following structure) in the form of a colorless liquid (yield: 97%, GC purity: 99%).

Synthesis Example 8

9.83 g (57.80 mmol) of a [compound 1] having the following structure, 6.00 g (24.20 mmol) of a [compound 2] having the following structure, 14.11 g (40.32 mmol) of a [compound 3] having the following structure, and 2.22 g (9.41 mmol) of a [compound 4] having the following structure were dissolved in 48.24 g of methyl ethyl ketone. Then, 3.3 mmol of dimethyl azobisisobutyrate (V-601) as a polymerization initiator was added to and dissolved in the resulting solution. The reaction solution was dropwise added to 26.80 g of methyl ethyl ketone heated to 75° C. over 6 hours in a nitrogen atmosphere. Following completion of the dropwise addition, the reaction solution was heated for 1 hour while stirring, and was then cooled to room temperature. The resulting polymer solution was concentrated under reduced pressure, and dropwise added to an excess amount of a mixed solution of methanol/water to thereby precipitate a polymer. Then, the precipitated copolymer was separated by filtration, followed by washing and drying, thereby obtaining 20 g of a copolymer (A)-2 as an objective compound.

This copolymer had a weight average molecular weight, determined by GPC and referenced against standard polystyrenes, of 9,400, and a dispersity of 2.19.

Further, the copolymer (A)-2 was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m/n/o=51.4/28.7/9.4/10.4.

[Chemical Formula 85]

[Compound 1]

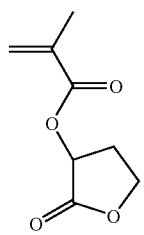

[Compound 2]

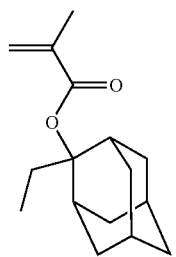

[Compound 3]

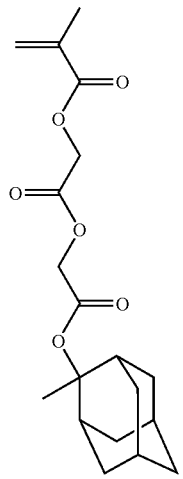

[Compound 4]

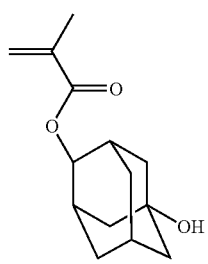

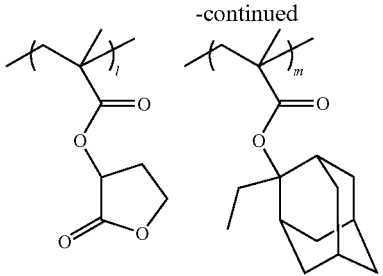

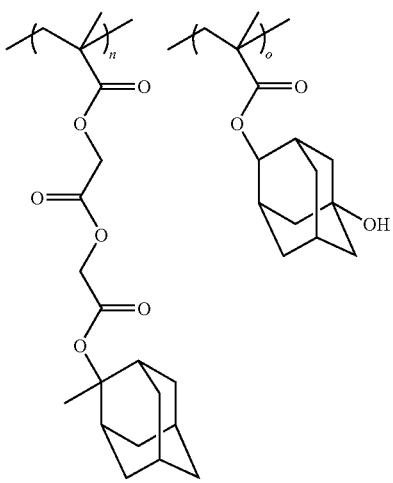

Polymeric compound(copolymer) (A)-2

Reference Example

Synthesis of Compound (F)-1

15.00 g (54.32 mmol) of a [compound 5] having the following structure and 5.21 g (23.28 mmol) of a [compound 6] having the following structure were charged into a three-necked flask equipped with a thermometer and a reflux tube and were dissolved by adding 114.52 g of THF thereto. Then, 4.66 mmol of dimethyl azobisisobutyrate (product name: V-601) as a polymerization initiator was added and dissolved in the resulting solution. The obtained reaction solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 5.6 g of a compound (F)-1 having the following structure as an objective compound.

With respect to the compound (F)-1, the weight average molecular weight (Mw) and the dispersity (Mw/Mn) were determined by the polystyrene equivalent value as measured by gel permeation chromatography (GPC). Further, the compound (F)-1 was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=75/25.

[Chemical Formula 86]

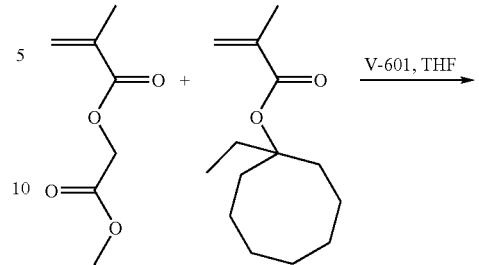

[Compound 5]   [Compound 6]

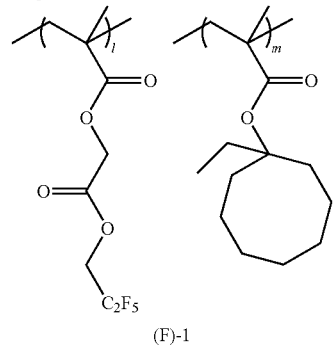

(F)-1

[Formation of a Positive Resist Pattern]

An organic antireflection film composition (product name: ARC29A, manufactured by Brewer Science Ltd.) was applied onto an 12-inch silicon wafer using a spinner, and the composition was then baked and dried on a hotplate at 205° C. for 60 seconds, thereby forming an organic antireflection film having a film thickness of 85 nm. Then, each of the positive resist compositions obtained in Examples 5 and 6 and Reference Example 5 was applied onto the antireflection film using a spinner, and was then prebaked (PAB) on a hotplate at 110° C. for 60 seconds and dried, thereby forming a resist film having a film thickness of 120 nm. Subsequently, the resist film was selectively irradiated with an ArF excimer laser (193 nm) through a mask pattern, using an ArF immersion exposure apparatus NSR-S609B (manufactured by Nikon Corporation, NA (numerical aperture)=1.07, Cross-pole=0.78/0.97). Thereafter, a post exposure bake (PEB) treatment was conducted at 90° C. for 60 seconds, followed by development for 10 seconds at 23° C. in a 2.38% by weight aqueous solution of tetramethylammonium hydroxide (TMAH). As a result, in each of the examples, an L/S pattern with a line width of about 50 nm and a pitch of 110 nm was formed on the resist film. The sensitivity values (optimum exposure dose: Eop (mJ/cm$^2$)) during this step are shown in Table 6.

<Evaluation of a Resist Pattern>

Further, the patterns obtained at the above Eop value were observed using a measuring scanning electron microscope (SEM), and dimensions of space portions therein were measured. The closer to 50 nm the dimensions of space portions, the better the removability following development (solubility in a developing solution). The results are shown in Table 6.

<Evaluation of 5% EL Margin>

Furthermore, with respect to the dimensions of the obtained pattern, the exposure dose with which a pattern could be formed having a dimension of the obtained pattern ±5% (i.e., 47.5 nm to 52.5 nm) was determined, and the EL margin (unit: %) was determined by the following formula. The results are shown in Table 6.

$$EL\ margin(\%)=(|E1-E2|/Eop)\times 100$$

wherein E1 represents the exposure dose (mJ/cm$^2$) for forming a pattern having a dimension of 47.5 nm, and E2 represents the exposure dose (mJ/cm$^2$) for forming a pattern having a dimension of 52.5 nm.

The larger the value of EL margin, the smaller the variation in the pattern size depending on the change in the exposure dose, thereby resulting in favorable improvement in the process margin.

TABLE 6

|  | Sensitivity (mJ/cm$^2$) | 5% EL margin | Dimension of space portion (nm) |
|---|---|---|---|
| Example 5 | 15 | 8.36 | 50.0 |
| Example 6 | 18 | 7.49 | 45.2 |
| Reference Example 5 | 14 | 3.27 | 44.5 |

From the results shown in Table 6, it was confirmed that the resist composition according to the present invention exhibited excellent solubility in a developing solution and also enabled the formation of a resist pattern that is faithful to the target dimension. Further, it was confirmed that the EL margin of the obtained resist pattern was also satisfactory <Evaluation of Resistance to Pattern Collapse (Collapse Margin)>

With respect to the resist patterns obtained in Example 5 and Reference Example 5, the resist pattern of Example 7 obtained (at an Eop of 20 mJ/cm$^2$) in a similar manner to the above-mentioned method of forming a positive resist pattern, and the resist pattern of Reference Example 6 obtained (at an Eop of 18 mJ/cm$^2$) in a similar manner to the above-mentioned method of forming a positive resist pattern except that a top coat for immersion exposure was also formed, the resistance of L/S patterns to collapse was observed by increasing the exposure dose from the Eop values at which the respective patterns were formed. As a result, it was confirmed that the L/S patterns of Examples 5 and 7 exhibited excellent resistance to pattern collapse as compared to that of Reference Example 5, and also had a pattern collapse margin which was equivalent to or even superior to that of Reference Example 6, which was evaluated with support from an additional top coat.

Here, the resist pattern which has the top coat for immersion exposure obtained in a similar manner to the above-mentioned method of forming the positive resist pattern except that an under-mentioned step was appended before subjecting the resist film to exposure.

A coating liquid for forming a top coat (product name: TILC-057, manufactured by Tokyo Ohka Kogyo Co., Ltd.) was applied by using a spinner onto the resist film of a film thickness of 120 nm which was obtained by the PAB treatment and the drying treatment, and the resist film on which the coating liquid was applied was then baked and was dried at 90° C. for 60 seconds, thereby forming a top coat having a film thickness of 35 nm.

Although a substituent (—CH$_2$CF$_2$CF$_3$) was introduced following a salt exchange reaction in the above-mentioned [Synthesis Example 2] and [Synthesis Example 3], the compound according to the present invention can also be obtained by introducing a substituent into the aforementioned compound (1-2), followed by a salt exchange reaction.

Synthesis Example (B1-2) for introducing a substituent and Synthesis Examples (B1-3) to (B1-24) using various anions are described below.

Synthesis Example (B1-2)

Introduction of a Substituent

In a nitrogen atmosphere, 5.00 g of the compound (1-2) and 50.0 g of dichloromethane were added to a three-necked flask, and the compound (1-2) was completely dissolved in dichloromethane and cooled to 5° C. or lower. 0.28 g of N,N-dimethylaminopyridine was added to the resulting solution, followed by stirring at 10° C. or lower for 5 minutes, and 5.46 g of ethyl-N,N-dimethylaminopropyl carbodiimide hydrochloride was then gradually added thereto. After stirring the resultant for 10 minutes, 1.37 g of 1H,1H-pentafluoropropanol was gradually dropwise added thereto. After completion of the dropwise addition, the temperature of the resulting mixture was elevated to room temperature, followed by stirring at room temperature for 30 hours. After completion of the reaction, the dichloromethane phase obtained as a result of liquid separation was washed with diluted hydrochloric acid, and was then further washed with pure water repeatedly until it became neutral. Thereafter, dichloromethane was removed by distillation under reduced pressure, and the obtained viscous solid was dried, thereby yielding 3.72 g of a compound (B1-2).

[Chemical Formula 87]

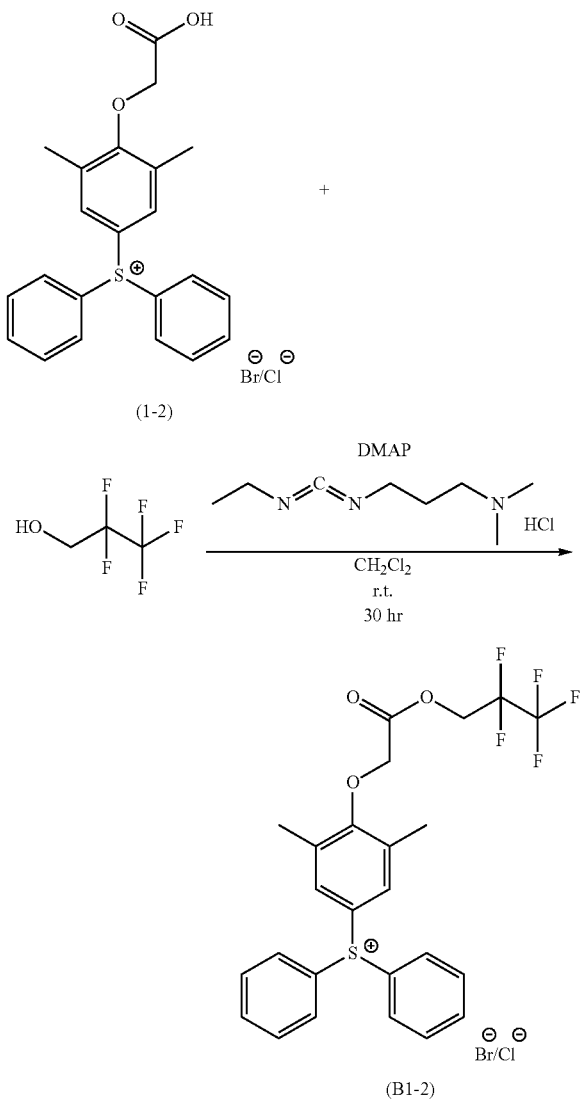

145

Synthesis Example (B1-3)

Salt Exchange Reaction 1.30 g of the compound (B1-2) was completely dissolved in 10.1 g of dichloromethane. Then, 3.82 g of pure water and 1.32 g of a compound D were added thereto, followed by stirring at room temperature for 1 hour. After completion of the reaction, the resulting reaction solution was washed with water, and dichloromethane was then removed therefrom by distillation under reduced pressure, and the obtained white solid was dried, thereby yielding 1.58 g of a compound (B1-3).

[Chemical Formula 88]

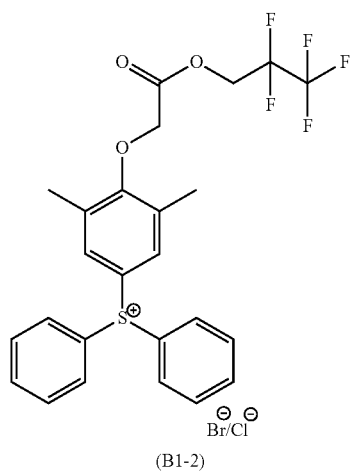

(B1-2)

+

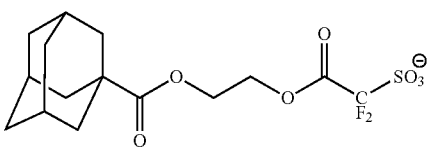

146

-continued

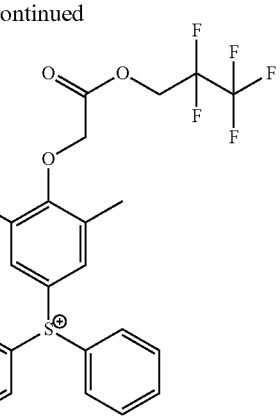

(B1-3)

The above-mentioned compound D is a compound represented by the following chemical formula.

[Chemical Formula 89]

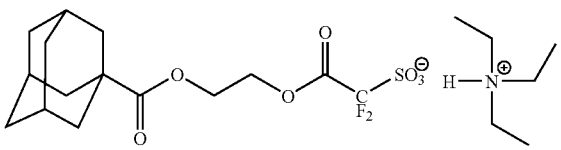

Synthesis Examples (B1-4) to (B1-24)

Compounds (B1-4) to (B1-24) were obtained in a similar manner to that in the above-mentioned Synthesis Example (B1-3). Chemical formulas and NMR data for the compound D used in each synthesis example and for the obtained compounds (B1-4) to (B1-24) are shown in the following Tables 7 to 12.

The amount of each substance used during the salt exchange reaction is the same.

TABLE 7

| Synthesis Example | Reactant (Compound D) $X^-M^+$ |
|---|---|
| B1-3 | 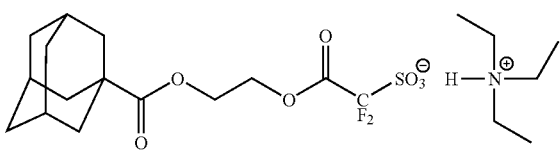 |
| B1-4 | 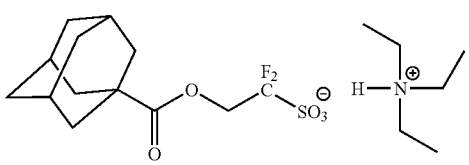 |

TABLE 7-continued
B1-5 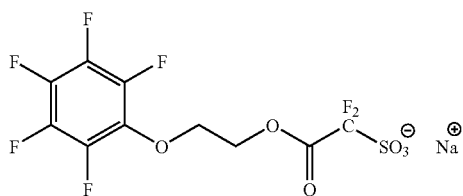
B1-6 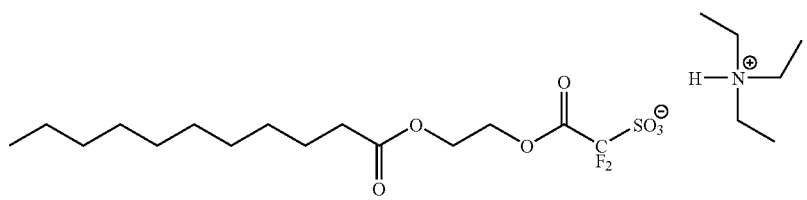
B1-7 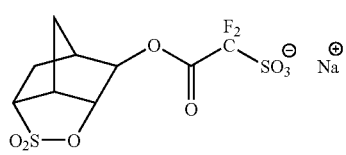
B1-8 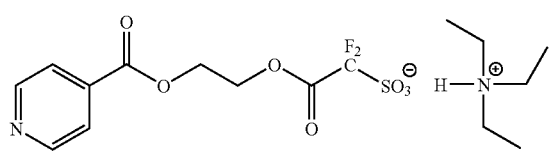
B1-9 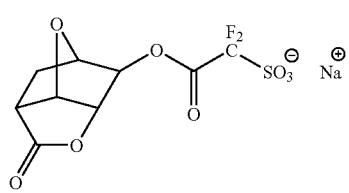
B1-10 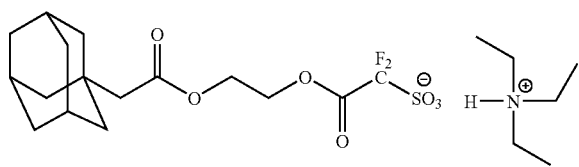
B1-11 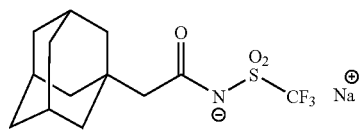
B1-12 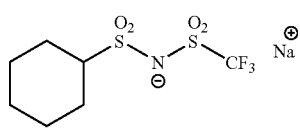 [SMILES: O=S(=O)(NS(=O)(=O)C(F)(F)F)C1CCCCC1 ; [Na+]]
| Synthesis Example | Product Anion | Cation |
|---|---|---|
| B1-3 | 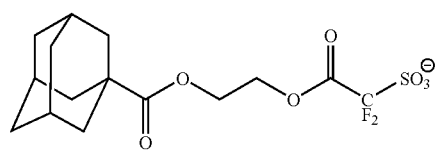 | (b1-11-9) |

TABLE 7-continued
| B1-4 | 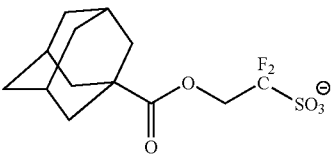 | (b1-11-9) |
| B1-5 | 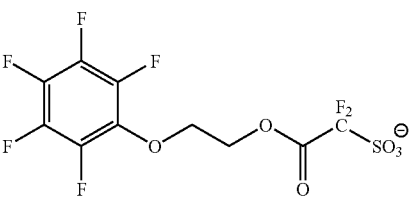 | (b1-11-9) |
| B1-6 | 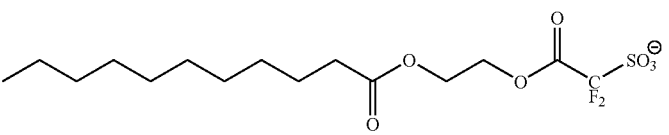 | (b1-11-9) |
| B1-7 | 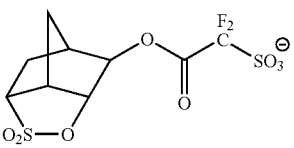 | (b1-11-9) |
| B1-8 | 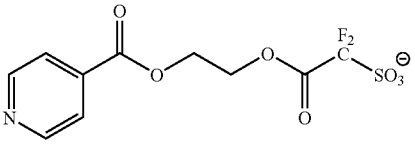 | (b1-11-9) |
| B1-9 | 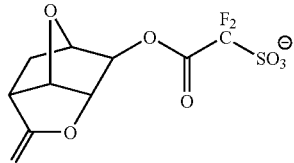 | (b1-11-9) |
| B1-10 | 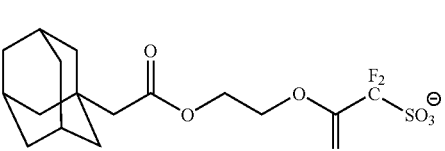 | (b1-11-9) |
| B1-11 | 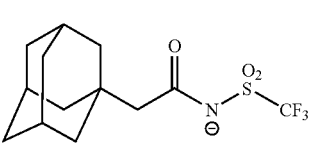 | (b1-11-9) |
| B1-12 | 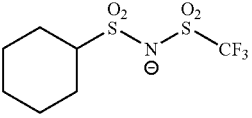 | (b1-11-9) |

TABLE 8

| Synthesis Example | Reactant (Compound D) X⁻M⁺ | Product Anion | Cation |
|---|---|---|---|
| B1-13 | adamantyl-C(O)-N⁻(SO₂CF₃) Na⁺ | adamantyl-C(O)-N⁻(SO₂CF₃) | (b1-11-9) |
| B1-14 | adamantyl-O-CF₂-CF₂-SO₂-N⁻-SO₂-CF₃ Na⁺ | adamantyl-O-CF₂-CF₂-SO₂-N⁻-SO₂-CF₃ | (b1-11-9) |
| B1-15 | naphthyl-CH₂-O-CF₂-CF₂-SO₃⁻ Li⁺ | naphthyl-CH₂-O-CF₂-CF₂-SO₃⁻ | (b1-11-9) |
| B1-16 | adamantyl-O-CF₂-CF₂-SO₃⁻ Li⁺ | adamantyl-O-CF₂-CF₂-SO₃⁻ | (b1-11-9) |
| B1-17 | F₃CO₂S-C⁻(SO₂CF₃)(SO₂CF₃) H⁺ | F₃CO₂S-C⁻(SO₂CF₃)(SO₂CF₃) | (b1-11-9) |
| B1-18 | pentafluorophenyl-C⁻(SO₂CF₃)(SO₂CF₃) ... F₃CO₂S SO₂CF₃ H⁺ | pentafluorophenyl-C⁻(SO₂CF₃)(SO₂CF₃) F₃CO₂S SO₂CF₃ | (b1-11-9) |
| B1-19 | camphor-CH₂-SO₃⁻ Na⁺ | camphor-CH₂-SO₃⁻ | (b1-11-9) |
| B1-20 | CF₃SO₃⁻ K⁺ | CF₃SO₃⁻ | (b1-11-9) |

TABLE 9

| Synthesis Example | Reactant (Compound D) X⁻M⁺ | Product Anion | Cation |
|---|---|---|---|
| B1-21 | C₃F₇SO₃⁻ K⁺ | C₃F₇SO₃⁻ | (b1-11-9) |
| B1-22 | cyclic (O₂S-N⁻-SO₂-CF₂-CF₂-CF₂) K⁺ | cyclic (O₂S-N⁻-SO₂-CF₂-CF₂-CF₂) | (b1-11-9) |

TABLE 9-continued

| Synthesis Example | Reactant (Compound D) X⁻M⁺ | Product Anion | Cation | |
|---|---|---|---|---|
| B1-23 | F$_3$CF$_2$C-S(O$_2$)-N⁻-S(O$_2$)-CF$_3$  K⁺ | F$_3$CF$_2$C-S(O$_2$)-N⁻-S(O$_2$)-CF$_3$ | | (b1-11-9) |
| B1-24 | CH$_2$=CH-CH$_2$-O-CF$_2$-CF$_2$-SO$_3$⁻  Li⁺ | CH$_2$=CH-CH$_2$-O-CF$_2$-CF$_2$-SO$_3$⁻ | | (b1-11-9) |

TABLE 10

| Synthesis Example | $^1$H-NMR (DMSO-d6, 400 MHz): δ (ppm) | $^{19}$F-NMR (DMSO-d6, 376 MHz): δ (ppm) |
|---|---|---|
| B1-1 | 7.75-7.87 (m, 10H, ArH), 7.63 (s, 2H, ArH), 4.94 (t, 2H, OCH2CF2), 4.84 (s, 2H, OCH2), 2.37 (s, 6H, CH3) | −77.8, −80.4, −111.9, −118.5, −119.7, −123 |
| B1-2 | 7.75-7.87 (m, 10H, ArH), 7.63 (s, 2H, ArH), 4.94 (t, 2H, OCH2CF2), 4.84 (s, 2H, OCH2), 2.37 (s, 6H, CH3) | −80.4, −119.7 |
| B1-3 | 7.75-7.87 (m, 10H, ArH), 7.63 (s, 2H, ArH), 4.94 (t, 2H, OCH2CF2), 4.84 (s, 2H, OCH2), 4.40 (t, 2H, CH2), 4.21 (t, 2H, CH2), 2.37 (s, 6H, CH3), 1.61-1.98 (m, 15H, Adamantane) | −80.4, −111.2, −119.7 |
| B1-4 | 7.75-7.87 (m, 10H, ArH), 7.63 (s, 2H, ArH), 4.94 (t, 2H, OCH2CF2), 4.84 (s, 2H, OCH2), 4.45 (t, 2H, CF2CH2), 2.37 (s, 6H, CH3), 1.64-1.95 (m, 15H, Adamantane), | −80.4, −111.2, −119.7 |
| B1-5 | 7.75-7.87 (m, 10H, ArH), 7.63 (s, 2H, ArH), 4.94 (t, 2H, OCH2CF2), 4.84 (s, 2H, OCH2), 4.40-4.50 (m, 4H, CH2), 2.37 (s, 6H, CH3), | −80.4, −106.7, −119.7, −154.0, −160.0, −161.5 |
| B1-6 | 7.75-7.87 (m, 10H, ArH), 7.63 (s, 2H, ArH), 4.94 (t, 2H, OCH2CF2), 4.84 (s, 2H, OCH2), 4.41 (t, 2H, CH2), 4.23 (t, 2H, CH2), 0.79-2.89 (m, 27H, CH3 + Undecanoyl) | −80.4, −106.8, −119.7 |
| B1-7 | 7.75-7.87 (m, 10H, ArH), 7.63 (s, 2H, ArH), 4.94 (t, 2H, OCH2CF2), 4.84 (s, 2H, OCH2), 4.78 (m, 1H, CH), 4.66 (t, 1H, CH), 3.88 (t, 1H, CH), 3.34 (m, 1H, CH), 2.49 (m, 1H, CH), 1.73-2.37 (m, 10H, CH3 + CH2) | −80.4, −107.7, −119.7 |
| B1-8 | 8.74-8.82 (m, 2H, Py-H), 7.75-7.84 (m, 12H, ArH + Py-H), 7.63 (s, 2H, ArH), 4.94 (t, 2H, OCH2CF2), 4.84 (s, 2H, OCH2), 4.54-4.61 (m, 4H, CH2CH2), 2.37 (s, 6H, CH3) | −80.4, −106.5, −119.7 |
| B1-9 | 7.75-7.87 (m, 10H, ArH), 7.63 (s, 2H, ArH), 5.46 (t, 1H, Oxo-norbornane), 4.95 (m, 3H, OCH2CF2 + Oxo-norbornane), 4.84 (s, 2H, OCH2), 4.71 (d, 1H, Oxo-norbornane), 2.69-2.73 (m, 1H, Oxo-norbornane), 2.37 (s, 6H, CH3), 2.06-2.16 (m, 2H, Oxo-norbornane) | −80.4, −107.1, −119.7 |
| B1-10 | 7.75-7.87 (m, 10H, ArH), 7.63 (s, 2H, ArH), 4.94 (t, 2H, OCH2CF2), 4.84 (s, 2H, OCH2), 4.40 (t, 2H, CH2), 4.20 (t, 2H, CH2), 2.37 (s, 6H, CH3), 2.05 (s, 2H, CH2), 1.53-1.95 (m, 15H, Ad) | −80.4, −111.2, −119.7 |

TABLE 11

| Synthesis Example | $^1$H-NMR (DMSO-d6, 400 MHz): δ (ppm) | $^{19}$F-NMR (DMSO-d6, 376 MHz): δ (ppm) |
|---|---|---|
| B1-11 | 7.75-7.87 (m, 10H, ArH), 7.63 (s, 2H, ArH), 4.94 (t, 2H, OCH2CF2), 4.84 (s, 2H, OCH2), 4.19 (s, 2H, CH2), 2.37 (s, 6H, CH3), 1.55-1.87 (m, 15H, Adamantane) | −77.7, −80.4, −119.7 |
| B1-12 | 7.75-7.87 (m, 10H, ArH), 7.63 (s, 2H, ArH), 4.94 (t, 2H, OCH2CF2), 4.84 (s, 2H, OCH2), 2.77-2.81 (m, 1H, Cyclohexyl), 2.37 (s, 6H, CH3), 2.04-2.08 (m, 2H, Cyclohexyl), 1.73-1.75 (m, 2H, Cyclohexyl), 1.56-1.59 (m, 1H, Cyclohexyl), 1.07-1.33 (m, 5H, Cyclohexyl) | −74.7, −80.4, −119.7 |
| B1-13 | 7.75-7.87 (m, 10H, ArH), 7.63 (s, 2H, ArH), 4.94 (t, 2H, OCH2CF2), 4.84 (s, 2H, OCH2), 2.37 (s, 6H, CH3), 1.55-1.88 (m, 15H, Adamantane) | −74.5, −80.4, −119.7 |
| B1-14 | 7.75-7.87 (m, 10H, ArH), 7.63 (s, 2H, ArH), 4.94 (t, 2H, OCH2CF2), 4.84 (s, 2H, OCH2), 2.37 (s, 6H, CH3), 1.59-2.13 (m, 15H, Adamantane) | −69.2, −76.0, −80.4, −112.9, −119.7 |
| B1-15 | 7.51-7.96 (m, 19H, Naph + ArH), 5.20 (s, 2H, CH2), 4.94 (t, 2H, OCH2CF2), 4.84 (s, 2H, OCH2), 2.37 (s, 6H, CH3) | −80.4, −113.7, −119.7 |

TABLE 11-continued

| Synthesis Example | $^1$H-NMR (DMSO-d6, 400 MHz): δ (ppm) | $^{19}$F-NMR (DMSO-d6, 376 MHz): δ (ppm) |
|---|---|---|
| B1-16 | 7.75-7.87 (m, 10H, ArH), 7.63 (s, 2H, ArH), 4.94 (t, 2H, OCH2CF2), 4.84 (s, 2H, OCH2), 2.37 (s, 6H, CH3), 2.09-1.56 (m, 15H, Adamantane) | −70.1, −80.4, −113.4, −119.7 |
| B1-17 | 7.75-7.87 (m, 10H, ArH), 7.63 (s, 2H, ArH), 4.94 (t, 2H, OCH2CF2), 4.84 (s, 2H, OCH2), 2.37 (s, 6H, CH3) | −73.7, −80.4, −119.7 |
| B1-18 | 7.75-7.87 (m, 10H, ArH), 7.63 (s, 2H, ArH), 4.94 (t, 2H, OCH2CF2), 4.84 (s, 2H, OCH2), 2.37 (s, 6H, CH3) | −76.2, −80.4, −119.7, −131.6, −149.7, −161.1 |
| B1-19 | 7.75-7.87 (m, 10H, ArH), 7.63 (s, 2H, ArH), 4.94 (t, 2H, OCH2CF2), 4.84 (s, 2H, OCH2), 2.88 (d, 1H, CH), 2.66-2.74 (m, 1H, CH), 2.37 (m, 7H, CH3 + CH), 2.17-2.24 (m, 1H, CH), 1.90 (t, 1H, CH), 1.74-1.89 (m, 2H, CH2), 1.22-1.29 (m, 2H, CH2), 1.03 (s, 3H, CH3), 0.71 (s, 3H, CH3) | −80.4, −119.7 |
| B1-20 | 7.75-7.87 (m, 10H, ArH), 7.63 (s, 2H, ArH), 4.94 (t, 2H, OCH2CF2), 4.84 (s, 2H, OCH2), 2.37 (s, 6H, CH3) | −75.0, −80.4, −119.7 |

TABLE 12

| Synthesis Example | $^1$H-NMR (DMSO-d6, 400 MHz): δ (ppm) | $^{19}$F-NMR (DMSO-d6, 376 MHz): δ (ppm) |
|---|---|---|
| B1-21 | 7.75-7.87 (m, 10H, ArH), 7.63 (s, 2H, ArH), 4.94 (t, 2H, OCH2CF2), 4.84 (s, 2H, OCH2), 2.37 (s, 6H, CH3) | −77.3, −80.4, −112.5, −119.7, −121.7 |
| B1-22 | 7.75-7.87 (m, 10H, ArH), 7.63 (s, 2H, ArH), 4.94 (t, 2H, OCH2CF2), 4.84 (s, 2H, OCH2), 2.37 (s, 6H, CH3) | −80.4, −116.9, −119.7, −123.0 |
| B1-23 | 7.75-7.87 (m, 10H, ArH), 7.63 (s, 2H, ArH), 4.94 (t, 2H, OCH2CF2), 4.84 (s, 2H, OCH2), 2.37 (s, 6H, CH3) | −75.9, −76.0, −80.4, −114.7, −119.7 |
| B1-24 | 7.75-7.87 (m, 10H, ArH), 7.63 (s, 2H, ArH), 5.83-5.92 (m, 1H, anion CH), 5.41 (dd, 1H, anion CH), 5.21 (dd, 1H, anion CH), 4.94 (t, 2H, OCH2CF2), 4.84 (s, 2H, OCH2), 4.45 (s, 2H, anion CH2), 2.37 (s, 6H, CH3) | −80.0, −80.4, −113.0, −119.7 |

Furthermore, compounds (B1-25) to (B1-46) were obtained in a similar manner to that in the above-mentioned [Synthesis Example 5] using various anions. Chemical formulas and NMR data for the compounds (B1-25) to (B1-46) are shown in the following Tables 13 to 17. The amount of each substance used during the salt exchange reaction is the same.

TABLE 13

| Synthesis Example | Reactant (Compound D) X$^-$M$^+$ |
|---|---|
| B1-25 | (structure: adamantyl-C(=O)-O-CH2CH2-O-C(=O)-CF2-SO3$^-$ H-N$^+$(Et)3) |
| B1-26 | (structure: adamantyl-C(=O)-O-CH2-CF2-SO3$^-$ H-N$^+$(Et)3) |

TABLE 13-continued
| | |
|---|---|
| B1-27 | 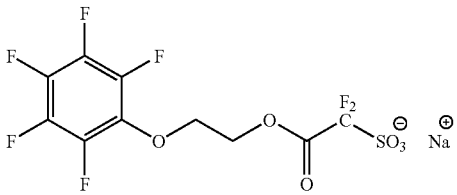 |
| B1-28 | 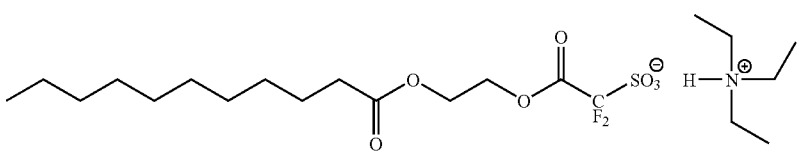 |
| B1-29 | 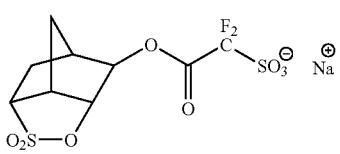 |
| B1-30 | 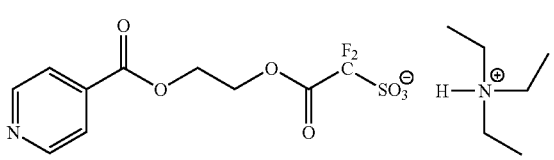 |
| B1-31 | 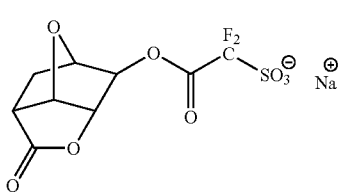 |
| B1-32 | 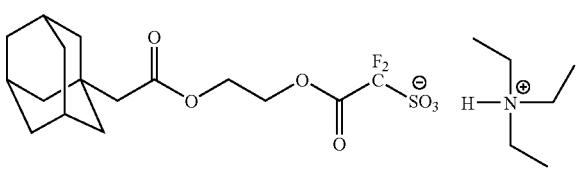 |
| B1-33 | 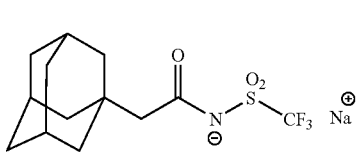 [SMILES: O=C(CC12CC3CC(CC(C3)C1)C2)[N-]S(=O)(=O)C(F)(F)F ; [Na+]] |
| B1-34 | 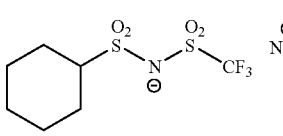 |
| Synthesis Example | Product | |
|---|---|---|
| | Anion | Cation |
| B1-25 | 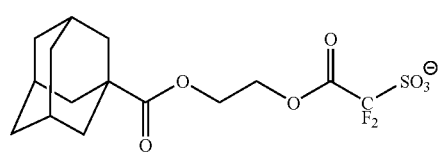 | (b1-11-3) |

TABLE 13-continued
B1-26 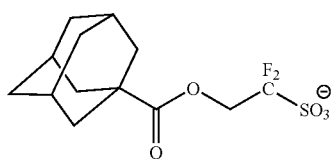 (b1-11-3)
B1-27 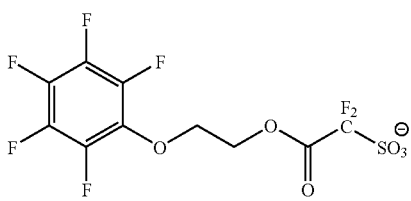 (b1-11-3)
B1-28 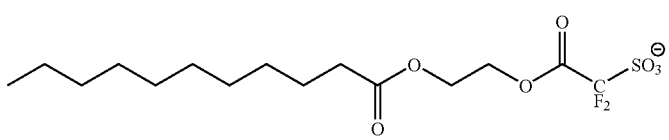 (b1-11-3)
B1-29 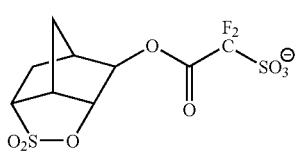 (b1-11-3)
B1-30 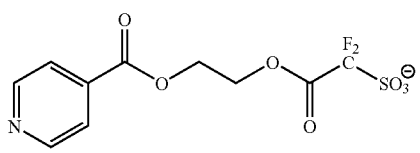 (b1-11-3)
B1-31 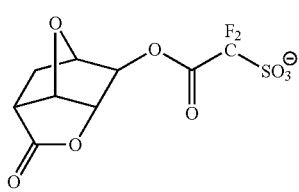 (b1-11-3)
B1-32 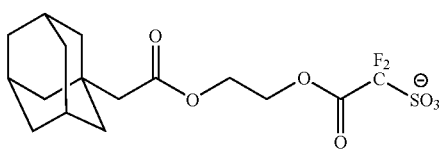 (b1-11-3)
B1-33 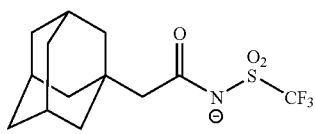 (b1-11-3)
B1-34 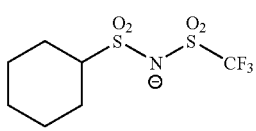 (b1-11-3)

TABLE 14

| Synthesis Example | Reactant (Compound D) X⁻M⁺ | Product Anion | Product Cation |
|---|---|---|---|
| B1-35 | Adamantyl-C(=O)-N⁻(SO₂CF₃), Na⁺ | Adamantyl-C(=O)-N⁻(SO₂CF₃) | (b1-11-3) |
| B1-36 | Adamantyl-O-CF₂-CF₂-SO₂-N⁻-SO₂-CF₃, Na⁺ | Adamantyl-O-CF₂-CF₂-SO₂-N⁻-SO₂-CF₃ | (b1-11-3) |
| B1-37 | Naphthyl-CH₂-O-CF₂-CF₂-SO₃⁻, Li⁺ | Naphthyl-CH₂-O-CF₂-CF₂-SO₃⁻ | (b1-11-3) |
| B1-38 | Adamantyl-O-CF₂-CF₂-SO₃⁻, Li⁺ | Adamantyl-O-CF₂-CF₂-SO₃⁻ | (b1-11-3) |
| B1-39 | (F₃CO₂S)(SO₂CF₃)C⁻(SO₂CF₃), H⁺ | (F₃CO₂S)(SO₂CF₃)C⁻(SO₂CF₃) | (b1-11-3) |

TABLE 15

| Synthesis Example | Reactant (Compound D) X⁻M⁺ | Product Anion | Product Cation |
|---|---|---|---|
| B1-40 | Pentafluorophenyl-C⁻(SO₂CF₃)(SO₂CF₃), H⁺ | Pentafluorophenyl-C⁻(SO₂CF₃)(SO₂CF₃) | (b1-11-3) |
| B1-41 | Camphorsulfonate, Na⁺ | Camphorsulfonate | (b1-11-3) |
| B1-42 | CF₃SO₃⁻ K⁺ | CF₃SO₃⁻ | (b1-11-3) |
| B1-43 | C₃F₇SO₃⁻ K⁺ | C₃F₇SO₃⁻ | (b1-11-3) |
| B1-44 | cyclic-(O₂S-N⁻-SO₂-CF₂-CF₂-CF₂), K⁺ | cyclic-(O₂S-N⁻-SO₂-CF₂-CF₂-CF₂) | (b1-11-3) |

TABLE 15-continued

| Synthesis Example | Reactant (Compound D) X⁻M⁺ | Product Anion | Product Cation |
|---|---|---|---|
| B1-45 | F₃CF₂C-S(O₂)-N⁻-S(O₂)-CF₃  K⁺ | F₃CF₂C-S(O₂)-N⁻-S(O₂)-CF₃ | (b1-11-3) |
| B1-46 | CH₂=CH-CH₂-O-CF₂-CF₂-SO₃⁻  Li⁺ | CH₂=CH-CH₂-O-CF₂-CF₂-SO₃⁻ | (b1-11-3) |

TABLE 16

| Synthesis Example | ¹H-NMR (DMSO-d6, 400 MHz): δ (ppm) | ¹⁹F-NMR (DMSO-d6, 376 MHz): δ (ppm) |
|---|---|---|
| B1-25 | 7.72-7.84 (m, 10H, ArH), 7.59 (s, 2H, ArH), 4.64 (s, 2H, CH2), 4.40 (t, 2H, CH2), 4.21 (t, 2H, CH2), 3.70 (s, OCH3), 2.29 (s, 6H, CH3), 1.61-1.98 (m, 15H, Adamantane) | −106.6 |
| B1-26 | 7.72-7.84 (m, 10H, ArH), 7.59 (s, 2H, ArH), 4.64 (s, 2H, CH2), 4.45 (t, 2H, CF2CH2), 3.70 (s, OCH3), 2.29 (s, 6H, CH3), 1.94-1.64 (m, 15H, Adamantane). | −111.2 |
| B1-27 | 7.72-7.84 (m, 10H, ArH), 7.59 (s, 2H, ArH), 4.64 (s, 2H, CH2), 4.40-4.50 (m, 4H, CH2), 3.70 (s, OCH3), 2.29 (s, 6H, CH3) | −106.7, −154.0, −160.0, −161.5 |
| B1-28 | 7.72-7.84 (m, 10H, ArH), 7.59 (s, 2H, ArH), 4.64 (s, 2H, CH2), 4.41(t, 2H, CH2), 4.23 (t, 2H, CH2), 3.70 (s, OCH3), 0.79-2.89 (m, 27H, CH2 + Undecanoyl) | −106.8 |
| B1-29 | 7.72-7.84 (m, 10H, ArH), 7.59 (s, 2H, ArH), 4.78 (m, 1H, CH), 4.64-4.66 (m, 3H, CH2 + CH), 3.88 (t, 1H, CH), 3.70 (s, OCH3), 3.34 (m, 1H, CH), 2.49 (m, 1H, CH), 1.73-2.29 (m, 10H, CH3 + CH2). | −107.7 |
| B1-30 | 8.74-8.82 (m, 2H, Py-H), 7.72-7.84 (m, 12H, ArH + Py-H), 7.59 (s, 2H, ArH), 4.54-4.64 (m, 6H, CH2 + CH2CH2), 3.70 (s, OCH3), 2.29 (s, 6H, CH3). | −106.5 |
| B1-31 | 7.72-7.84 (m, 10H, ArH), 7.59 (s, 2H, ArH), 5.46 (t, 1H, Oxo-norbornane), 4.97 (s, 1H, Oxo-norbornane), 4.71 (d, 1H, Oxo-norbornane), 4.64 (s, 2H, CH2), 4.57 (d, 1H, Oxonorbornane), 3.70 (s, OCH3), 2.69-2.73 (m, 1H, Oxo-norbornane), 2.29 (s, 6H, CH3), 2.06-2.16 (m, 2H, Oxo-norbornane) | −107.1 |
| B1-32 | 7.72-7.84 (m, 10H, ArH), 7.59 (s, 2H, ArH), 4.64 (s, 2H, CH2), 4.40 (t, 2H, CH2), 4.20 (t, 2H, CH2), 3.70 (s, OCH3), 2.29 (s, 6H, CH3), 2.05 (s, 2H, CH2), 1.53-1.95 (m, 15H, Adamantane) | −111.2 |
| B1-33 | 7.72-7.84 (m, 10H, ArH), 7.59 (s, 2H, ArH), 4.64 (s, 2H, CH2), 4.19 (s, 2H, CH2), 3.70 (s, OCH3), 2.29 (s, 6H, CH3), 1.55-1.87 (m, 15H, Adamantane) | −77.7 |
| B1-34 | 7.72-7.84 (m, 10H, ArH), 7.59 (s, 2H, ArH), 4.64 (s, 2H, CH2), 3.70 (s, OCH3), 2.77-2.81 (m, 1H, Cyclohexyl), 2.29 (s, 6H, CH3), 2.04-2.08 (m, 2H, Cyclohexyl), 1.73-1.75 (m, 2H, Cyclohexyl), 1.56-1.59 (m, 1H, Cyclohexyl), 1.07-1.33 (m, 5H, Cyclohexyl) | −74.7 |
| B1-35 | 7.72-7.84 (m, 10H, ArH), 7.59 (s, 2H, ArH), 4.64 (s, 2H, CH2), 3.70 (s, OCH3), 2.29 (s, 6H, CH3), 1.55-1.88 (m, 15H, Adamantane) | −74.5 |

TABLE 17

| Synthesis Example | ¹H-NMR (DMSO-d6, 400 MHz): δ (ppm) | ¹⁹F-NMR (DMSO-d6, 376 MHz): δ (ppm) |
|---|---|---|
| B1-36 | 7.72-7.84 (m, 10H, ArH), 7.59 (s, 2H, ArH), 4.64 (s, 2H, CH2), 3.70 (s, OCH3), 2.29 (s, 6H, CH3), 1.59-2.13 (m, 15H, Adamantane) | −69.2, −76.0, −112.9 |
| B1-37 | 7.51-7.96 (m, 19H, Naph + ArH), 5.20 (s, 2H, CH2), 4.64 (s, 2H, CH2), 3.70 (s, OCH3), 2.29 (s, 6H, CH3). | −80.5, −113.7 |
| B1-38 | 7.72-7.84 (m, 10H, ArH), 7.59 (s, 2H, ArH), 4.64 (s, 2H, CH2), 3.70 (s, OCH3), 2.29 (s, 6H, CH3), 1.56-2.09 (m, 15H, Adamantane) | −70.1, −113.4 |
| B1-39 | 7.72-7.84 (m, 10H, ArH), 7.59 (s, 2H, ArH), 4.64 (s, 2H, CH2), 3.70 (s, OCH3), 2.29 (s, 6H, CH3). | −73.7 |
| B1-40 | 7.72-7.84 (m, 10H, ArH), 7.59 (s, 2H, ArH), 4.64 (s, 2H, CH2), 3.70 (s, OCH3), 2.29 (s, 6H, CH3). | −161.1, −149.7, −131.6, −76.2 |

TABLE 17-continued

| Synthesis Example | $^1$H-NMR (DMSO-d6, 400 MHz): δ (ppm) | $^{19}$F-NMR (DMSO-d6, 376 MHz): δ (ppm) |
|---|---|---|
| B1-41 | 7.72-7.84 (m, 10H, ArH), 7.59 (s, 2H, ArH), 4.64 (s, 2H, CH2), 3.70 (s, OCH3), 2.88 (d, 1H, CH), 2.66-2.74 (m, 1H, CH), 2.37 (d, 1H, CH), 2.29 (s, 6H, CH3), 2.17-2.24 (m, 1H, CH), 1.90 (t, 1H, CH), 1.74-1.89 (m, 2H, CH2), 1.22-1.29 (m, 2H, CH2), 1.03 (s, 3H, CH3), 0.71 (s, 3H, CH3) | No fluorine |
| B1-42 | 7.72-7.84 (m, 10H, ArH), 7.59 (s, 2H, ArH), 4.64 (s, 2H, CH2), 3.70 (s, OCH3), 2.29 (s, 6H, CH3). | −75 |
| B1-43 | 7.72-7.84 (m, 10H, ArH), 7.59 (s, 2H, ArH), 4.64 (s, 2H, CH2), 3.70 (s, OCH3), 2.29 (s, 6H, CH3). | −77.3, −112.5, −121.7 |
| B1-44 | 7.72-7.84 (m, 10H, ArH), 7.59 (s, 2H, ArH), 4.64 (s, 2H, CH2), 3.70 (s, OCH3), 2.29 (s, 6H, CH3). | −116.9, −123.0 |
| B1-45 | 7.72-7.84 (m, 10H, ArH), 7.59 (s, 2H, ArH), 4.64 (s, 2H, CH2), 3.70 (s, OCH3), 2.29 (s, 6H, CH3) | −75.9, −76.0, −114.7 |
| B1-46 | 7.72-7.84 (m, 10H, ArH), 7.59 (s, 2H, ArH), 5.38-5.92 (m, 1H, anion CH), 5.41 (dd, 1H, anion CH), 5.21 (dd, 1H, anion CH), 4.64 (s, 2H, CH2), 4.45 (s, 2H, anion CH2), 3.70 (s, OCH3), 2.29 (s, 6H, CH3) | −80.0, −113.0 |

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition comprising:
a base component (A) which exhibits changed solubility in an alkali developing solution under action of acid; and
an acid-generator component (B) which generates acid upon exposure,
wherein said acid-generator component (B) includes an acid generator (B1) composed of a compound having a base dissociable group within a cation moiety, and
wherein said base dissociable group is a group represented by general formula (I) shown below:

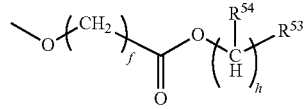
(I)

wherein $R^{53}$ represents a fluorinated alkyl group; $R^{54}$ represents a hydrogen atom, an alkyl group or a fluorinated alkyl group; f represents 0 or 1; and h represents 1 or 2.

2. The resist composition according to claim 1, wherein said acid generator (B1) includes a compound represented by general formula (b1-11) shown below:

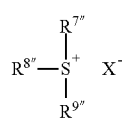
(b1-11)

wherein $R^{7''}$ to $R^{9''}$ each independently represents an aryl group or an alkyl group, wherein two of $R^{7''}$ to $R^{9''}$ may be bonded to each other to form a ring with the sulfur atom in the formula, and at least one of $R^{7''}$ to $R^{9''}$ represents a substituted aryl group having said group represented by general formula (I) as a substituent; and $X^-$ represents an anion.

3. The resist composition according to claim 2, wherein $X^-$ in said general formula (b1-11) is any one of anions selected from the group consisting of sulfonate anions, imide anions, methide anions, and halogen anions.

4. The resist composition according to claim 1 and which is a positive resist composition,
wherein said base component (A) is a base component (A1) which exhibits increased solubility in an alkali developing solution under action of acid.

5. The resist composition according to claim 4,
wherein said base component (A1) includes a resin component (A1-1) which exhibits increased solubility in an alkali developing solution under action of acid, and
said resin component (A1-1) has a structural unit (a1) derived from an acrylate ester containing an acid dissociable, dissolution inhibiting group.

6. The resist composition according to claim 1, further comprising a cross-linking agent (C), and which is a negative resist composition,
wherein said base component (A) is a base component (A2) that is soluble in an alkali developing solution.

7. The resist composition according to claim 1, further comprising a nitrogen-containing organic compound (D).

8. A method of forming a resist pattern, comprising:
applying the resist composition of claim 1 to a substrate to form a resist film on the substrate;
subjecting said resist film to exposure; and
subjecting said resist film to alkali developing to form a resist pattern.

9. A compound represented by general formula (b1-11) shown below:

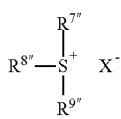
(b1-11)

wherein R⁷‴ to R⁹‴ each independently represents an aryl group or an alkyl group, wherein two of R⁷‴ to R⁹‴ may be bonded to each other to form a ring with the sulfur atom in the formula, and at least one of R⁷‴ to R⁹‴ represents a substituted aryl group having a group represented by general formula (I) shown below as a substituent; and X⁻ represents an anion:

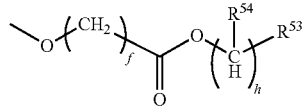
(I)

wherein $R^{53}$ represents a fluorinated alkyl group; $R^{54}$ represents a hydrogen atom, an alkyl group or a fluorinated alkyl group; f represents 0 or 1; and h represents 1 or 2.

10. The compound according to claim 9, wherein X⁻ in said general formula (b1-11) is any one of anions selected from the group consisting of sulfonate anions, imide anions, methide anions, and halogen anions.

11. An acid generator comprising the compound of claim 10.

12. An acid generator comprising the compound of claim 9.

* * * * *